United States Patent
Herman et al.

(10) Patent No.: US 10,332,053 B2
(45) Date of Patent: Jun. 25, 2019

(54) FOOD DATA ACCESS AND DELIVERY SYSTEM

(71) Applicant: TUTSHO, LLC, Bellevue, WA (US)

(72) Inventors: Michele K. Herman, Bellevue, WA (US); Deepak Kamlani, Alamo, CA (US); David S. Montague, Bellevue, WA (US); Rohan Phillips, Redmond, WA (US)

(73) Assignee: TUTSHO, LLC, Bellevue, WA (US)

( * ) Notice: Subject to any disclaimer, the term of this patent is extended or adjusted under 35 U.S.C. 154(b) by 354 days.

(21) Appl. No.: 15/190,952

(22) Filed: Jun. 23, 2016

(65) Prior Publication Data

US 2016/0307128 A1 Oct. 20, 2016

Related U.S. Application Data

(63) Continuation-in-part of application No. 14/766,866, filed as application No. PCT/US2014/016326 on Feb. 13, 2014.

(Continued)

(51) Int. Cl.
*G06F 7/00* (2006.01)
*G06F 17/30* (2006.01)
(Continued)

(52) U.S. Cl.
CPC ..... *G06Q 10/0633* (2013.01); *G06F 16/9537* (2019.01); *G06F 19/3475* (2013.01);
(Continued)

(58) Field of Classification Search
CPC ............ G06Q 10/0633; G06Q 20/202; G06K 7/10861; H04L 67/18; G06F 17/30864;
(Continued)

(56) References Cited

U.S. PATENT DOCUMENTS

| 4,151,668 A | * | 5/1979 | Hungerford | ............ G09F 11/23 40/495 |
| 5,774,871 A | * | 6/1998 | Ferro | ..................... G06Q 20/20 128/921 |

(Continued)

OTHER PUBLICATIONS

Kaiser Permanete; "Keeping A Food Diary Doubles Diet Weight Loss, Study Suggests"; Science Daily; Jul. 2008; 5 pages.
(Continued)

*Primary Examiner* — Binh V Ho
(74) *Attorney, Agent, or Firm* — Thomas Horstemeyer, LLP

(57) ABSTRACT

An improved system for accessing food data and tracking a user's food intake includes a nutrition information system 600 and a mobile PDA or smartphone-based tag reading system 900. The two systems 600 and 900 are configured to communication. The mobile tag reading system 900 includes a tag capture device 902 for reading the nutritional tag, and a decoder 904 for decoding the header or visual effects included in the nutritional tag to identify the predetermined profile. The decoder 904 is also configured to decode the nutritional tag to generate the subset of the dietary product descriptions and associated nutritional values based upon the predetermined profile. A tracking log 908 is included for storing the associated nutritional values or the modified associated nutritional values based upon input from the user.

40 Claims, 47 Drawing Sheets

Related U.S. Application Data

(60) Provisional application No. 61/764,172, filed on Feb. 13, 2013, provisional application No. 62/184,160, filed on Jun. 24, 2015, provisional application No. 62/197,854, filed on Jul. 28, 2015, provisional application No. 62/293,230, filed on Feb. 9, 2016, provisional application No. 62/293,709, filed on Feb. 10, 2016, provisional application No. 62/334,078, filed on May 10, 2016.

(51) Int. Cl.

| | | |
|---|---|---|
| *G06Q 10/06* | (2012.01) | |
| *G06Q 20/20* | (2012.01) | |
| *H04L 29/08* | (2006.01) | |
| *G06F 19/00* | (2018.01) | |
| *G06F 16/9537* | (2019.01) | |
| *G06Q 50/12* | (2012.01) | |

(52) U.S. Cl.
CPC ........... *G06Q 20/202* (2013.01); *H04L 67/18* (2013.01); *G06Q 50/12* (2013.01)

(58) Field of Classification Search
CPC . G06F 17/30312; G06F 3/0482; G06F 3/0484
USPC .......................................................... 707/758
See application file for complete search history.

(56) References Cited

U.S. PATENT DOCUMENTS

| | | | | |
|---|---|---|---|---|
| 6,038,546 | A * | 3/2000 | Ferro | G06Q 30/06 705/15 |
| 6,356,940 | B1 * | 3/2002 | Short | G06F 19/3475 709/217 |
| 7,680,690 | B1 * | 3/2010 | Catalano | G06Q 30/02 186/38 |
| 8,690,578 | B1 * | 4/2014 | Nusbaum | G09B 19/00 434/127 |
| 8,924,239 | B1 * | 12/2014 | Kurple | G06F 19/3475 705/2 |
| 2002/0047867 | A1 | 4/2002 | Mault | A61B 5/1118 715/810 |
| 2003/0208110 | A1 * | 11/2003 | Mault | A61B 5/0002 600/300 |
| 2003/0208383 | A1 * | 11/2003 | Hauck | G06F 19/324 705/3 |
| 2003/0208409 | A1 * | 11/2003 | Mault | G06F 19/3475 705/15 |
| 2004/0103043 | A1 * | 5/2004 | Reade | G06Q 20/208 705/23 |
| 2006/0064447 | A1 * | 3/2006 | Malkov | G06F 15/16 708/200 |
| 2006/0081711 | A1 | 4/2006 | Zhao et al. | |
| 2007/0094090 | A1 * | 4/2007 | Jenkins | G06Q 30/0603 705/15 |
| 2008/0086374 | A1 * | 4/2008 | Aitken | G06F 19/3475 705/14.27 |
| 2008/0296380 | A1 | 12/2008 | Karkanias et al. | |
| 2009/0099873 | A1 * | 4/2009 | Kurple | G06Q 50/24 705/3 |
| 2009/0192901 | A1 * | 7/2009 | Egeresi | G06Q 10/00 705/15 |
| 2010/0264205 | A1 | 10/2010 | Iida | |
| 2011/0301446 | A1 | 12/2011 | Kamen | |
| 2012/0072233 | A1 * | 3/2012 | Hanlon | G06Q 30/0271 705/2 |
| 2012/0175413 | A1 | 7/2012 | Harris | |
| 2013/0105565 | A1 * | 5/2013 | Kamprath | G06F 19/00 235/375 |
| 2014/0245120 | A1 * | 8/2014 | Schwartz | G06K 9/00402 715/226 |
| 2014/0287384 | A1 * | 9/2014 | Boyes | G06F 19/3475 434/127 |
| 2015/0154883 | A1 * | 6/2015 | Klassen | A61K 31/137 514/282 |
| 2015/0235562 | A1 * | 8/2015 | Klein | G09B 5/02 434/127 |

OTHER PUBLICATIONS

Cordeiro et al.; "Barriers and Negative Nudges: Exploring Challenges in Food Journaling"; CHI2015; Apr. 2015; 4 pages.
"Nutritionix API"; http://www.nutritionix.com/business/api; © 2016; accessed Jul. 8, 2016; 4 pages.
Pehrsson, Pamela R.; "USDA—United States Department of Agriculture Research Service"; https://www.ars.usda.gov/main/site_main.htm?modecode=80-40-05-25; accessed Jul. 8, 2016; 2 pages.
"Composition of Foods Raw, Processed, Prepared"; USDA National Nutrient Database for Standard Reference, Release 27; Documentation and User Guide; Aug. 2014; 154 pages.
"National Nutrient Database for Standard Reference Release 28"; United States Department of Agriculture Research Service; https://ndb.nal.usda.gov/ndb/doc/index; May 2016; accessed Jul. 8, 2016; 2 pages.
"Egg Allergy—Living With Food Allergies"; Kids With Food Allergies—A Division of the Asthma and Allergy Foundation of America; http://www.kidswithfoodallergies.org/page/egg-allergy.aspx; © 2005-2016; accessed Jul. 8, 2016.
"Fish Allergy"; FARE—Food Allergy Research & Education; http://www.foodallergy.org/allergens/fish-allergy; © 2016; accessed Jul. 8, 2016; 4 pages.
"Shellfish"; FARE—Food Allergy Research & Education; http://www.foodallergy.org/allergens/shellfish-allergy; © 2016; accessed Jul. 8, 2016; 4 pages.
"Milk Allergy—Living With Food Allergies"; Kids With Food Allergies—A Division of the Asthma and Allergy Foundation of America; http://www.kidswithfoodallergies.org/page/milk-allergy.aspx; © 2005-2016; accessed Jul. 8, 2016; 6 pages.
"Peanut Allergy—Living With Food Allergies"; Kids With Food Allergies—A Division of the Asthma and Allergy Foundation of America; http://www.kidswithfoodallergies.org/page/peanut-allergy.aspx; © 2005-2016; accessed Jul. 8, 2016; 6 pages.
"Tree Nut Allergy—Living With Food Allergies"; Kids With Food Allergies—A Division of the Asthma and Allergy Foundation of America; http://www.kidswithfoodallergies.org/page/tree-nut-allergy.aspx; © 2005-2016; accessed Jul. 8, 2016; 6 pages.
"Soy—Living With Food Allergies"; Kids With Food Allergies—A Division of the Asthma and Allergy Foundation of America; http://www.kidswithfoodallergies.org/page/soy-allergy.aspx' © 2005-2016; accessed Jul. 8, 2016; 6 pages.
"Wheat—Living With Food Allergies"; Kids With Food Allergies—A Division of the Asthma and Allergy Foundation of America; http://www.kidswithfoodallergies.org/page/wheat-allergy.aspx; © 2005-2016; accessed Jul. 8, 2016; 6 pages.

* cited by examiner

FIGURE 3

| Venue Name | Ma's Diner |
|---|---|
| Network ID | 77123 |
| Item Number | 0001 |
| Item Name | Prime Rib Dinner |

| Sub Items | Ingredients | Amount | Units |
|---|---|---|---|
| Prime Rib | Prime Rib | 8 | Oz. |
| | Add+ | | |
| Garlic Mashed Potatoes | Potato | 1/2 | n/a |
| | Whole milk | 1/4 | cup |
| | Garlic | 2 | cloves |
| | Acme-Brand Butter | 2 | TBSP |
| | Salt | 1/8 | Tsp |
| | Pepper | 1/8 | Tsp |
| | Add+ | | |
| Seasonal Vegetables | Zucchini | 1/3 | cup |
| | Yellow Squash | 1/3 | cup |
| | Red Bell Pepper | 1/3 | cup |
| | Cauliflower | 1/3 | cup |
| | Olive Oil | 1/2 | Tsp |
| | Fresh Rosemary | 1/2 | Tsp |
| | Add + | | |

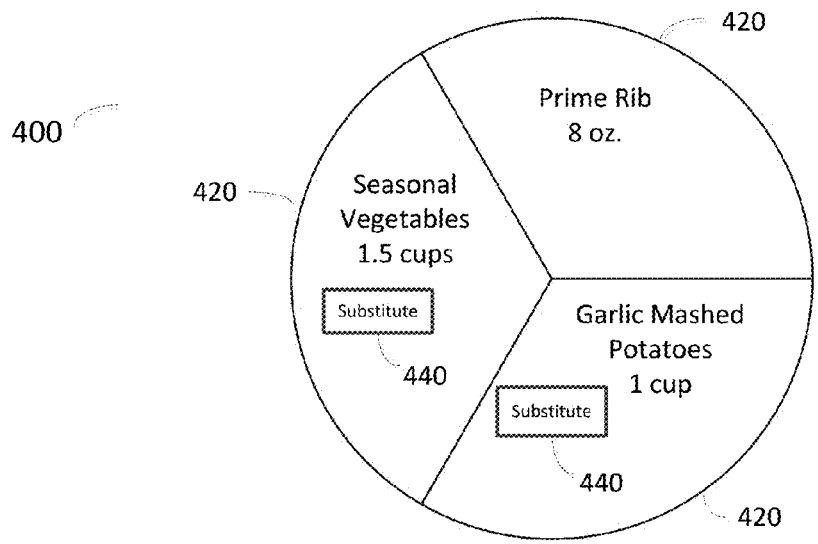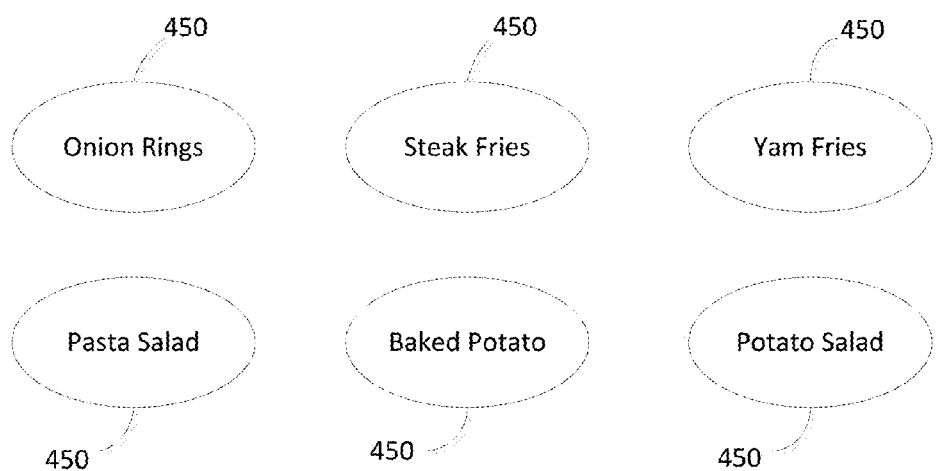
FIGURE 5C

FIGURE 7B

| | |
|---|---|
| Name | Bob |
| Network ID | 123456 |

[ Make Change ]

| | |
|---|---|
| Venue Name | Ma's Diner |
| Item Name | Prime Rib Dinner |

| Sub Items | Amount | Units |
|---|---|---|
| Prime Rib | 8 | Oz. |
| [ Portion Size ] | | [ Substitute ] |
| Prime Rib | 6 | Oz. |
| Garlic Mashed Potatoes | 1 | cup |
| [ Portion Size ] | | [ Substitute ] |
| Garlic Mashed Potatoes | 1/2 | cup |
| Seasonal Vegetables | 1.5 | cup |
| [ Portion Size ] | | [ Substitute ] |
| Seasonal Vegetables | 1 | cup |

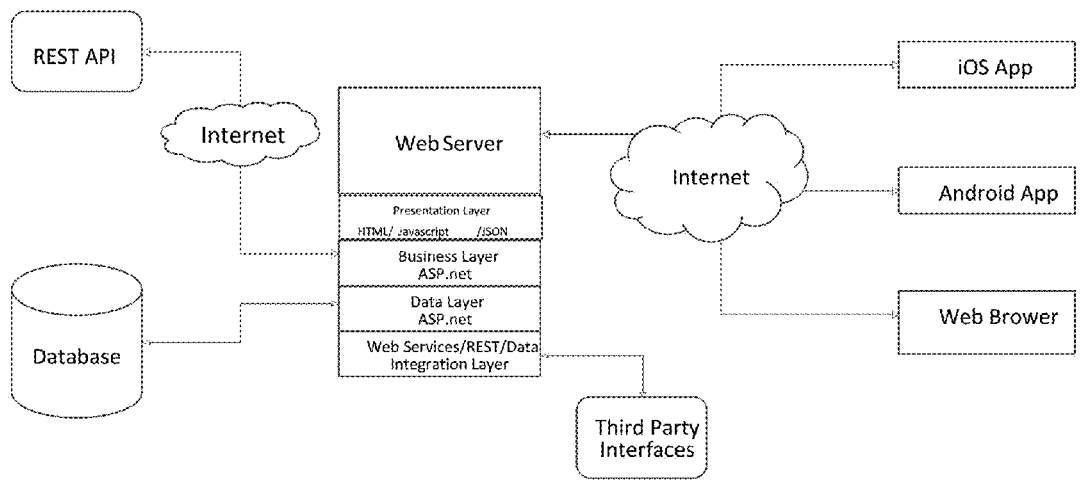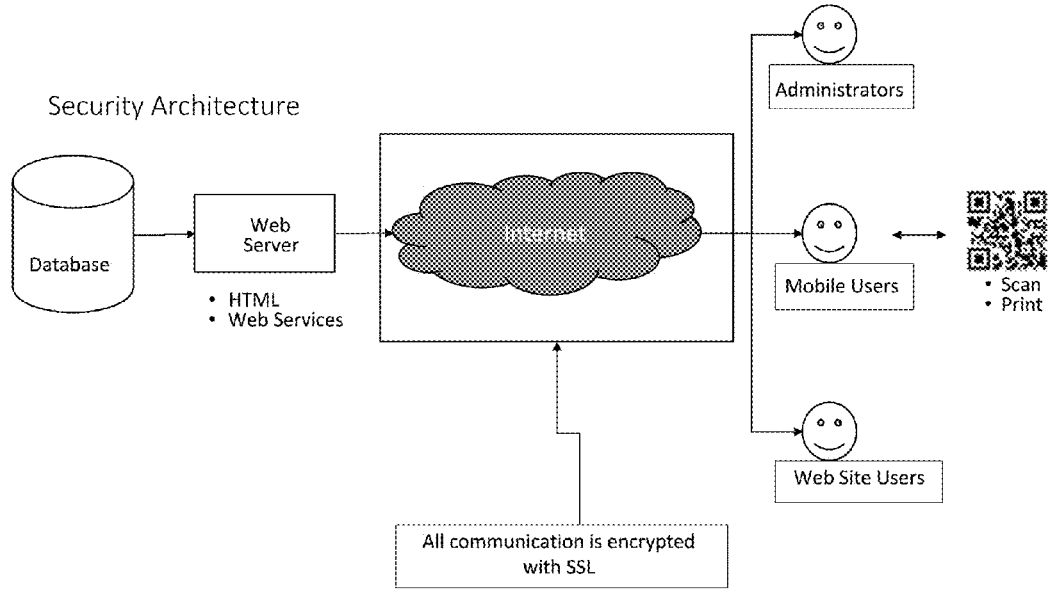
FIGURE 13

Address bar and navigation tools

Logo and general info

Reset Password

| Email address | ? |

| Reset Password | | Not Registered |

| CR | Terms of Use | About | Feedback | B2B | B2C |

FIGURE 17O

Address bar and navigation tools

Logo and general info

Forgot Email Address

| Display name |

Display Email Address

| Return to Login | | Not Registered |

| CR | Terms of Use | About | Feedback | B2B | B2C |

FIGURE 17P

Address bar and navigation tools

Logout or Edit profile

Logo and general info

Feedback

Subject of Feedback

Submit

Your Feedback Text

CR  Terms of Use  About  B2B  B2C

FOOD DATA ACCESS AND DELIVERY SYSTEM

CROSS REFERENCE TO RELATED APPLICATIONS

This application claims priority to U.S. application Ser. No. 14/766,866, "Electronically Readable Dietary Tag and Reader," filed Aug. 10, 2015, which claims priority to PCT/US2014/016326, "Electronically Readable Dietary Tag and Reader," filed Feb. 13, 2014, which claims priority to U.S. Provisional Application No. 61/764,172, "Electronically Readable Dietary Tag and Reader," filed Feb. 13, 2013. Each of these applications is hereby incorporated by reference in its entirety.

This application also claims priority to: U.S. Provisional Patent Application No. 62/184,160, "Electronically Readable Dietary Tag and Reader," filed Jun. 24, 2015; U.S. Provisional Patent Application No. 62/197,854, "Electronically Readable Dietary Tag and Reader," filed Jul. 28, 2015; U.S. Provisional Patent Application No. 62/293,230, "Electronically Readable Dietary Tag and Reader," filed Feb. 9, 2016; U.S. Provisional Patent Application No. 62/293,709, "Electronically Readable Dietary Tag and Reader," filed Feb. 10, 2016; and U.S. Provisional Patent Application No. 62/334,078, "Scannable Nutrition Coded Tag Integration," filed May 10, 2016. Each of these applications is hereby incorporated by reference in its entirety.

TECHNICAL FIELD

The present application relates generally to the field of food data access systems, and more specifically to technical improvements in the field of computer-based identification of food data and systems for delivering food data on demand.

BACKGROUND

Studies have shown that people who track what they eat on paper, in an app, or in some other record, have better success at losing weight, managing their diet, controlling their portions, and sticking to healthy eating habits. For example, individuals who keep a food diary, or a regular log of what they've eaten and when, are more conscious of what they've eaten and are better able to maintain a healthy diet, even without counting calories. One study concluded that people who kept a journal were more likely to keep the weight they lost off, and another review of studies concluded that people who kept a record of their meals and kept up with diet and exercise lost nearly twice as much weight as people who did not keep a log. (Kaiser Permanente. "Keeping A Food Diary Doubles Diet Weight Loss, Study Suggests." ScienceDaily, 8 Jul. 2008. www.sciencedaily.com/releases/2008/07/080708080738.htm.)

Tools have been developed to help individuals track their diets. Current trackers enable users to access food data by searching various databases of foods. There are many drawbacks, however, with this approach. The databases are often incomplete and the foods that the user is searching for are not included or the search results do not correlate well to the intended food the user is searching for. For example, searching for peppers brings up different color peppers, different kinds of peppers, e.g., chili versus bell, and different spices.

More importantly, many databases are created with crowd-sourced data so that the data may not be accurate nor is it clear what food information was used to generate each of the food entries. To illustrate this problem, one can do a search using a popular food tracker called MyFitnessPal (MFP) for Chicken Tikka Marsala. The MFP tracker returns approximately 20,000 results all of which are based on different recipes, possibly sides like rice that are served with the dish, and other factors that are not known to the user initiating the search. If the user has ordered a menu item from a restaurant, he may be able to narrow the search by entering the restaurant name as a search term. But even doing that still creates a long list of items that the user needs to search through to try to estimate which item approximates the food that the user is searching for. To illustrate this, consider the following. Potbelly sandwich shops provide a nutrition information page for their sandwiches. A Wreck sandwich is served on multigrain bread, with roast beef, turkey salami, ham and Swiss cheese. Some people choose different kinds of breads, make different meat and cheese choices, and add different toppings (tomatoes, mayo, etc.). A search in MFP for a Potbelly A Wreck sandwich yields 135 different search results ranging from about 220 calories to about 800 calories. There is no way to tell which result, if any, match the combination of ingredients the user is interested in and there is no way from the listing alone that a user could determine if the data is accurate. A user could go to the Potbelly nutrition page and make the custom selections he is interested in and calculate the corresponding nutrition information but then the user would have to manually enter that information into his tracker and save a new Potbelly A Wreck sandwich, making a 136th entry.

Some restaurants also provide only very incomplete information such as the total number of calories for the cheeseburger and fries. There is no way for a user to modify the information if the user only plans to eat half the fries, substitute the fries for a salad, decides to hold the cheese, or adds BBQ sauce to the burger. Other restaurants and venues where people eat, e.g., banquets, company picnics, grab and go counters, pot lucks, dinner parties, etc., don't provide any nutrition information for the foods being served. So a user can only search for the individual ingredients that are easily identifiable in the food served.

Given all of these challenges it is extremely inefficient, time consuming and tedious to ascertain food data and track it. The problems that individuals face in food tracking today are well documented in *Barriers and Negative Nudges: Exploring Challenges in Food Journaling*, Cordeiro et al. (available at http://www.depstein.net/pubs/fcordeiro_chil5.pdf). The inventive system described below addresses these challenges.

SUMMARY

The inventive system improves the process of tracking consumption for a large variety of foods, including those prepared from recipes or served by venues, thus making it easier and more efficient for individuals to make better choices. Illustrative embodiments of the present invention coordinate the use of ubiquitous technology to enable a user's smartphone to record the data important to the user's unique nutrition needs, whether at a store, restaurant, kitchen, or wherever else food items are consumed.

In an exemplary embodiment, the present invention provides a tag reading system configured for use with a nutrition information system, where the nutrition information system includes a database storing dietary product descriptions and associated nutritional information. A computer coupled to the database is configured to generate a nutritional tag representing a subset of the dietary product descriptions and associated nutritional information based upon one of a plurality of predetermined profiles. The nutritional tag includes a header or visual effects, or both. The header or visual effects are coded symbols representing a specific predetermined profile.

In the exemplary embodiment, the tag reading system includes a tag capture device for reading the nutritional tag, a decoder for decoding the header or visual effects included in the nutritional tag to identify the predetermined profile, and then decoding the nutritional tag to generate the subset of the dietary product descriptions and associated nutritional values based upon the predetermined profile. A tracking log is also included in the tag reading system for accumulating nutritional values extracted from previously read nutritional tags. A tracking log modification module is also included for creating modified nutritional values in the tracking log based on food substitutions selected by the user.

The structure of the nutritional tags in combination with the structural features of the nutrition information system and tag reading system, including logical structures and processes, synergistically cause a number of advantageous technical effects. Importantly, the system is more efficient in logging users' daily food intake. Moreover, the system is able to more accurately, and more precisely, log the users' food intake. The use of a central database storing dietary product descriptions and nutritional information, in combination with the inventive nutrition tags and smartphone-based tag reading system, improves the process of collecting, organizing, and presenting nutrition data for a large variety of foods.

Other aspects of the present invention are described below.

BRIEF DESCRIPTION OF THE DRAWINGS

The foregoing summary, as well as the following detailed description are better understood when read in conjunction with the appended drawings. For the purpose of illustrating the invention, there is shown in the drawings exemplary constructions of the invention; however, the invention is not limited to the specific methods and instrumentalities disclosed. Like reference numerals refer to like elements throughout the drawings.

FIG. 3 shows a sample input screen in connection with the tag generator application.

FIG. 5C shows an exemplary user interface that could be used by a user to substitute one sub-item for another.

FIG. 7B shows an exemplary user interface populated for changing portion sizes.

FIG. 13 depicts an illustrative architecture including a database server, application server, and user level.

DETAILED DESCRIPTION OF ILLUSTRATIVE EMBODIMENTS

We will now describe illustrative embodiments of the present invention. With reference to FIGS. 1-11, we provide a detailed description of various aspects on our inventive solutions to the problems encountered in the prior art. Then, with reference to FIGS. 12-18C we describe exemplary user interface elements. Finally, with reference to FIG. 19, we describe our overall system for tracking a user's food intake, including a database storing dietary product descriptions and associated nutritional information, a computer configured to generate a nutritional tag, and a mobile tag reading system.

I. Electronically Readable Dietary Tag and Reader, FIGS. 1-11

Figure 1:
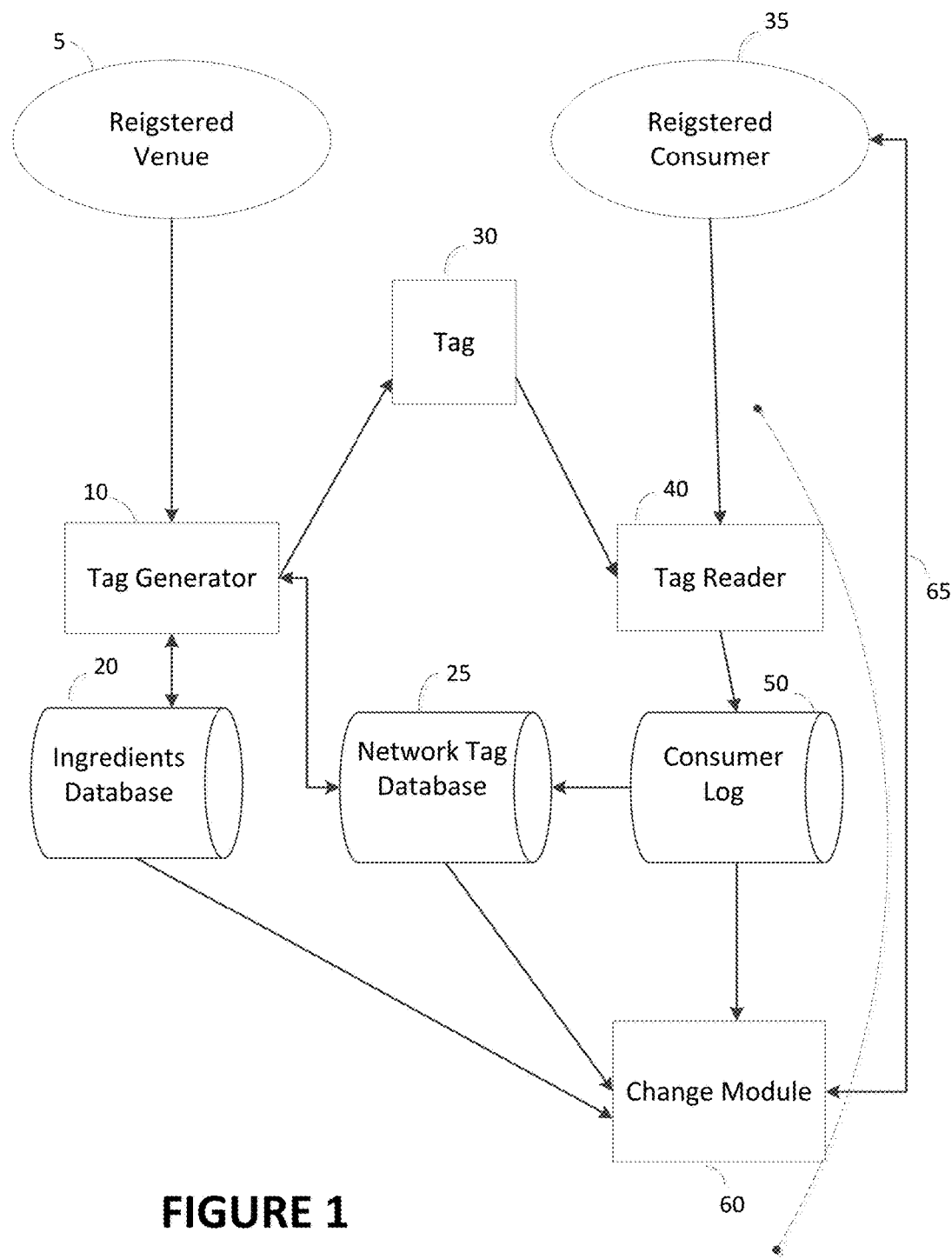
FIG. 1 shows a system according to one embodiment of the invention.

One embodiment of the present invention contemplates an electronically readable tag as described in U.S. Provisional Patent Application Nos. 62/184,160 and 62/197,854, entitled "Electronically Readable Dietary Tag and Reader" filed Jun. 24 and Jul. 28, 2015, respectively. FIG. 1 shows a system according to one embodiment of the invention. A venue that serves or sells foods would use a tag generator application 10 to generate an encoded tag 30. Preferably the tag generator application interfaces to an ingredients database 20 that stores nutritional and other information such as allergens or other substances that may be found in the various ingredients that are used to make items that the venue serves or sells to its customers. The tag generator application compiles the information and stores it in the network tag database 25. The tag generator application 10 encodes the information according to a predetermined profile as described, for example, in U.S. application Ser. No. 14/766, 866. The venue may print the tag on a sales receipt, on menus, on signage or in any other manner that may be used to associate the tag with the corresponding item. It should be understood that the tag may be provided in electronic form or transmitted to a user in a variety of ways. Several of such ways are described in U.S. application Ser. No. 14/766,866.

A user having a tag reader 40 will scan a tag associated with an item that a user has consumed or is considering consuming. The tag reader 40 is configured to decode the scanned tag. Once the scanned tag is decoded, the decoded information is stored in the user's log 50. If the user desires to modify the logged information by changing the portion size or making a substitution, the user may invoke the change module 60. A user could make the changes before anything is logged and then only log after the changes are made. In one embodiment of the invention the tag reader 40, consumer log 50 and change module 60 are all part of a user application 65 accessible from one or more of the user's devices such as a mobile phone, laptop computer, tablet, desk top computer, wearable device or any other computing device. The change module 60 connects to the network tag database 25 and the ingredients database 20 to look up the relevant changes and overwrite the new information in the log 50. In one embodiment of the invention the network tag database 25 is stored on a secure server that is accessible only to registered venues and registered users.

Figure 2:
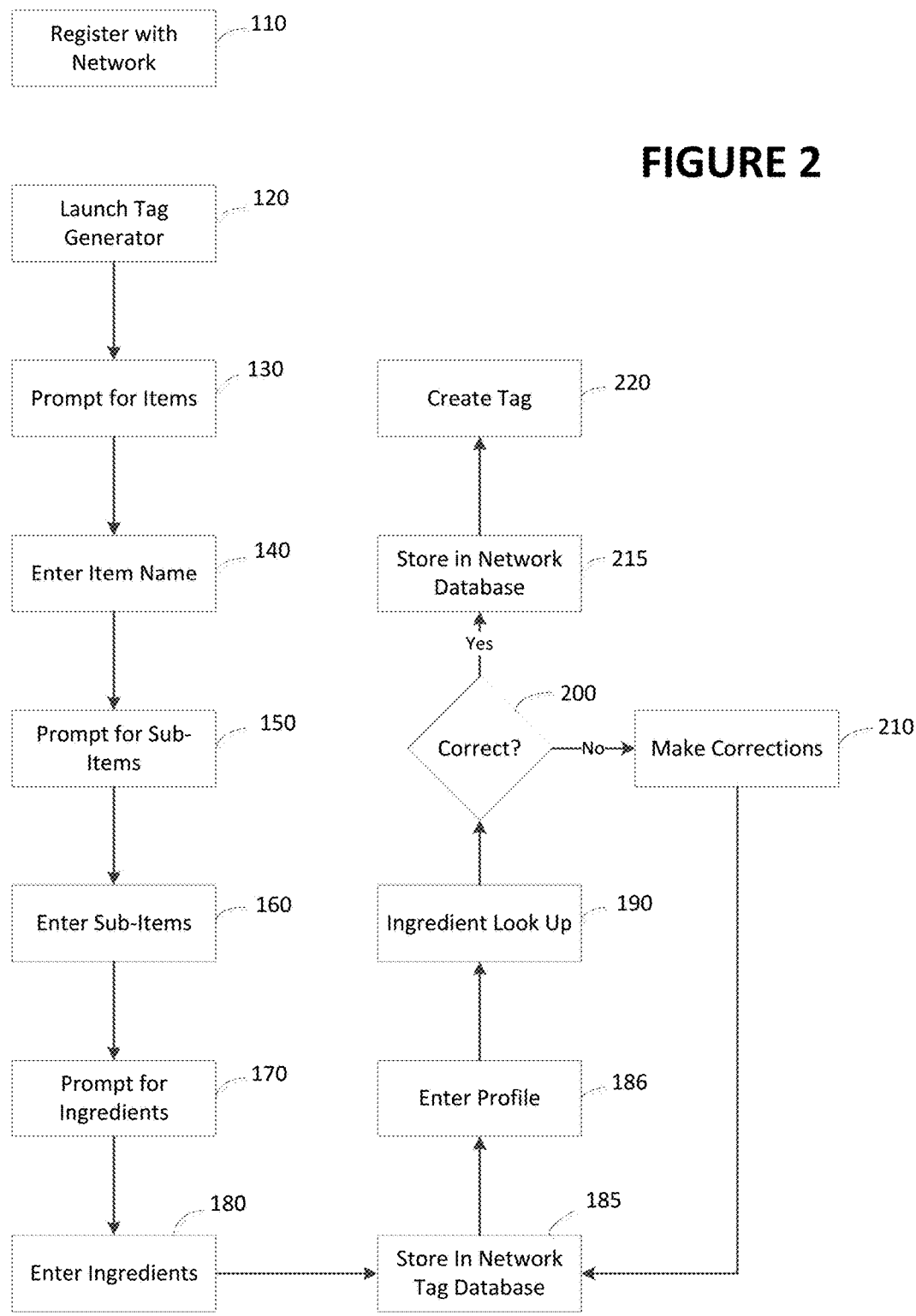
FIG. 2 shows a process for generating a network tag according to one embodiment of the invention.

FIG. 2 shows a process for generating a network tag according to one embodiment of the present invention. A venue registers at 110 to become part of the network and receives a unique network ID. After registering the venue may initiate a tag generation application at 120. The tag generation application will prompt the venue to input a first item that the venue serves at 130. The item, for illustrative purposes only, is a prime rib dinner with prime rib, garlic mashed potatoes and seasonal vegetables. In response, the venue can input the name of the item "prime rib dinner" at 140. The application may also prompt the venue to input the sub-items that are served when a user orders the item at 150. (In this context, "sub-item" refers to each part of an item as it is served by a venue.) In this example, the venue would input prime rib, garlic mashed potatoes, and seasonal vegetables at 160. The application would further prompt the venue to enter the ingredients for each sub-item along with their respective quantity for the sub-items at 170. Continuing with the example, the venue could enter at 180:

8 oz of prime rib, 1 cup of garlic mashed potatoes comprising ½ potato, ¼ cup of skim milk, 2 garlic cloves, 2 tbsp of Acme brand butter, ⅛ tsp of salt and ⅛ tsp of pepper 1.5 cups of seasonal vegetables comprising ⅓ cup zucchini, ⅓ cup yellow squash, ⅓ cup red pepper, ½ cup chopped cauliflower, ½ tablespoon of oil, fresh rosemary Building the menu item can be implemented in a variety of ways and the invention is not limited to these precise steps.

A sample input screen illustrating steps 130 to 170 for the above example is shown in FIG. 3. As shown, the input screen in this example includes input fields for venue name, network ID, item number, item name, sub items, ingredients, amount, and units.

Returning to FIG. 2, the application will store the input information in the network tag database 25 in association with the venue's unique network ID at 185. The application may automatically look up basic nutrition and allergen information associated with the ingredients and the specific portions input or it may wait until prompted by the venue at 190. If the venue requests the look up, preferably the application permits the venue to specify a particular standard profile at 186. In a preferred embodiment, the application will display the nutritional and allergen information for each sub-item and the item so that the venue can assess if the information input was correct at 200. If the information is not correct, the venue may make any changes at 210. After any changes are made, the new item name, sub-item names, ingredients or quantities are stored in the network tag database overwriting the prior information at 185, and the ingredient look-up with the new information is performed at 190. Once the venue has entered the ingredients correctly, it may generate a tag at step 220. All of the ingredients will be stored in the network tag database 25 along with the corresponding items, sub-items, and venue unique network ID at 215.

Figure 4:
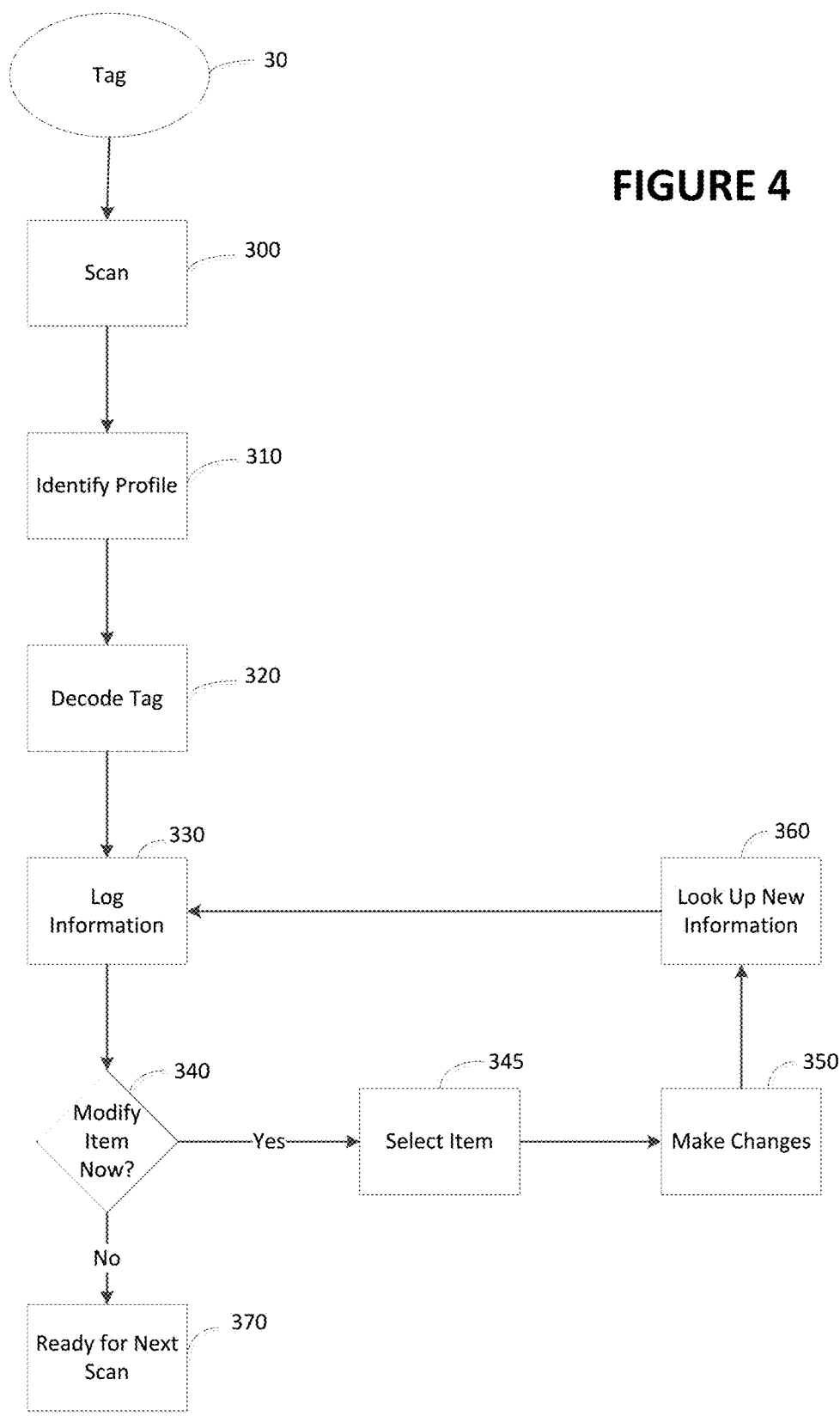
FIG. 4 shows a process for tracking and modifying items consumed.

A user may track the nutritional and other information pertaining to the items consumed according to the process shown in FIG. 4. The tag 30 preferably includes the nutritional and other information encoded in accordance with the predetermined profile entered at step 186 shown in FIG. 2. At 300 the user scans the encoded tag preferably using a tag reader 40 stored on a mobile device. The tag's profile is determined based on the header or other indicia at 310. The tag is then decoded in accordance with the identified profile at 320. The nutritional and other information resulting from the decoding step 320 is stored in the user's log 50 at 330 along with the venue's unique network ID and the item name. It should be understood that the tag itself may be stored immediately after scanning and decoded and logged in accordance with steps 320 and 330 at a later time. Such delay may be useful if the user intends to modify the portions or make substitutions as described below.

In one embodiment of the invention, the user can optionally modify an item that has been logged at step 330 as shown at step 340. If the user wishes to modify an item, for example by modifying a portion or by making a substitution, the user selects an item at 345. The selection step 345 may be implemented, by way of example only, by displaying a list of the user's logged items from which the user may electronically select one or more of the listed items, or the user could instead search for a specific item. It should be further understood that the number of items listed could be based on a variety of factors such as for illustrative purposes only the items logged in the past day. The user would select the item to be modified at 345 and would make the desired changes to the item at 350. The changes may be implemented in a variety of ways as is described below. Once the changes are made, a new look-up is performed in accordance with step 360.

In addition, the tag will preferably include a venue field with the unique network ID such that each venue that has registered to become part of the network has an individually unique ID. Since the network tag database 25 stores the amounts and ingredients for the various items, registered users and venues can access the database to "break it down" so that modifications can be made based on elimination of certain ingredients or decisions not to eat certain portions, e.g., only ate half the garlic mashed potatoes. It should be understood that if the network tag database 25 is secured with access only to registered users and venues, users and venues may only be given access to the item information in the user's own log or the items generated by the corresponding venue, respectively.

Figure 5A:
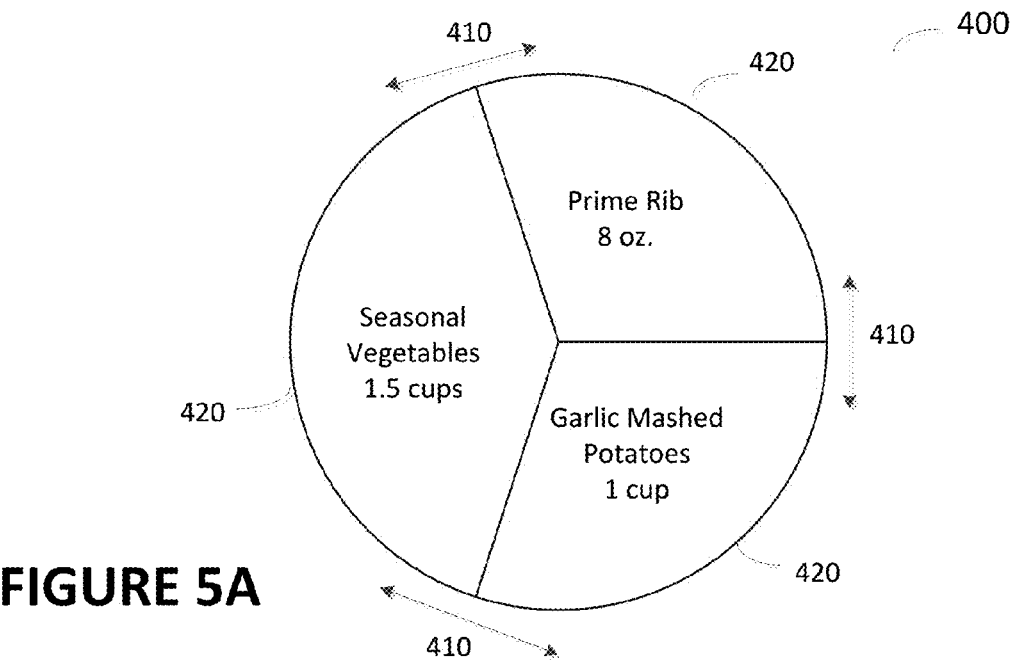
FIG. 5A shows an exemplary user interface that could be used by a user to proportion the sub-items according to the amounts the user actually consumed.

FIG. 5A shows an exemplary user interface that could be used to proportion the sub-items according to the amounts the user actually consumed. As shown in FIG. 5A there is a plate graphic 400 with the serving size portions of the sub-items as entered by the venue. Using the example above, 8 oz of prime rib, 1 cup of garlic mashed potatoes, and 1.5 cups of seasonal vegetables, the user may use graphical controls such as those shown at 410 to adjust the portions 420 of the sub-items.

Figure 5B:
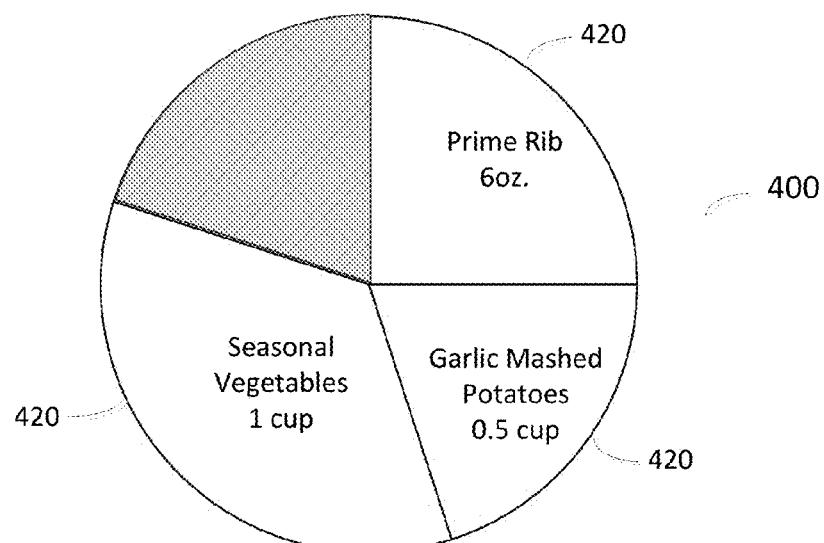
FIG. 5B shows the relative portions of sub-items changed in FIG. 5A.

In FIG. 5B the relative portions are preferably displayed at 420 along with the sub-item name given by the venue as adjustments are made with graphical controls 410. Once the user has adjusted the portions 420, the user can preferably indicate that the consumer log 50 should be updated with the new portion sizes and/or other information. The change module 60 will retrieve new values based on the modified ingredients or amounts and replace the corresponding values in the consumer log 50.

FIG. 5C shows an exemplary user interface that could be used by a user to substitute one sub-item for another. In this example, assume that the user wishes to substitute potato salad for garlic mashed potatoes. The user according to this example selects the garlic mashed potatoes as indicated at 440. The relevant sub-items that could be substituted could then be displayed, as shown for example at 450.

Figure 5D:
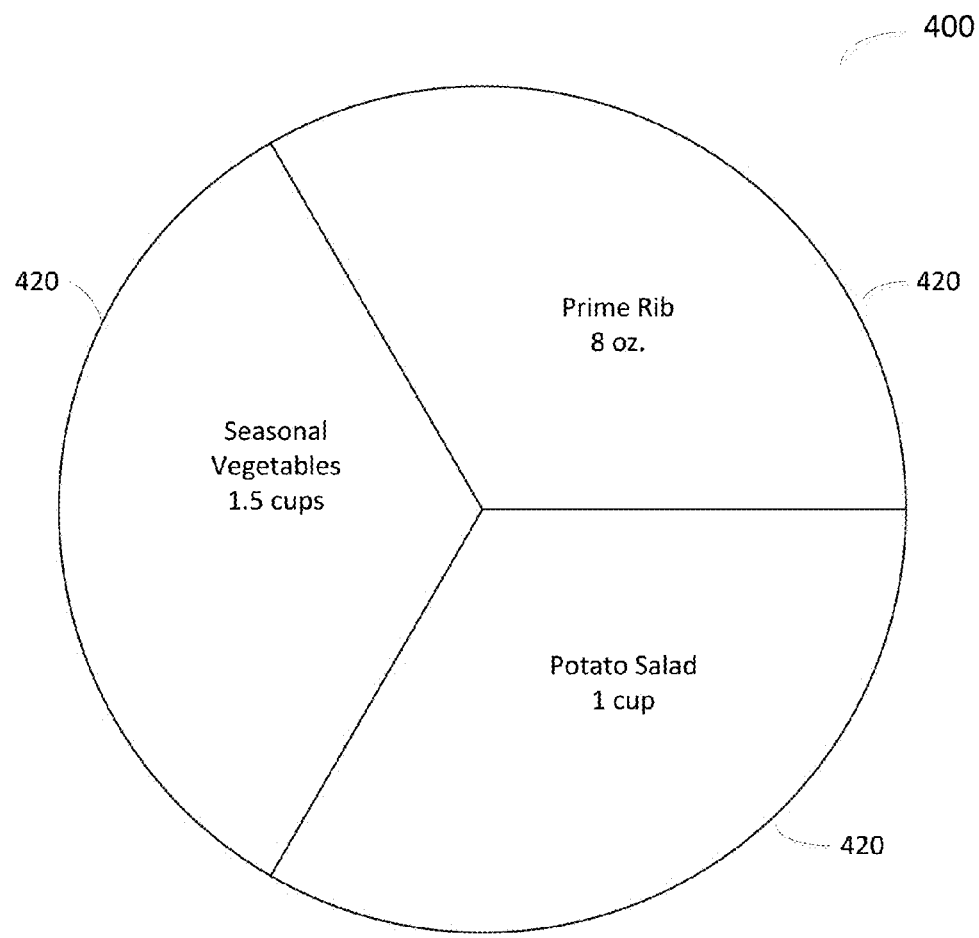
FIG. 5D shows a user interface that could be displayed after the user has indicated the desired substitution in FIG. 5C.

FIG. 5D shows a user interface that could be displayed after the user has indicated the desired substitution. There are other ways to implement portion controls and substitutions, as will be understood by those of skill in the art of user interface design.

Figure 5E:
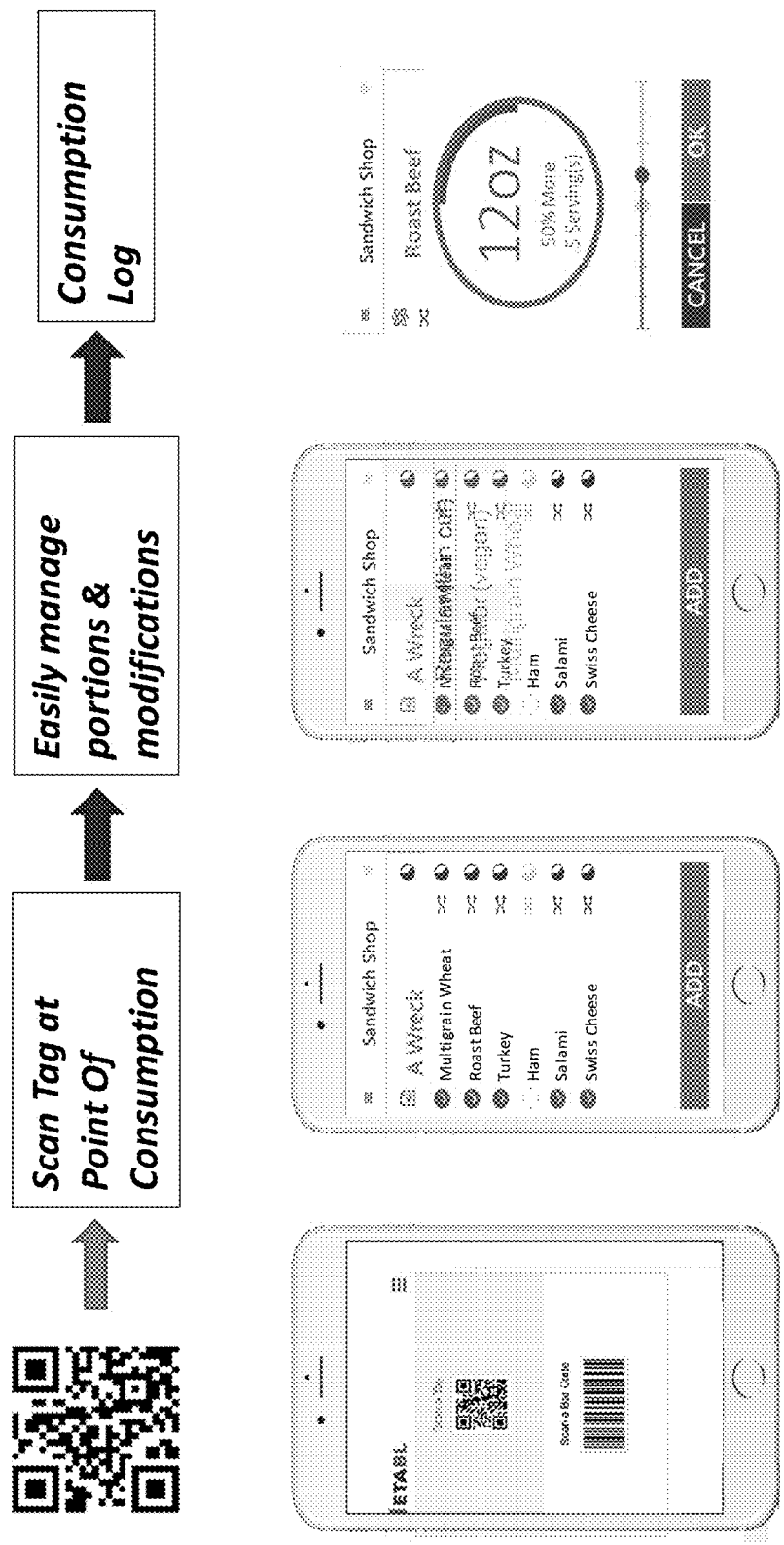
FIG. 5E shows additional user interface elements for implementing the modification features of the inventive system.

FIG. 5E shows additional user interface elements for implementing the modification features of the inventive system in a smartphone based app.

Figure 6:
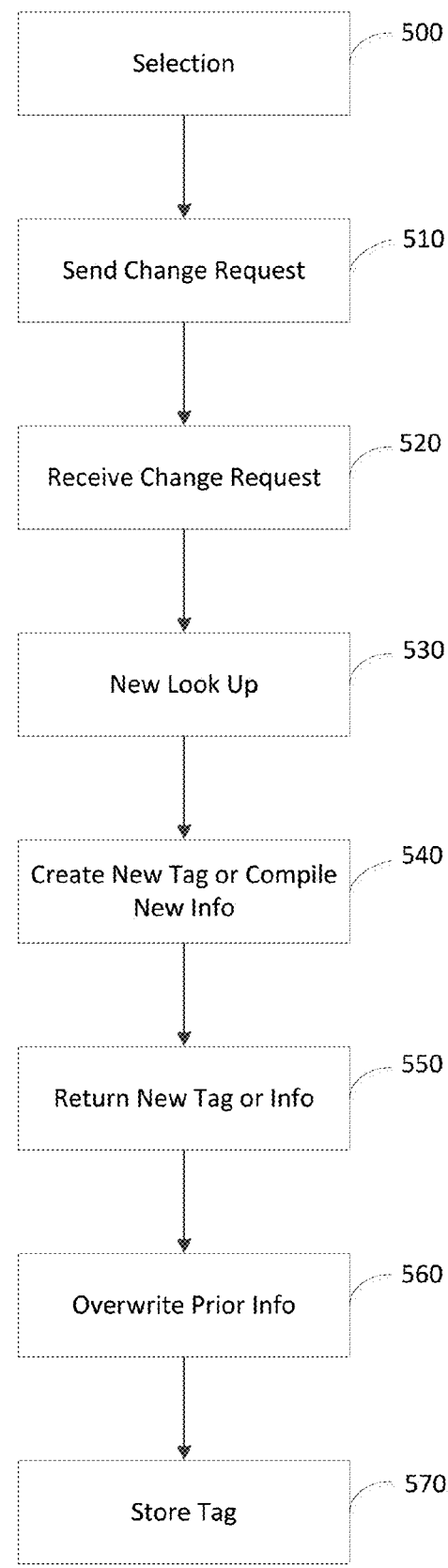
FIG. 6 shows an illustrative process for employing a network service provider in making changes.

In another embodiment of the invention, the user may wish to modify the logged info by requesting the modified information by, for example, sending a request to a network service provider and having the network service provider send back the modified information. FIG. 6 shows an illustrative process for this embodiment of the invention. A user scans a tag and then logs the decoded information as described above by way of example in connection with FIG. 4. The user selects the tagged information at step 500 and sends a message to a network service provider at step 510 describing the desired changes or substitutions. The selection step 500 may be implemented in numerous ways. For example, the user could select the venue network ID and the item information as stored in the user log. In another example, the user could select the tag itself as described above in connection with FIG. 2. The messaging step 510 may also be implemented in numerous ways. For example a text message could be generated including the selected information with the user's specified modifications or substitutions. Alternatively, the user could be prompted for the network ID and item name as well as the changes desired.

In FIG. 6, the message is received by the network service provider at step 520. The network service provider looks up the information associated with the venue unique network ID and item name from the network tag database 25 at step 530. The network service provider makes the requested portion changes and/or ingredient substitutions at step 540. The network service provider then sends a modified tag back to the user at step 550. The user, using its consumer application 65, replaces the information logged from the original tag with the information decoded from the new tag at step 560. The user may store the modified tag, corresponding recipe or menu item at 570 in one embodiment for later use when consuming the same modified item from the same venue.

In another embodiment of the invention, the user may be notified of items the user logged when visiting a particular venue again or when in the vicinity of the same venue. For example, if a user purchased a ham and cheese sandwich on whole grain bread with mustard at the Ma & Pop's corner deli, the user application 65 can be set to check for prior items consumed at the venue.

Figure 7A:
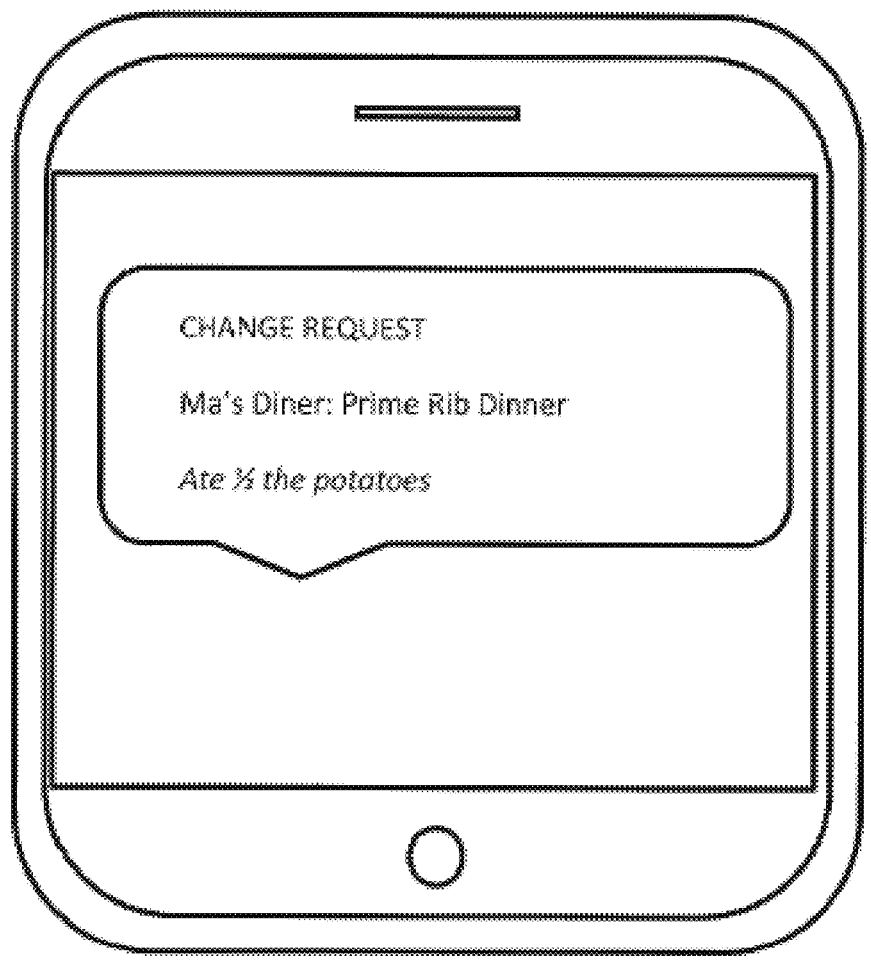
FIG. 7A shows an exemplary message for requesting a change.

FIG. 7A shows an exemplary message and FIG. 7B shows an exemplary user interface populated pursuant to steps 500 and 510. It should also be understood, that the change request could also be made by a venue's POS terminal based on the user's specific order and submitted from the POS terminal to the network service provider directly. The change request could direct the network service provider to modify the tag and return it to the POS terminal to be printed on a receipt or wirelessly transferred to the user, returned directly to the user for the user to log, or could enter the relevant information directly into the user's log. It should be understood that the above examples are for illustrative purposes only and are not intended to limit the invention.

Figure 8:
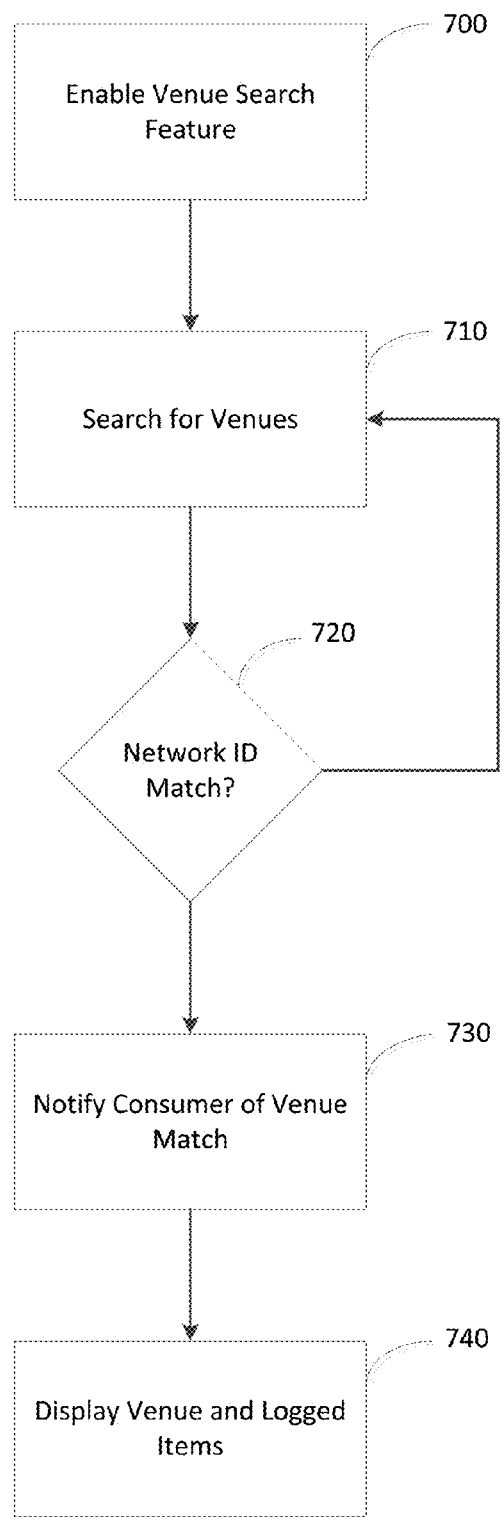
FIG. 8 shows a process for identifying registered venues located near a registered user.

FIG. 8 shows a process that could be implemented by the consumer application 65 to identify previous items consumed. The consumer application may optionally be set at step 700 to recognize venues where the user has previously consumed items. The consumer application will search for venue network IDs at step 710 as described below and determine at step 720 if a discovered venue network ID matches a venue network ID stored in the user's log. If there is a match, the consumer application will notify the user at step 730 and display the venue name and names of items consumed at step 740. In one embodiment of the invention, the consumer application will display any modifications or substitutions the user had made to the previous items consumed. If no match is determined at 720, the consumer application continues to search at 710 until a match is found. The search at step 720 may be implemented in many ways. For example, the consumer application 65 launched from a mobile device could connect to the venue's WiFi network. Once connected, the venue would provide the venue's network ID. As an example of a different approach, the mobile device could use the GPS or other location service or technique to identify the location of the user and then based on the location identify the venues close by that are registered with Network IDs. In this latter example, those skilled in the art would understand that the location of each registered venue desiring to participate in the search feature could be stored in association with the venue's unique network ID.

In another embodiment, a venue can register with multiple locations so that the consumer application could look up and display any previous items consumed at any of the venue's locations when determining that the user has entered the venue or is nearby any of the venue locations. Correspondingly, a user could select certain items in its log and initiate a search for the closest location for the associated venue. Venues with multiple locations would preferably indicate when generating tags for their respective items if certain items are only available at certain locations so that such information could be stored in the network tag database 25 (FIG. 1).

The consumer application 65 in one embodiment of the invention may also permit the user to select certain search criteria, such as for illustration purposes only, meals that meet certain dietary thresholds, e.g., 5 Weight Watchers® points or Zone® ratio meals. Alternatively, the consumer application could be programmed to monitor the user's consumption trends. For example, every weekday the user eats lunch out and typically orders a salad. If it is about the time of day when the user normally eats lunch, the consumer application in this embodiment would search for venues that serve salads and display the venue name, location and salads including the nutritional and other information associated with the salads. To provide another example, if a user typically consumes more protein, and presumably should consider finding a high protein meal, the consumer application may notify the user that he or she is low on protein and then search for venues that serve high protein meals displaying the venue names, locations and high protein meals with their associated nutritional information. It should be understood that venue locations for all of the above search scenarios may be shown by address or by map such as by interfacing with a common mapping application. It should further be understood that the foregoing examples are for illustrative purposes only and not intended to limit the invention.

Figure 9:
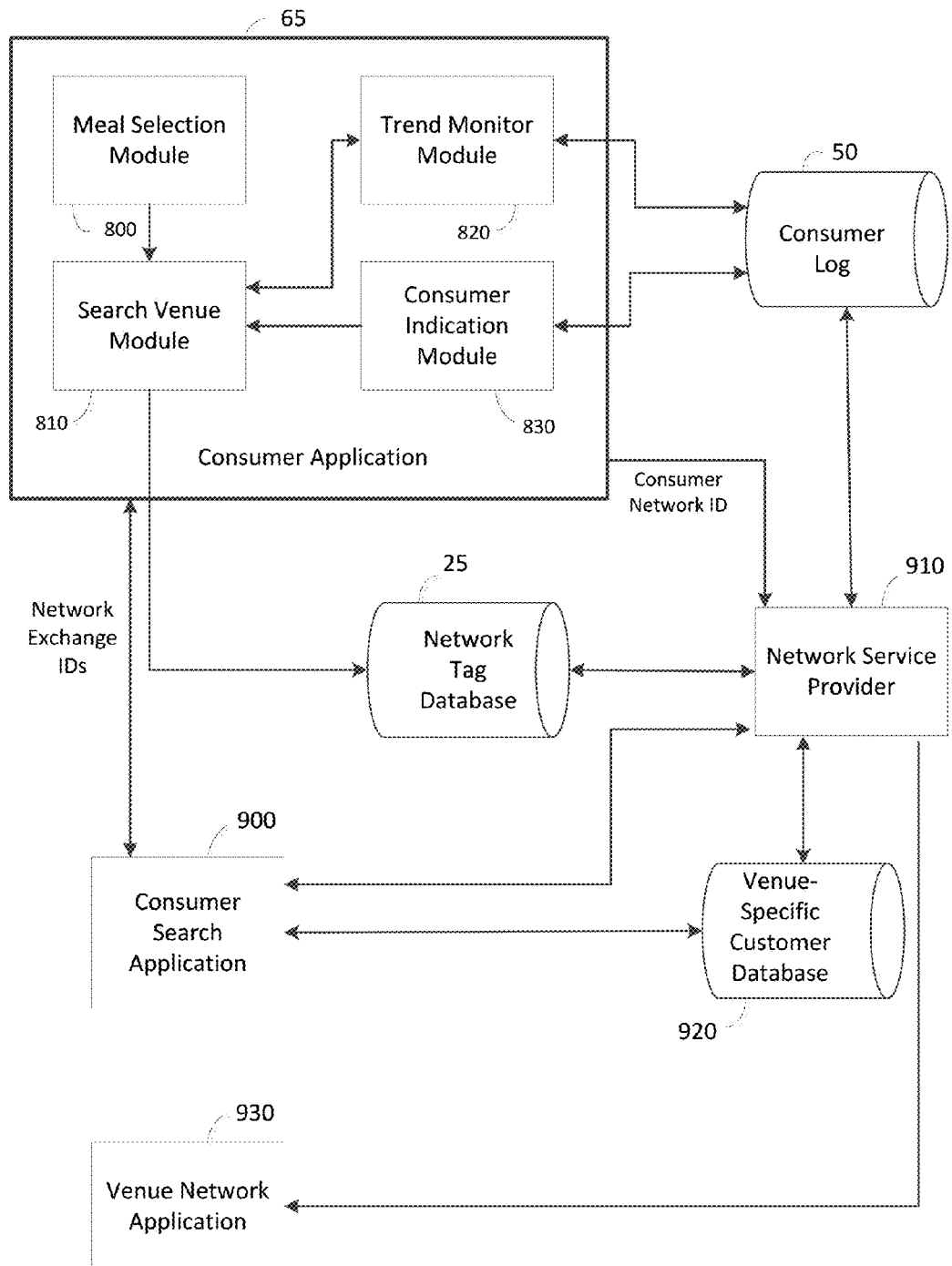
FIG. 9 shows an exemplary implementation of the user application, user search application and venue network application.

FIG. 9 shows among other features of the invention an exemplary implementation of the Search Venue Feature described above in connection with FIG. 8. The consumer application 65 according to this aspect of the invention comprises a meal selection module 800. According to this aspect of the invention, a user interfaces with the meal selection criteria to set search criteria as discussed above, e.g., 5 Weight Watchers® points or Zone® ratio meals, or other criteria. The search criteria are provided by the meal selection module 800 to the Search Venue Module 810. The Search Venue Module 810 searches the network tag database 25 for registered venues proximate to the user as described above that serves items that meet the specified criteria. According to another embodiment of the invention, the user may enable the trend monitor module 820, which monitors the consumer log 50, to detect trends such as whether the user's current diet is low on protein or some other nutrient or if the user might be looking for a venue to purchase a salad as is typical for that user at that time of day. It should be understood that there are numerous other specific search criteria a user may wish to specify or different trends that could be monitored according to the invention. The criteria and trends described above are for illustrative purposes only and the invention is not intended to be limited to these criteria or trends.

In another embodiment of the invention, the consumer log 50 stores the time of day when an item is consumed. The time may be stored automatically when the tag is decoded and logged or it may be entered manually by the user. The consumer application 65 may preferably include a consumer indication module 830 enabling the user to input various indications reflecting the user's health, wellness or overall subjective feelings or mood. For example, the user may input that he or she feels tired, bloated, or anxious, or that he or she is nauseas or has a headache. These indications along with the time of day may be recorded in the consumer log 50. The trend monitor module 830 could be programmed to search consumer log for 50 for nutrition, allergen, or other factors such as time between meals that might have a correlation to one or more of the user input indications. If a correlation is detected by the consumer indication module 830 that is based on a dietary deficiency, the consumer indication module 830 could signal the search venue module 810 to initiate a search for a registered venue that serves items that would fill the dietary deficiency identified by the consumer indication module 830.

As discussed previously, a user, like a venue, may be requested to register with the network service provider 910. The user, like the venue, would also receive a unique user network ID associated with being a user. FIG. 7B shows a user interface displaying some of the registration data that may be requested and assigned to each new user registrant. In one embodiment of the invention, a registered venue could search for registered users using a Consumer Search Application 900 shown in FIG. 9. When a user enters the venue and connects to the venue's WiFi network, the WiFi network could request the user's network ID. The venue could then send that user messages either through the venue's web portal or via the network service provider 910 (e.g., by text message discussed above) about specials or other information that venue may consider of interest to the user. The Consumer Search Application 900 may also search for registered users through the network service provider 910, which could by way of example only, use a GPS or other location service to track registered users. The venue could use its Consumer Search Application 900 to set up messages to be sent directly to registered users that are in the venue's vicinity. When the network service provider 910 identifies a registered user in that venue's specified vicinity, it can deliver messages about specials or new menu items for illustration purposes only, to that registered user.

In one embodiment of the invention, the consumer log 50 is accessible only by the user irrespective of whether the consumer log is stored on the user's device and/or remotely, i.e., on a cloud server. In another embodiment of the invention, the consumer log 50 and the network tag database 25 are managed by the network service provider 910. In this embodiment of the invention, the network service provider could provide a venue, in a variety of ways, the items logged by users that the user purchased from that venue. Data such as the user's network id, the item consumed, any modifications that were made to the portion size or substitutions, any profile preferences, and the date and time such item was purchased along with any other relevant information of interest that is trackable could be provided to such venue. FIG. 9 shows a venue-specific customer log 920 representing the data associated with each venue's specific customers that could be generated by the network service provider 910.

In another embodiment of the invention, a venue could search for registered users that have also been customers of such venue. The network service provider 910 could provide information in the venue-specific customer log 920 to the Consumer Search Application 900. The venue using the Consumer Search Application 900 could evaluate the customer's specific purchases or trends related to that venue and send messages to the customer as discussed above when the customer enters the venue or is nearby. In addition to messages discussed above, the venue could use more targeted messages such as providing discounts for items that the customer previously purchased or propose that that the customer come in to purchase an item that, based on previous purchases, the customer may enjoy.

It should be understood, that the network service provider 910 may provide any trend information to any venue and enable the venue to message the user irrespective of whether or not the user is a customer and whether or not the message is based on a user trend, indication, specified criteria or some other criteria or preference.

In another embodiment of the invention, venues can utilize a network service provider 910 to evaluate the venue's customer purchases and make suggestions about when to buy new supplies or when to have specials to encourage sales of perishable foods. According to this embodiment, the network service provider 910 could evaluate all of the venue-specific customer logs 920 over a period of time that could be pre-programmed or specified by the venue and tabulate items and sub-items purchased or consumed during that applicable time period. The network service provider 910 could identify those items or sub-items purchased the most and send a message to the venue network application 930 to check to see if it needs to order more of the item or sub-item. Conversely the network service provider 910 could identify those items or sub-items that were purchased the least over the applicable period of time and identify any perishable items so identified and send a message to the venue network application to sell the perishable items before they go bad. It should be understood that the data stored in the venue-specific user logs 920 could be evaluated for a variety of different reasons, and consequently different types of messages could be generated and transmitted to the venue network application 930. For example, a message alert stating: "No one has bought ham for 1 week. Run a special to sell it before it goes bad to avoid having to dispose of bad ham." Or as another example, sending a message stating: "Many customers are substituting brown rice for white rice, do you need to order more brown rice?" Other important information can be ascertained from the consumption data, such as customers are not eating their pickles, so the venue should only include pickles if requested. It should be understood that these examples are for illustrative purposes and not intended to limit this feature of the invention.

In another embodiment of the invention, a registered venue could offer a loyalty program to its customers that are network registered users. For example, suppose a venue wants to offer a free dessert after the purchase of 5 meals. The venue could use the tag generator application 10 in FIG. 1 to input the details of the loyalty program and the network service provider 910 in FIG. 9 could, based on purchases made by users and tracked in the venue-specific consumer database 920, implement the loyalty program.

Figure 10:
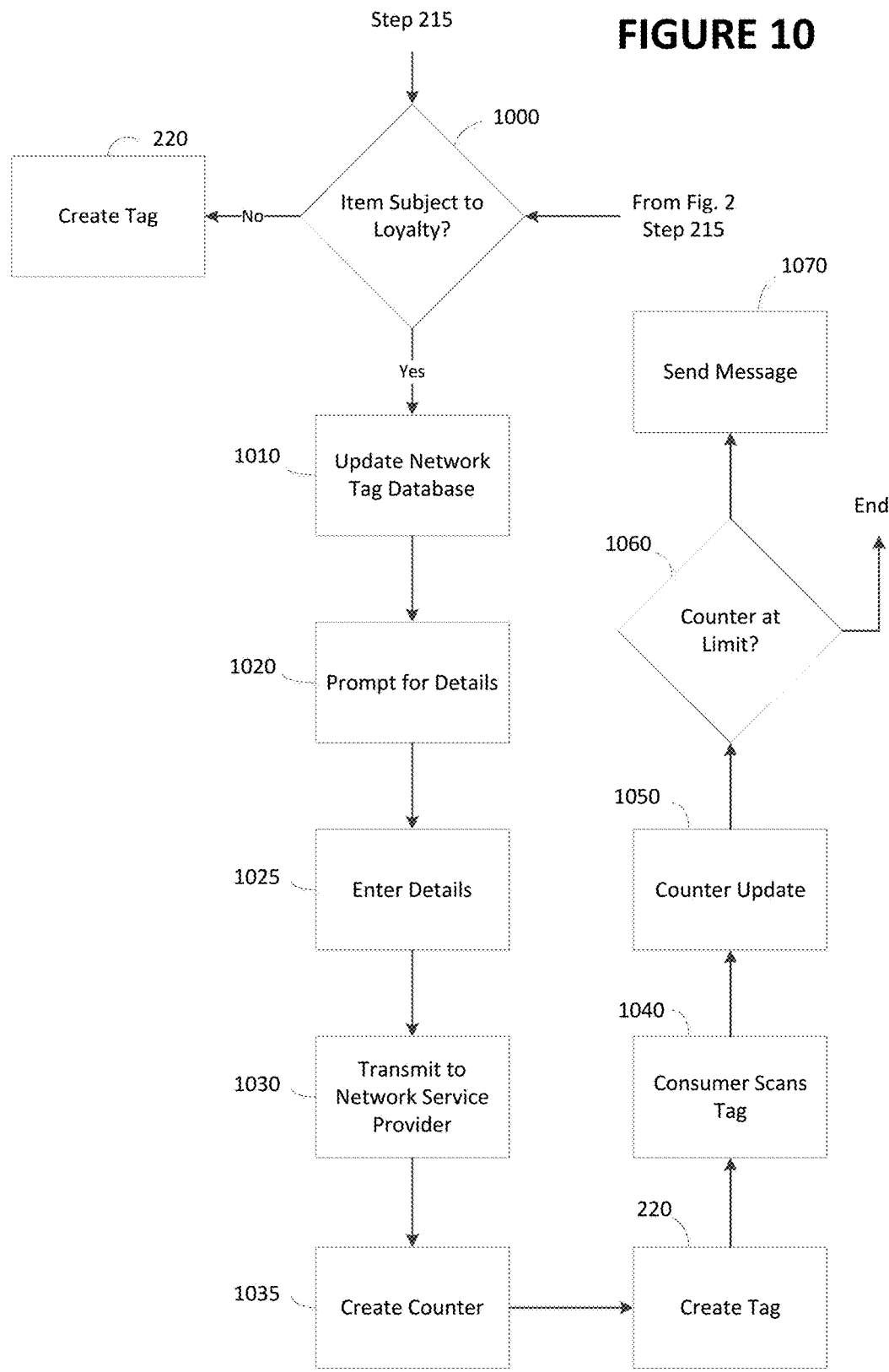
FIG. 10 shows an exemplary process for implementing a loyalty program.

FIG. 10 shows an exemplary process for implementing a loyalty program. After the tag generator application has stored the relevant nutritional and other information for an item in the network tag database (step 215 in FIG. 2), the tag generator application will query the venue at 1000 to indicate whether or not the item is subject to a loyalty program. If the venue indicates that the item is not subject to a loyalty program, the tag generation application 10 enables the venue to create a tag (step 220 in FIG. 2). If the venue indicates at step 1000 that the item is subject to a loyalty program, the tag generation application will populate a field associated with the item in the network tag database at step 1010 indicating that the item is subject to a loyalty program. The tag generation application then prompts the venue at step 1020 to enter the details of the program. For example, the tag generation application 25 could provide a list of different types of loyalty programs for the venue to select from. In this example, the type of loyalty program could be described as "Free after number of purchases." The venue would select that option at step 1025 according to this example. Continuing with this example, the venue could then be prompted to specify the number of purchases and any other item that may be included in the count. In this example, the venue could also be prompted to specify the items that may be purchased for free once the count is achieved. The venue would respond with 5 purchases, indicate the meals that should be counted, and the desserts that can be selected as free at step 1025 in accordance with this example.

In one embodiment of the invention, the information provided by the venue at steps 1010 and 1025 is transmitted to the network service provider at step 1030. The network service provider registers the loyalty program at step 1030 and creates a tag at step 220 with a field indicating that the item is associated with the loyalty program. At step 1035, the network service provider initiates a counter associated with the registered venue. When a registered user scans the tag for an item at step 1040, and stores the information in the user's log (as described above), the network service provider could update a counter at step 1050 for that registered user. The network service provider could store the updated counter in the user log or the venue-specific customer database or both. The network service provider then checks the counter at step 1060 against the limit set by the venue when inputting the details of the loyalty program at step 1040 and sends a message at 1070 to the venue, customer or both if the limit has been reached. In this example, the message could say "This customer has earned a free dessert" or "You are entitled to a free dessert." It should be understood that the message could be sent by text, pop-up message through the relevant applications, or other suitable means. It should further be understood that the counter could be implemented within the venue's POS terminal and connected computing devices or within the consumer application for each customer. This example is described for illustrative purposes only and is not intended to limit the invention to the example or the implementation described.

Figure 11:
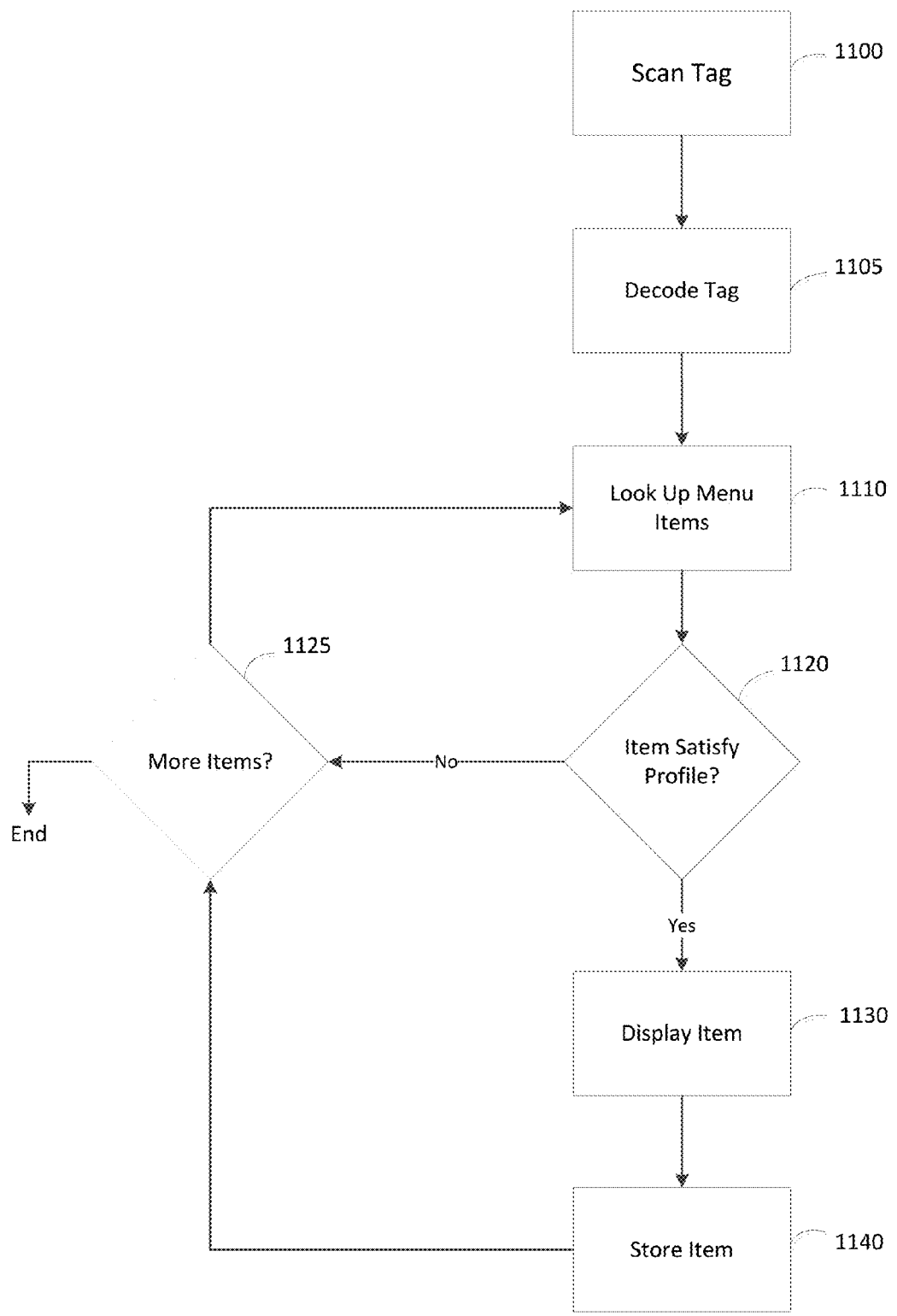
FIG. 11 shows an illustrative process for scanning a venue-unique tag.

Embodiments of the present invention enable a user to scan a venue-unique tag to identify only those items that satisfy the user's profile or other preferences. For example, if a user is allergic to dairy products, the consumer application would identify those menu items available from the venue that are dairy-free. FIG. 11 shows an illustrative process for this embodiment. At 1100, the user using tag reader 90 scans a venue-unique tag. The venue unique tag may include only the unique venue network ID. It should be understood that other fields may be included, for example, the venue's website, information about specials, new menu items, loyalty program information, etc. The tag reader 90, according to this embodiment of the invention, decodes the venue unique tag to identify the venue network ID at 1105. The consumer application 65 when connected with the network tag database 25 uses the venue network ID to look up each item served by that venue at step 1110. The consumer application compares each item to the user's profile preferences at step 1120. If an item matches the user's profile preferences, e.g., dairy free, then it displays the item at step 1130. If the item is not a match at step 1120, the next item if there are more as determined at step 1125 is looked up at 1110 and compared to the user's profile preferences at 1120. It should be understood that the matching items may be displayed at step 1130 on the user's device or stored at step 1140 on the user's device or in connection with the user log, or both.

The user may also use the downloaded items and sub-items to modify a scanned tag or logged entry as discussed above in connection with FIG. 4 and FIGS. 5A through 5D. The user may use his or her consumer application 65 to download the menu items and sub-items as described above. Or alternatively, the consumer application 65 could search for venues as described above (see search venue step 710 of FIG. 8). Once the venue unique network ID is obtained, the items and sub-items served by that venue stored in the network tag database 25 may be downloaded to the user's device. It should be understood that there are a variety of ways to implement a loyalty program with regard to registered venues and/or registered users, which may include, for example, storing the data locally at the venue so that the venue can direct that data to registered users, or users could download the venue information at any time from a list of registered venues.

Nutritional Tag

A presently preferred implementation of the nutritional tag 100 is described in detail in U.S. application Ser. No. 14/766,866. Moreover, the invention may be implemented using other coding structures, such as QR codes as discussed below and in U.S. Provisional Application No. 62/293,230 and U.S. Provisional Patent Application No. 62/334,078.

Figure 11A:
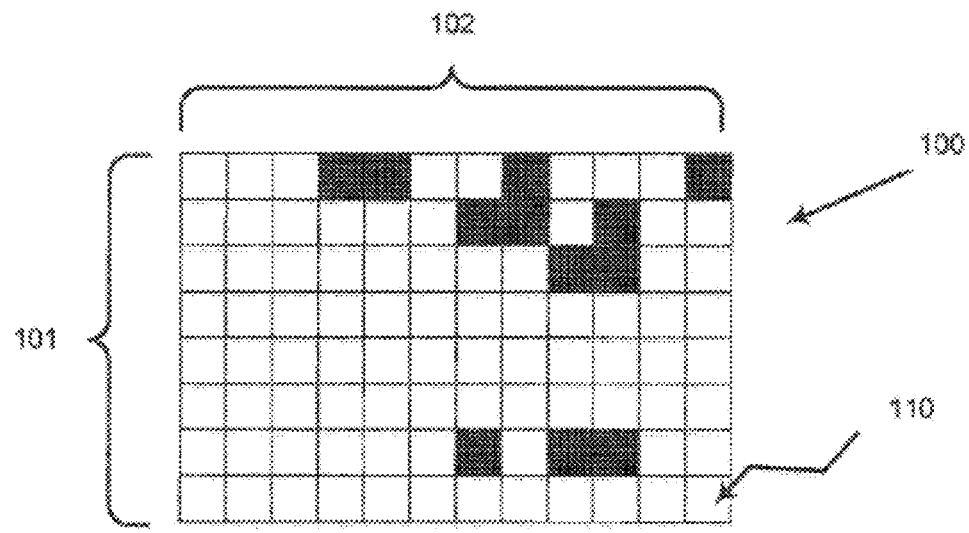
FIGS. 11A-11K schematically depict exemplary nutritional tags and various aspects thereof, including BCD coding, and headers and visual effects representative of a predetermined profile.

A nutritional tag 100 is shown in FIG. 11A. A plurality of rows 101 and columns 102 form a number of cells 110. The rows or columns form fields associated with a nutritional characteristic such as calories, fat, carbohydrates, vitamins or minerals. It should be understood that such fields may be representative of other ingestible substances such as allergens, drugs, chemicals and other ingredients that may be found in ingestible substances. The term nutritional characteristic is intended to include any such ingestible substances. Although the fields of tag 100 may be arranged by rows or columns, for purposes of simplified description, the fields may be described herein as arranged by rows only. The nutritional characteristics associated with each field will be ordered in accordance with a predetermined scheme. For illustrative purposes only, a standard could be developed to specify multiple profiles. In accordance with this example only, a first profile could specify the following:

TABLE 1

| Row 101 Number | Nutritional Field | Unit of Measurement |
|---|---|---|
| 1 | Calories | Calories |
| 2 | Calories From Fat | Calories |
| 3 | Total Fat | Grams |
| 4 | Saturated Fat | Grams |
| 5 | Trans Fat | Grams |
| 6 | Cholesterol | Milligrams |
| 7 | Sodium | Milligrams |
| 8 | Total Carbohydrates | Grams |
| 9 | Dietary Fiber | Grams |
| 10 | Sugars | Grams |
| 11 | Protein | Grams |

In this example, the tag 100 would comprise 11 rows 101 and each row would be coded in accordance with the value associated with a food, beverage or other ingestible substance. In a preferred embodiment the coding is represented in Binary Coded Decimal. However, those skilled in the art will recognize that other coding schemes are also suitable, such as binary, or 2D matrix bar codes such as Aztec and the like. The profile would also have a predetermined serving size associated with the nutritional information. The serving size could be a specific measure or amount such as 1 tablespoon, ½ cup, or 6 ounces. Alternatively, the serving size could be equivalent to a single serving as sold for prepared, packaged, or ordered products. It should be understood that that the serving size may also be encoded into the tag rather than associated in a predetermined manner with a particular profile. For illustrative purposes only, a serving of Ricotta cheese could be specified as ¼ of a cup and have the following values associated with the profile specified in Table 1 above.

TABLE 2

| Row 101 Number | Nutritional Field | Unit of Measurement | Value |
|---|---|---|---|
| 1 | Calories | Calories | 90 |
| 2 | Calories From Fat | Calories | 50 |
| 3 | Total Fat | Grams | 6 |
| 4 | Saturated Fat | Grams | 3.5 |
| 5 | Trans Fat | Grams | 0 |
| 6 | Cholesterol | Milligrams | 30 |
| 7 | Sodium | Milligrams | 85 |
| 8 | Total Carbohydrates | Grams | 4 |
| 9 | Dietary Fiber | Grams | 0 |
| 10 | Sugars | Grams | 3 |
| 11 | Protein | Grams | 6 |

Figure 11B:
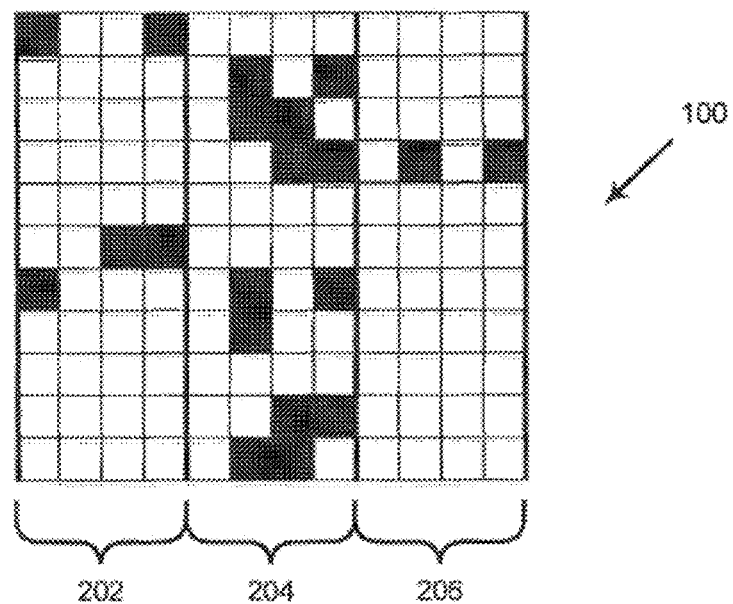

The tag 100 for the above example of Ricotta cheese using BCD coding is shown in FIG. 11B. In the same example, the first 4 columns 202 represent the 10 s digit of the value, the second 4 columns 204 represent the 1 s digit of the value and the third 4 columns 206 represent the first decimal of the value. The number of 4-column sections 202, 204 and 206 should also be predetermined for each profile and may vary based on the values expected to be coded, i.e., whether or not decimal places are represented and/or whether a 100 s or greater digits should be represented.

In a second profile according to the present example, the nutritional information may be extended as specified in Table 3 below.

TABLE 3

| Row 101 Number | Nutritional Field | Unit of Measurement |
|---|---|---|
| 1 | Calories | Calories |
| 2 | Calories From Fat | Calories |
| 3 | Total Fat | Grams |
| 4 | Saturated Fat | Grams |
| 5 | Trans Fat | Grams |
| 6 | Cholesterol | Milligrams |
| 7 | Sodium | Milligrams |
| 8 | Total Carbohydrates | Grams |
| 9 | Dietary Fiber | Grams |
| 10 | Sugars | Grams |
| 11 | Protein | Grams |
| 12 | Vitamin A | Percent of a 2,000 calorie diet |
| 13 | Calcium | Percent of a 2,000 calorie diet |
| 14 | Vitamin C | Percent of a 2,000 calorie diet |
| 15 | Iron | Percent of a 2,000 calorie diet |

For a serving of ricotta cheese, the values associated with the extended profile are listed in Table 4.

TABLE 4

| Row 101 Number | Nutritional Field | Unit of Measurement | Value |
|---|---|---|---|
| 1 | Calories | Calories | 90 |
| 2 | Calories From Fat | Calories | 50 |
| 3 | Total Fat | Grams | 6 |
| 4 | Saturated Fat | Grams | 3.5 |
| 5 | Trans Fat | Grams | 0 |
| 6 | Cholesterol | Milligrams | 30 |
| 7 | Sodium | Milligrams | 85 |
| 8 | Total Carbohydrates | Grams | 4 |
| 9 | Dietary Fiber | Grams | 0 |
| 10 | Sugars | Grams | 3 |
| 11 | Protein | Grams | 6 |
| 12 | Vitamin A | Percent of a 2,000 calorie diet | 4 |
| 13 | Calcium | Percent of a 2,000 calorie diet | 10 |

TABLE 4-continued

| Row 101 Number | Nutritional Field | Unit of Measurement | Value |
|---|---|---|---|
| 14 | Vitamin C | Percent of a 2,000 calorie diet | 0 |
| 15 | Iron | Percent of a 2,000 calorie diet | 0 |

Figure 11C:
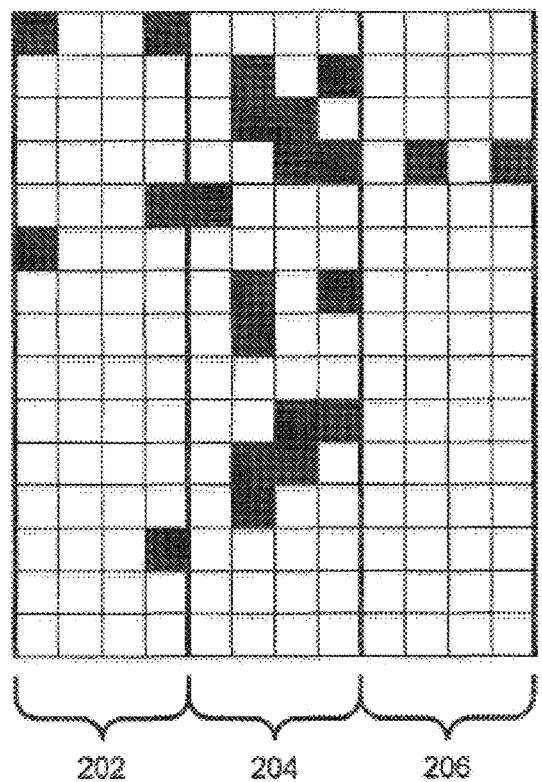
Figure 11D:
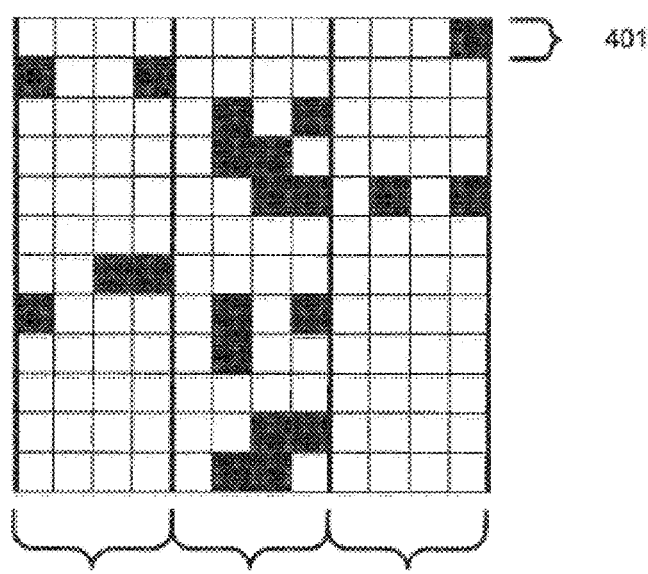
Figure 11E:
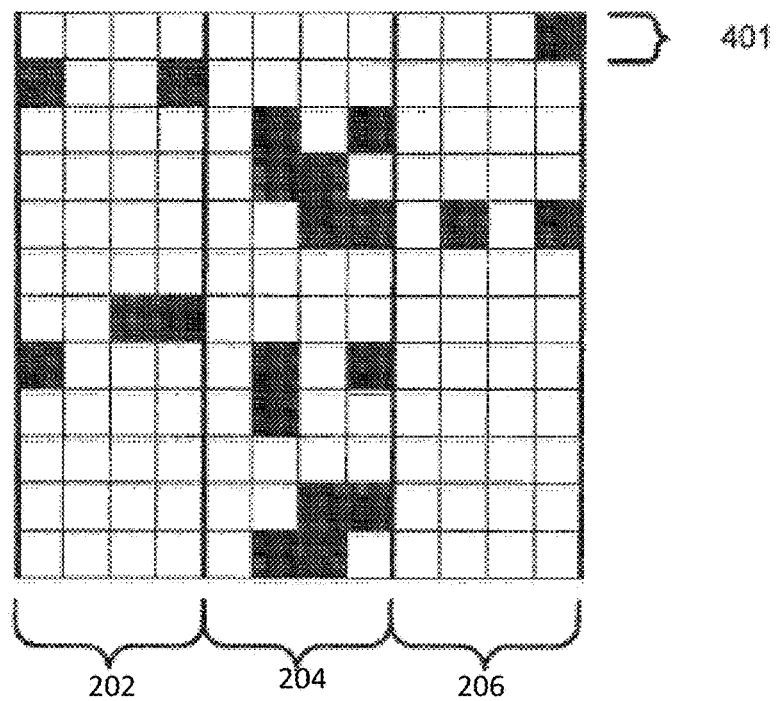
Figure 11F:
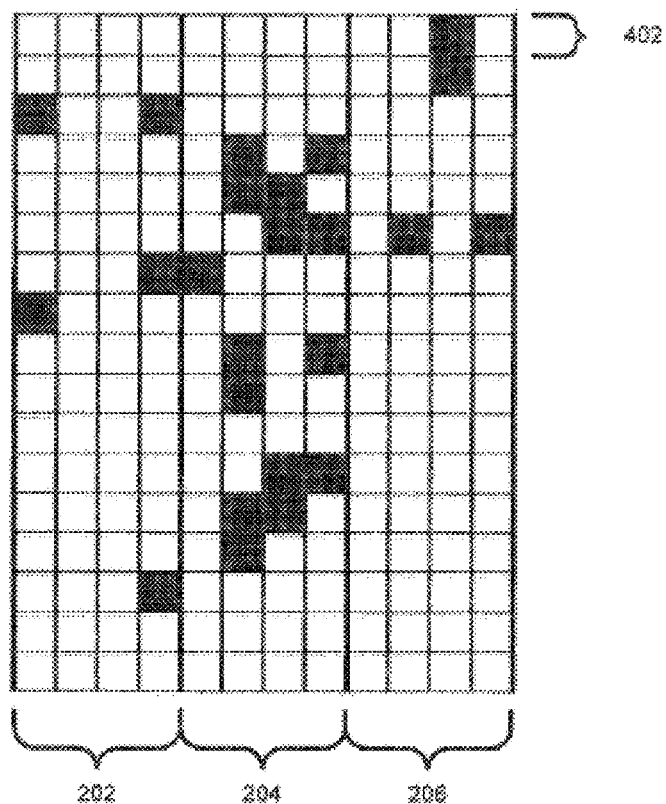

The tag 100 coded according to the extended profile for a serving of ricotta cheese is shown in FIG. 11C. Differentiation among profiles may be implemented in a variety of ways. One way would be to include a header in the same coding format that would specify the profile. For example, suppose the profile shown in Table 1 above is identified as Profile 1 and the profile shown in Table 3 above is identified as Profile 2. In the example where BCD coding is used, the servings of ricotta cheese with the values represented in Tables 2 and 4, respectively, would be shown in corresponding FIGS. 11D and 11E. Note that the first rows 401 in FIGS. 11D and 11E represent the header encoded with the applicable profile number. FIG. 11F shows the exemplary tag in FIG. 11C with additional rows 402 representative of the predetermined profile.

Figure 11G:
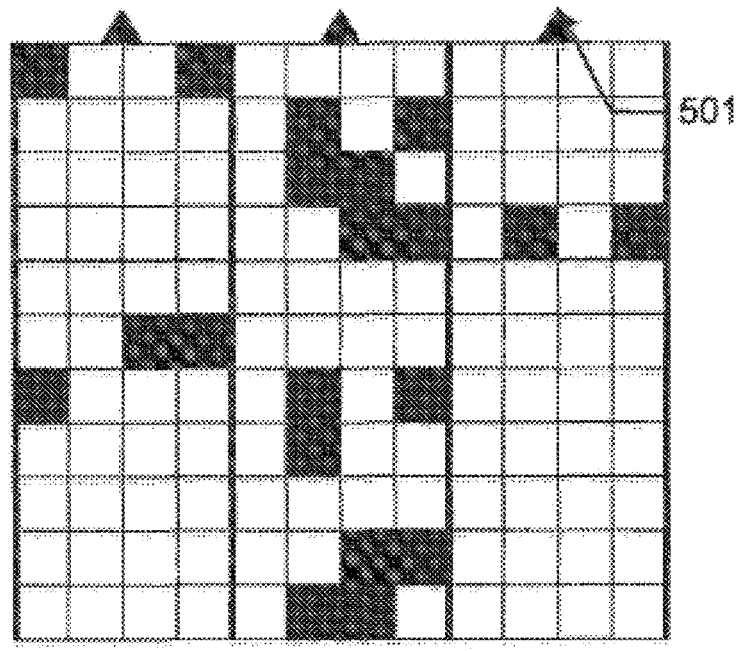
Figure 11H:
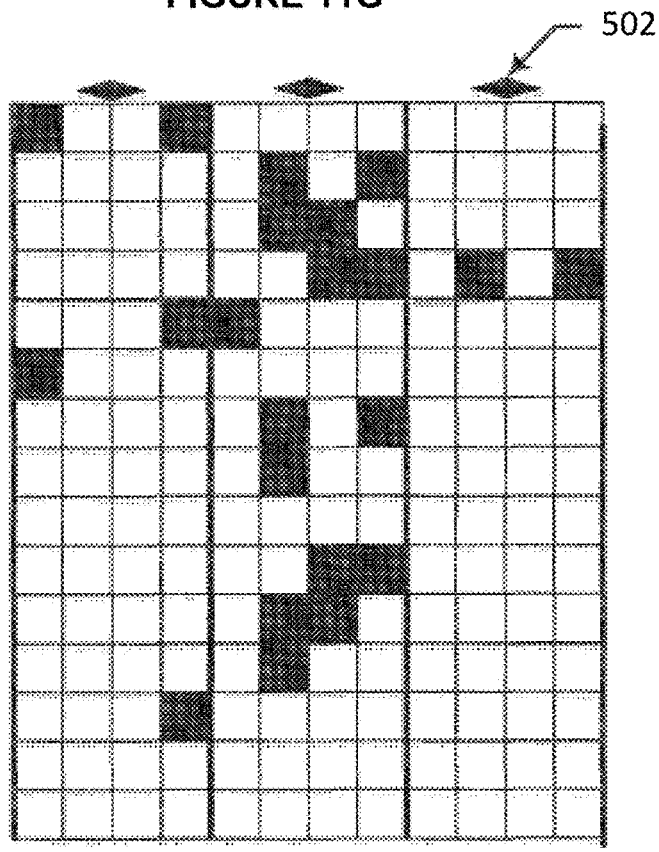

In an alternative embodiment, the profile identifier may be represented by visual or coded effects associated with the tag in a predetermined manner. For example, FIGS. 11G and 11H show Profiles 1 and 2 corresponding to a serving of ricotta cheese, respectively as described above using an exemplary visual effect. The small triangles 501 interspersed equidistantly across the top of the tag 100 in FIG. 11G is a possible predetermined way to identify Profile 1 and the small diamonds 502 interspersed equidistantly across the top of tag 100 in FIG. 11H is a possible predetermined way to identify Profile 2. It should be understood that many other effects are possible including but not limited to different designs, shapes, coloring of the cells, border designs and the like.

It should also be understood that some profiles may take advantage of both a header and a visual or coded effect to identify the profile represented. For example, a standard for all nutritional information could be created where the nutritional information would be listed in a predetermined order corresponding to a row number in a given tag. In creating the tag, only those rows to be tracked are included in the tag. The header for such tag would include a list of the row numbers corresponding to the nutritional information included in the tag. For instance, if an individual was interested in tracking only his niacin, calcium and Vitamin D intake, and the rows corresponding to niacin, calcium and Vitamin D are 7, 12 and 16 out of a possible 56 total predetermined rows, then the header could be represented as 56 cells with the 7th, 12th and 16th cell marked. A profile could be defined for this type of tagging, i.e., a subset of the universal list and identified by a visual effect. FIG. 11H shows an example of a tag 100 according to the foregoing description of a blended header and visual effect to identify the profile and information included in the tag where the header 403 specifies that niacin 410, calcium 412 and Vitamin D 414 are included and visual effect 503 specifies the blended profile.

Figure 11I:
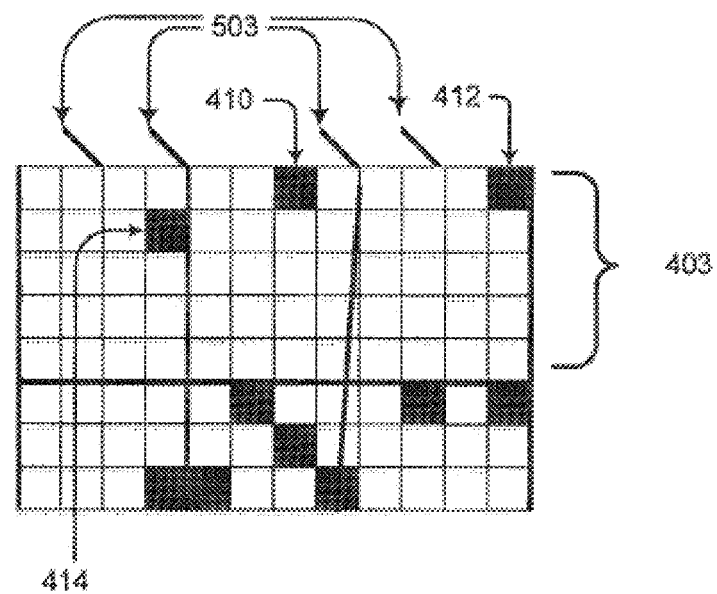
Figure 11J:
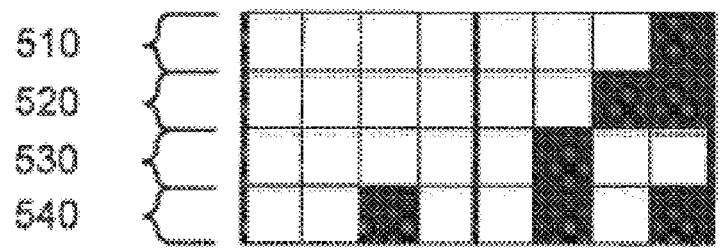

Many profile variations are also contemplated by the present invention such as drug directives, allergens, artificial substances and the like. For example, a profile could also be created that specifies allergens or other substances to be avoided that are present in a particular ingestible substance. FIG. 11I shows an exemplary tag having an allergen profile, and FIG. 11J shows an exemplary tag having a drug directive profile.

Table 5 shows an exemplary predetermined scheme for allergens and other substances that may be found in ingestible products that individuals may choose to avoid.

TABLE 5

| Row 101 number | Allergen |
|---|---|
| 1 | Gluten |
| 2 | Nuts |
| 3 | Dairy |
| 4 | Eggs |
| 5 | Aspartame |
| . . . | . . . |
| N | Caffeine |

The predetermined scheme may include N substances although very few ingestible substances would likely contain more than a fraction of such substances. Therefore, the tag associated with such a profile might include only the row numbers for those allergens or other substances that are present in a particular food. For example, a serving of chocolate cake may include gluten, dairy, eggs and caffeine. Assume for the purposes of this example that N=25. FIG. 11J shows a possible tag coded in BCD format for such a profile using the predetermined scheme in Table 5 for this serving of cake where the rows 510, 520, 530 and 540 represent the applicable row numbers in Table 5. Those skilled in the art will appreciate other methods of encoding such information are possible including the profiling and headers described above.

In the case of drug directives, a profile could be created for each drug with the relevant directives such as avoiding dairy or alcohol. Table 6 is an exemplary profile associated with drug directives.

TABLE 6

| Row 101 number | Drug Directives |
|---|---|
| 1 | Avoid Dairy |
| 2 | Avoid Excessive Sunlight |
| 3 | Avoid operating heavy machinery such as driving a vehicle |
| 4 | Take with plenty of water |
| 5 | Take with food |
| . . . | . . . |
| N | Avoid alcohol |

Figure 11K:
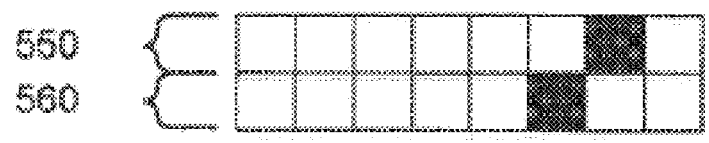
Figure 12:
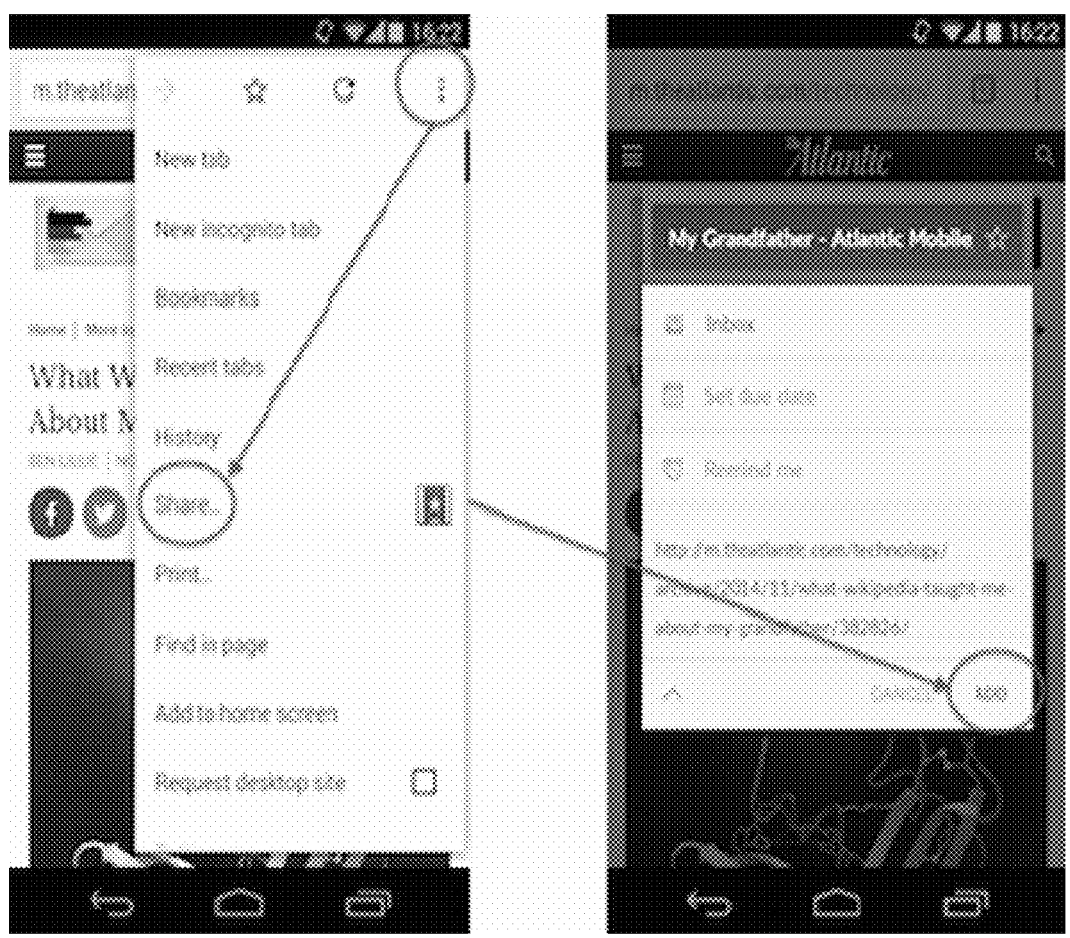
FIG. 12 depicts illustrative screenshots for importing a recipe using an embedded browser.

FIG. 11K shows an exemplary tag according to the profile shown in Table 6 for a hypothetical drug which should be taken with plenty of water and where the patient should avoid excessive sunlight. Using the same coding scheme as described above for the allergen profile, only the row numbers 2 and 4 would need to be represented in connection with this hypothetical drug. Assuming for this example that N=18 and BCD coding is used, FIG. 11K shows an exemplary tag for this drug directive profile for the same hypothetical drug. Row 550 represents the directive associated with avoiding excessive sunlight and row 560 represents the directive associated with taking the drug with plenty of water.

As noted above, the inventive system may be implemented using QR codes for the tags. As envisioned, the system would be configured to import the specific information for any food and encode the nutritional and allergen information into scannable tags. The scannable tags can be printed on menus, receipts, and signs, or even transmitted or displayed electronically. Users can then scan the tags using the inventive mobile app described below. Unlike the trackers and tools available today, the inventive system allows the user to select any of the ingredients and change its portion size, substitute it for something else and add other items that are available from the venue. Once those changes are made, the user needs but a single click to automatically populate the tracker with the relevant food data.

The tag itself is quite versatile and may be used in a variety of additional ways. For example, users could share tags with guests at a dinner party. Or the encoded information could be expanded to include other information, such as GMOs, artificial ingredients, or other data of interest. Data can be exported after it is scanned and logged to a different tracker. The encoded data can be used to provide users with personalized alerts, notices, and suggestions based on their personal targets and profile. Venues can use encoded fields to support promotions, loyalty programs and other marketing to the network of users. The tags can also be customized in a way that includes unique information types, such as "certified organic" or "IBUs" for beer.

There are dozens of recipe sites with thousands of recipes each. Some provide nutritional information that could be manually entered into a tracker but many do not. Most cooks, however, make modifications to the ingredients and amounts when preparing the actual recipe. As a result many recipes are followed by reviews with suggested changes. The inventive system could partner with a recipe site where the recipe ingredient lists are exported to the system. The system could then produce a tag and export it to the recipe site to include with a recipe. Cooks could scan the tag or click on a link to the system to make changes to the ingredients list to calculate the nutritional info based on those changes. If that cook left a review, the revised tag could be affixed to the review so that cooks making the same changes could simply scan the tag.

Most venues use a food service solution to maintain their inventory, point of sale, and recipe costing systems. Using these systems, venues know what they sell and how much of a margin they have per item sold but they cannot optimize if they don't know how much food their customers are actually consuming. The inventive system could import the recipe ingredient lists and generate tags for the venue. When the tags are scanned by the venues customers, the system could provide consumption reports, e.g., 80% of your customers don't eat the roll you include with their order, that would enable venues to optimize their margins.

The system could also import all of the items available at each station in a cafeteria and create a single tag. When the tag is scanned the customer can see the list of everything that is available and make his or her selections and portion size adjustments and then with a single click log the relevant nutrition info. Consumption data reports would be of use to the cafeteria as a means to avoid waste, e.g., determine what people are actually consuming to minimize waste.

II. Base Product, FIGS. 12-17R

Aspects of a base product are described in U.S. Provisional Patent Application No. 62/293,230, Feb. 9, 2016; U.S. Provisional Patent Application No. 62/293,709, Feb. 10, 2016; and U.S. Provisional Patent Application No. 62/334,078, May 10, 2016. Important aspects of the technology-based solutions described relate to the areas of information coding, user interfaces, data compression, and extensibility. The inventive solutions involve new, efficient ways of encoding information on both physical encoded tags/packaging as well as on digital storage media. The inventive system for producing electronically readable dietary tags solves the technical problem of optimally selecting, arranging, and displaying the nutritional information in the form of an encoded tag that can be physically associated with food items and also electronically read using optical imaging technology (such as a camera or bar code or QR code reader). The novel tag design improves the operational efficiency and effectiveness of the overall system itself, and it solves the technical problem of attaching the relevant nutritional information to the dietary products and transferring that information to users that purchase or consume the dietary products. Moreover, the coded information may be based on standardized or predetermined profiles so that the information actually encoded can be reduced and so that the codes can be designed with flexibility in mind. For example, one standardized profile could include just the essential nutritional information and allergens that are required by labeling laws on certain processed products ("Core Profile"). Another profile could include all the Core Profile information plus any artificial ingredients and/or GMOs. Other profiles could be adapted to include various vitamins, minerals or other substances of interest for certain diets or for certain health-related conditions. The size of the printed code will be important to ensure that it is large enough to be accurately scanned but not so large that it needs to take up too much real estate on the menus, receipts, packaging etc. Flexibility is also important not only for users who may be interested in different kinds of information but for venues and producers who may not be willing to adopt a system if certain information either must be included or excluded from the tags.

As discussed in the Background section above, several food trackers are now available enabling users to log dietary information relating to the foods/beverages consumed by such users. These food trackers are implemented as mobile apps with corresponding websites, e.g., MyFitnessPal, that enable users to access other dietary resources and information. The mobile apps provide a variety of tools, e.g. databases, barcode readers, etc., permitting users to obtain the dietary information they want to track. Only a small percentage of food as prepared for consumption, however, has been barcoded and the barcodes only identify the food product; a separate database needs to be created to store the nutritional info associated with the product. Databases have been created so that users can input each ingredient to compute cumulative dietary information such as the number of calories per meal but this look-up process is very time consuming and often inaccurate as the ingredients are not known to the user.

The present solution solves this problem by encoding each menu item's and sub-item's nutritional information into a tag that can be scanned directly by a user using a mobile app food tracker and logging the coded information into the user's daily food log. The user will be easily able to modify the portion size of each sub-item that is served with the item ordered, delete sub-items, add extras or make substitutions that can be ordered from the venue.

U.S. Provisional Patent Application No. 62/293,709 includes descriptions of the following aspects of the inventive system.

Figure 16A:
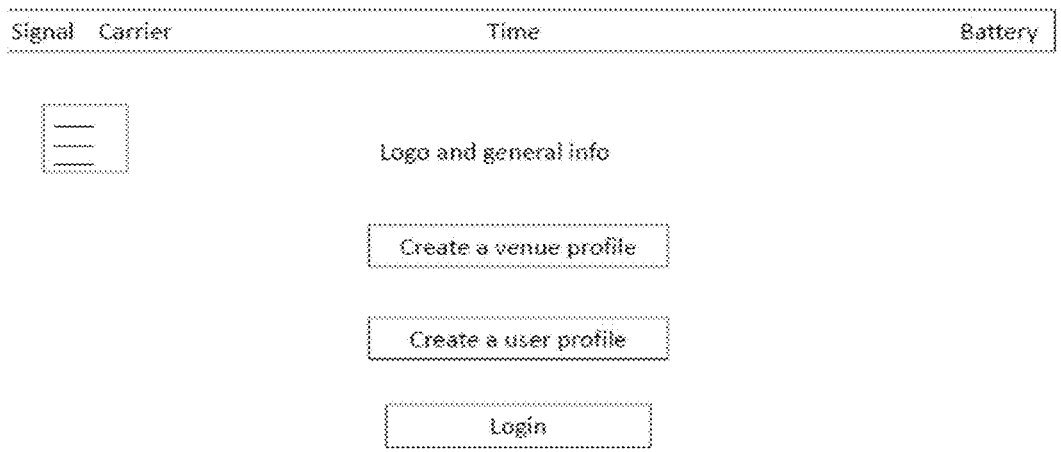
FIGS. 16A-Q depict illustrative mobile app wireframe diagrams depicting functional elements of a mobile app user interface.
Figure 16B:
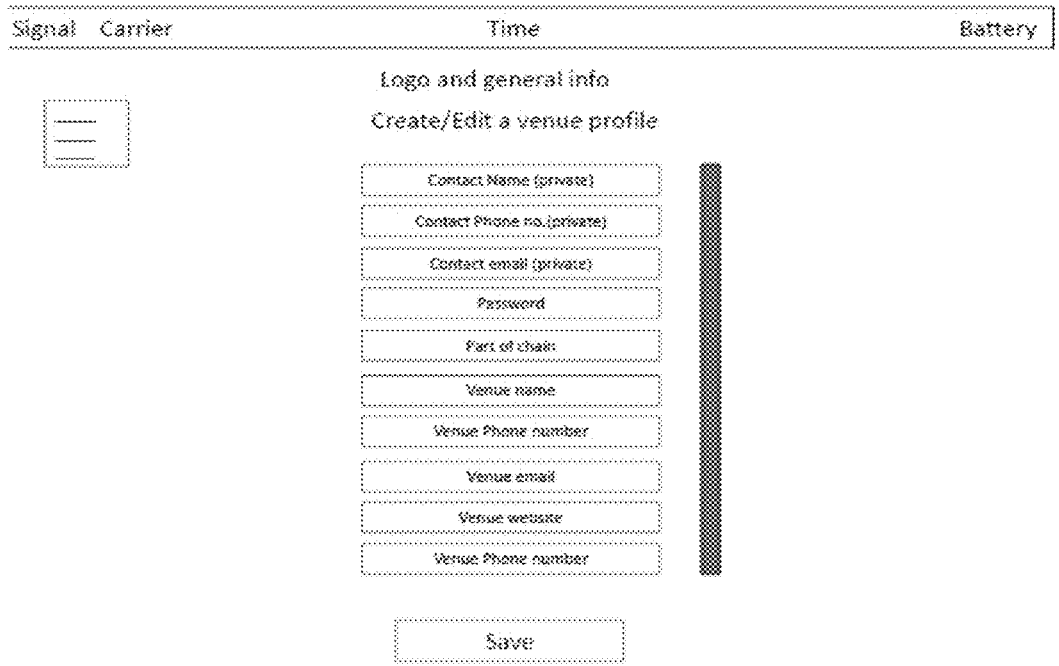
Figures 16C, 16D:
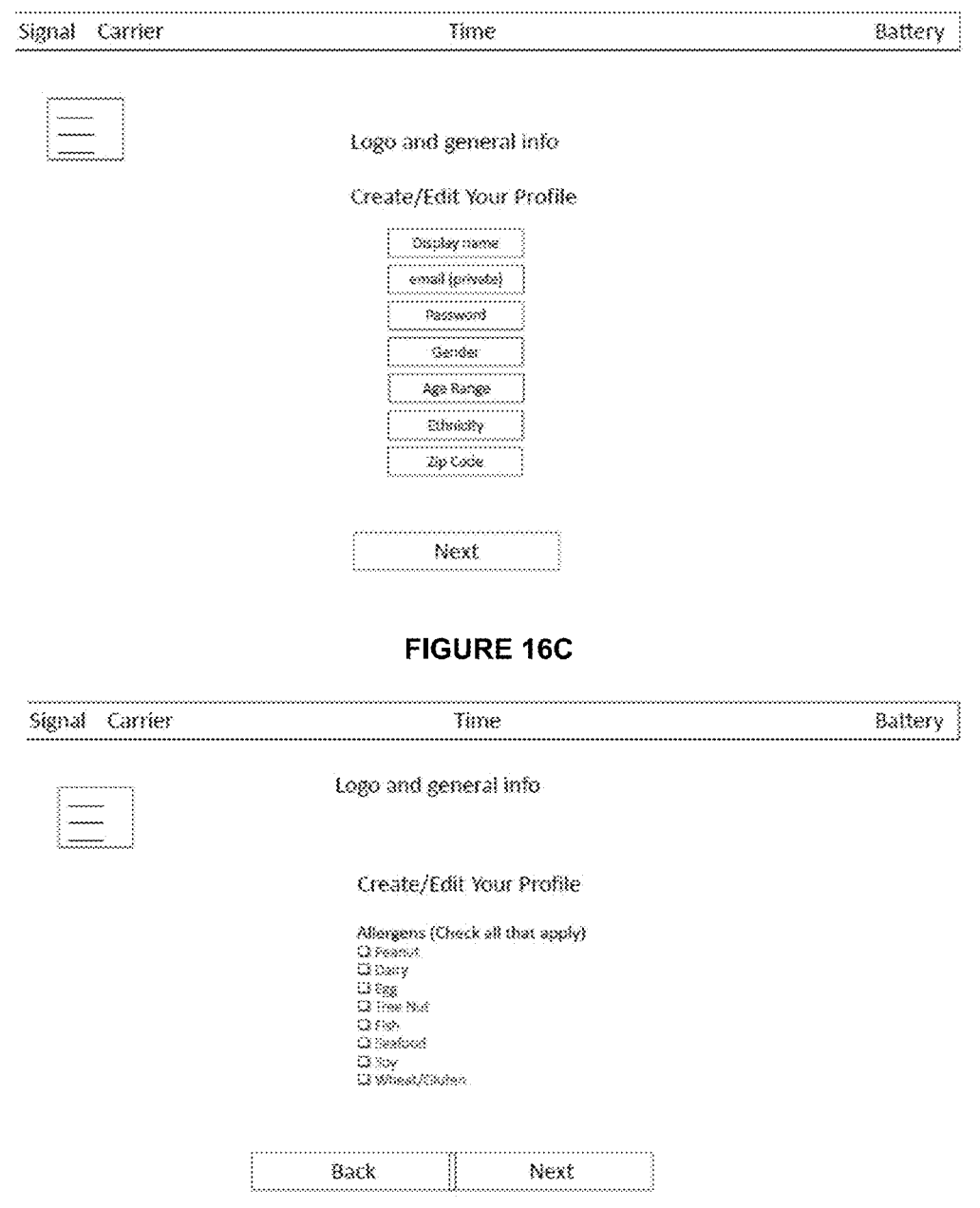
Figures 16E, 16F:
Figure 16G:
Figure 16H:
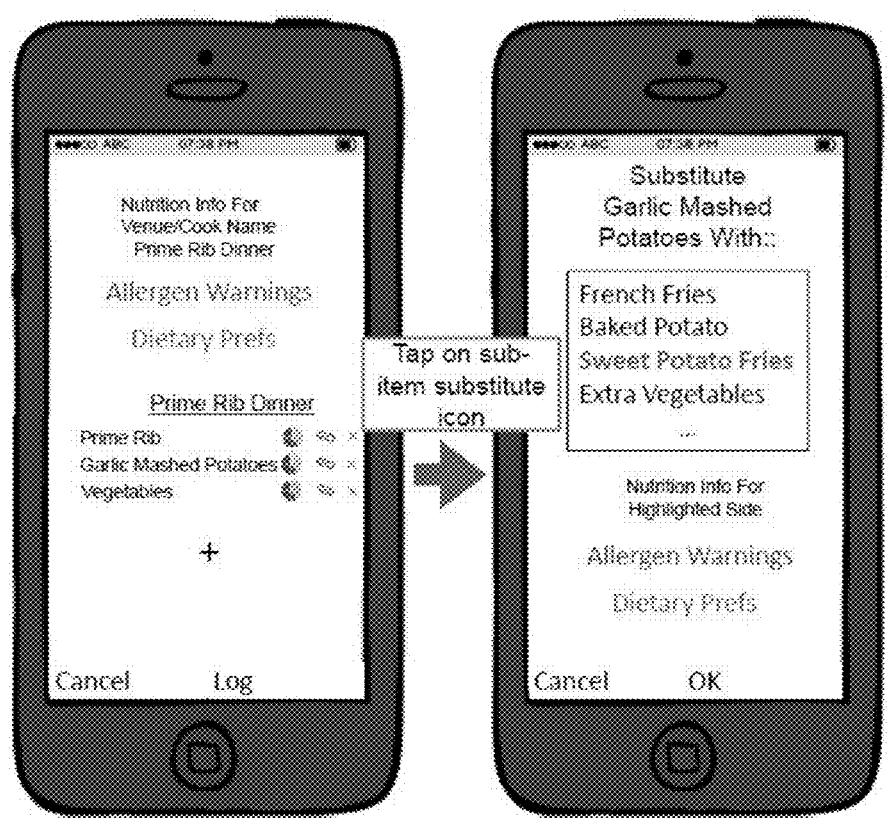
Figure 16I:
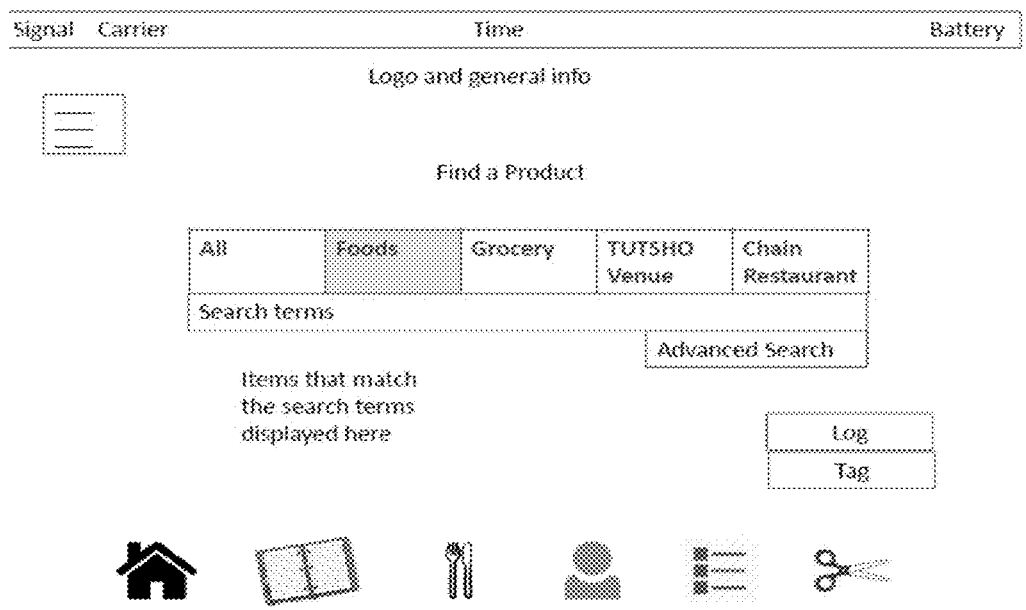
Figure 16J:
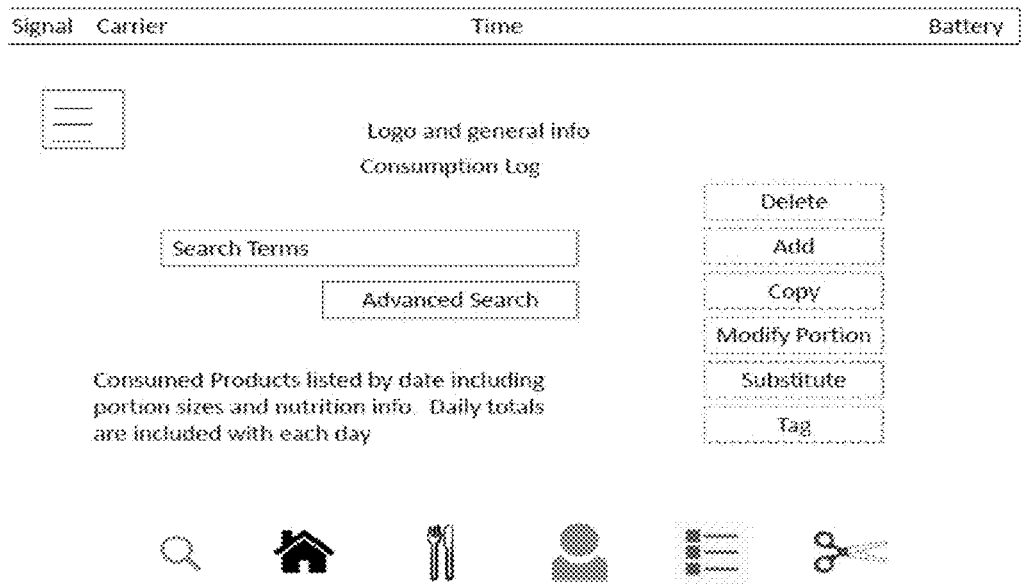
Figure 16K:
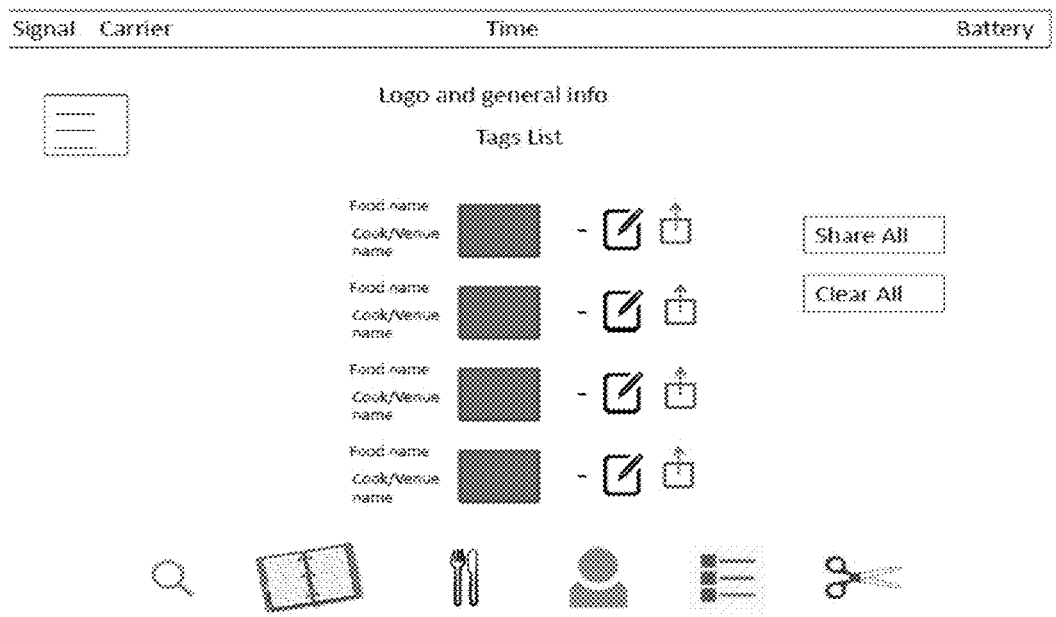
Figure 16L:
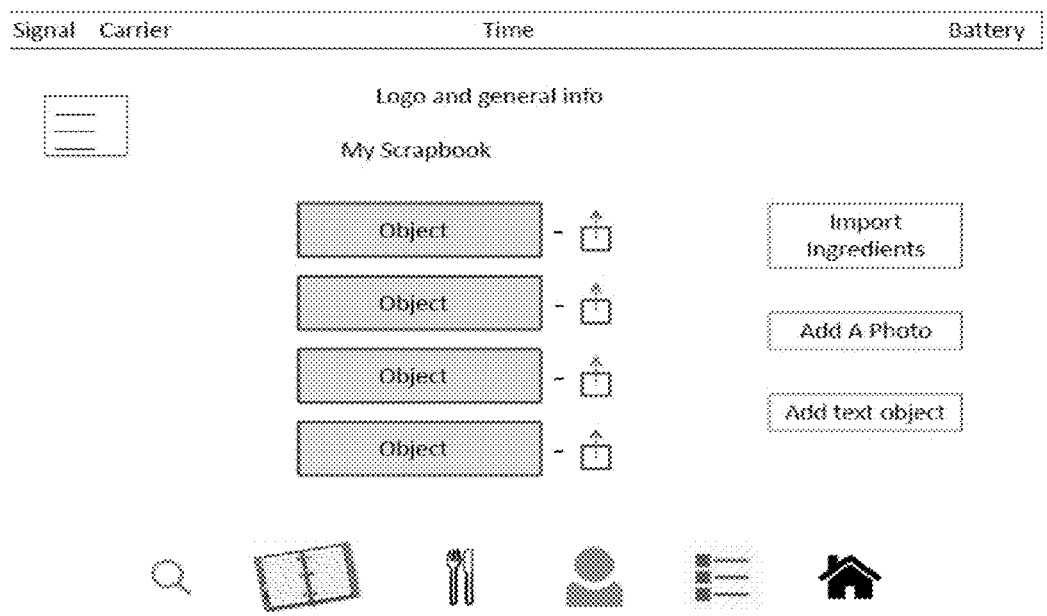
Figure 16M:
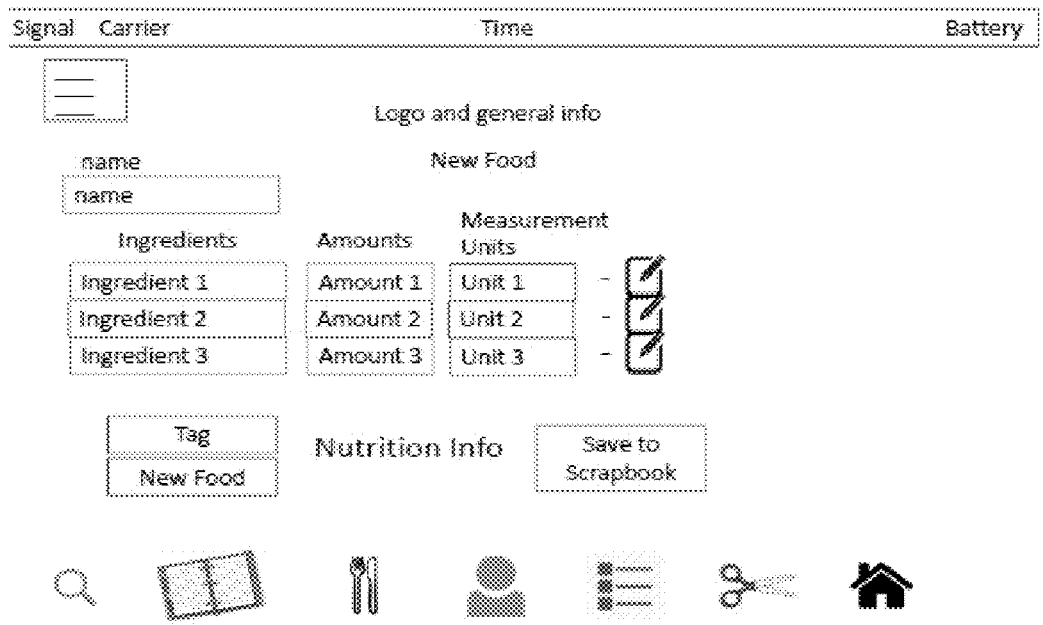
Figure 16N:
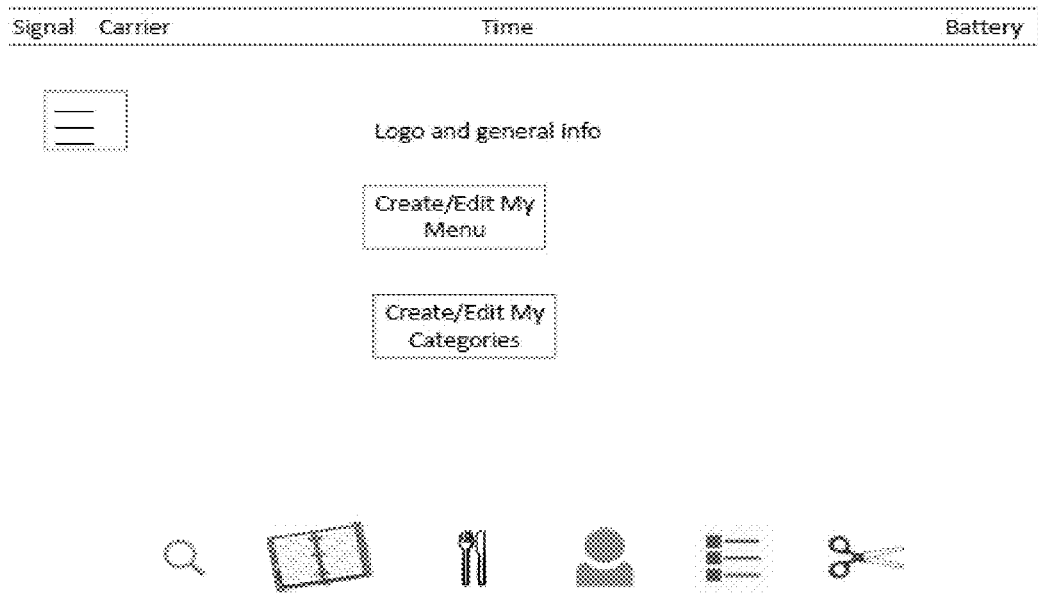
Figure 16O:
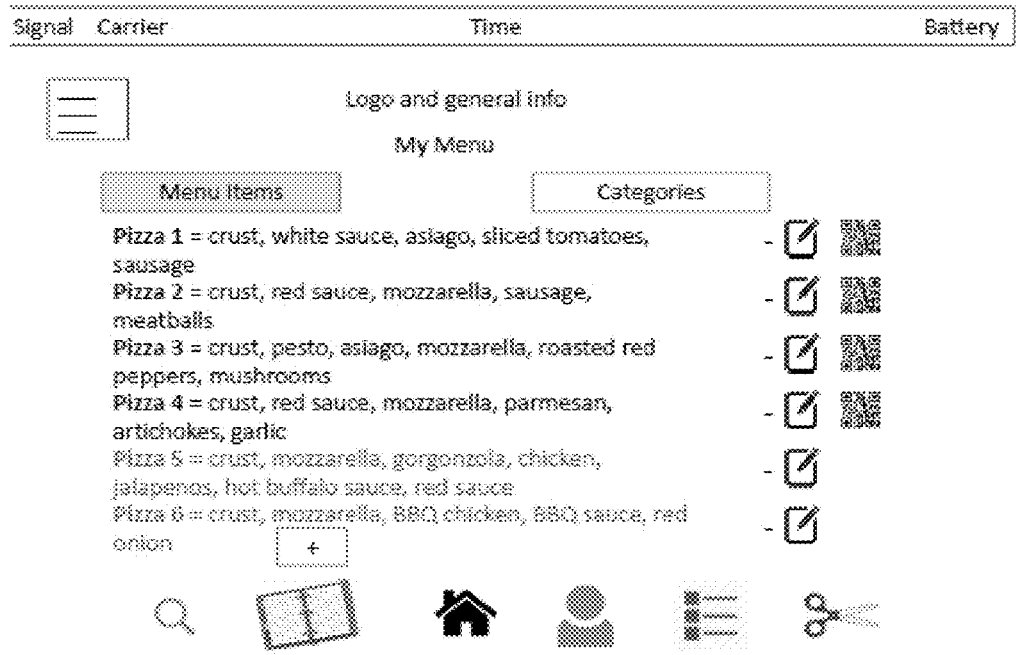
Figure 16P:
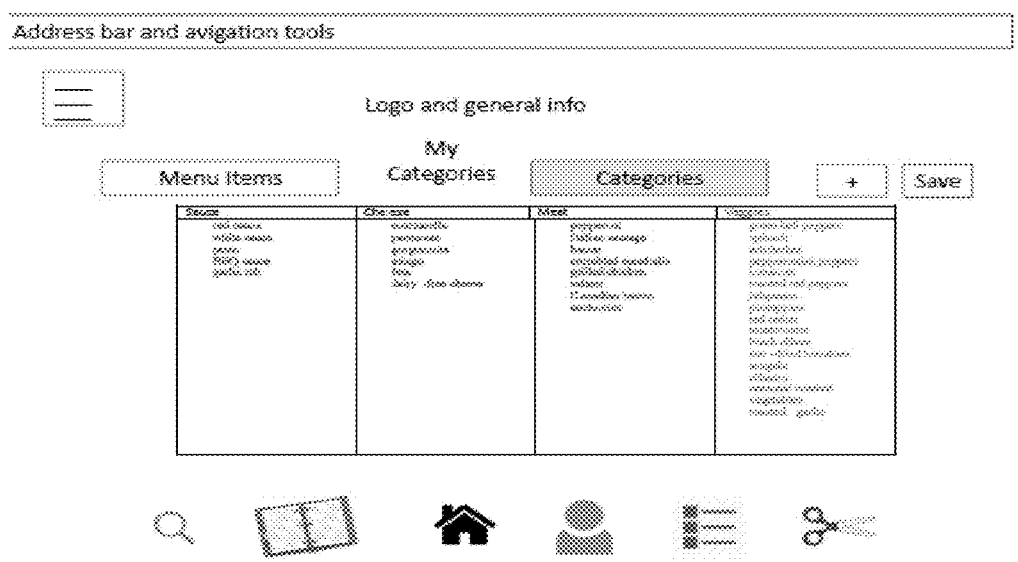
Figure 16Q:

Mobile application wireframes, depicted in FIGS. 16A-16Q.

Figure 17A:
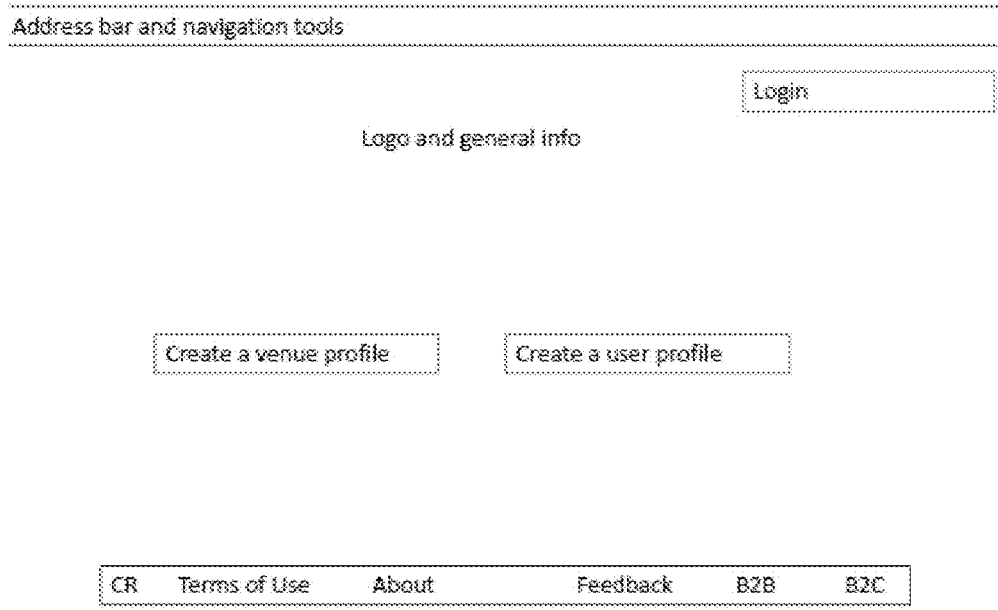
FIGS. 17A-R depict illustrative web application wireframe diagrams, which depict functional elements of a web application user interface.
Figure 17B:
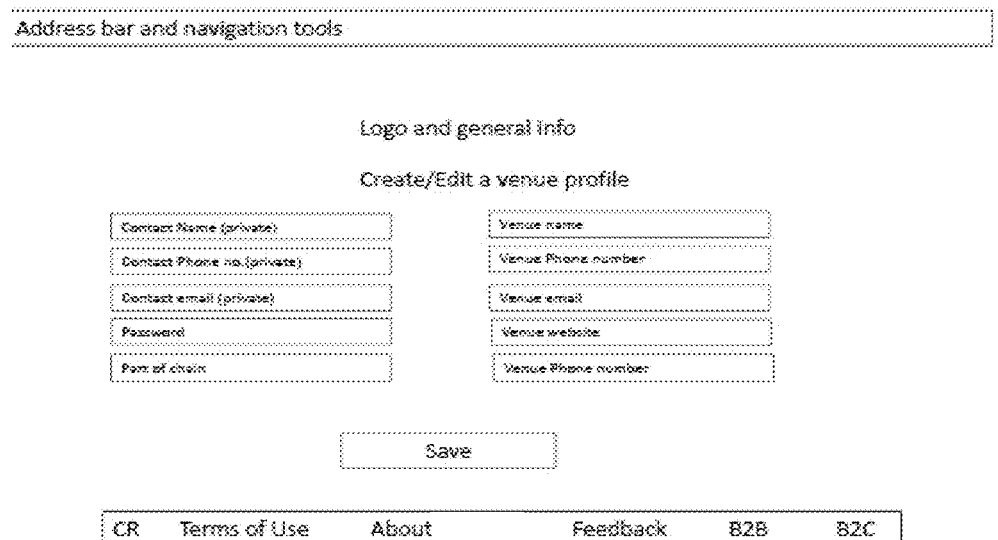
Figures 17C, 17D:
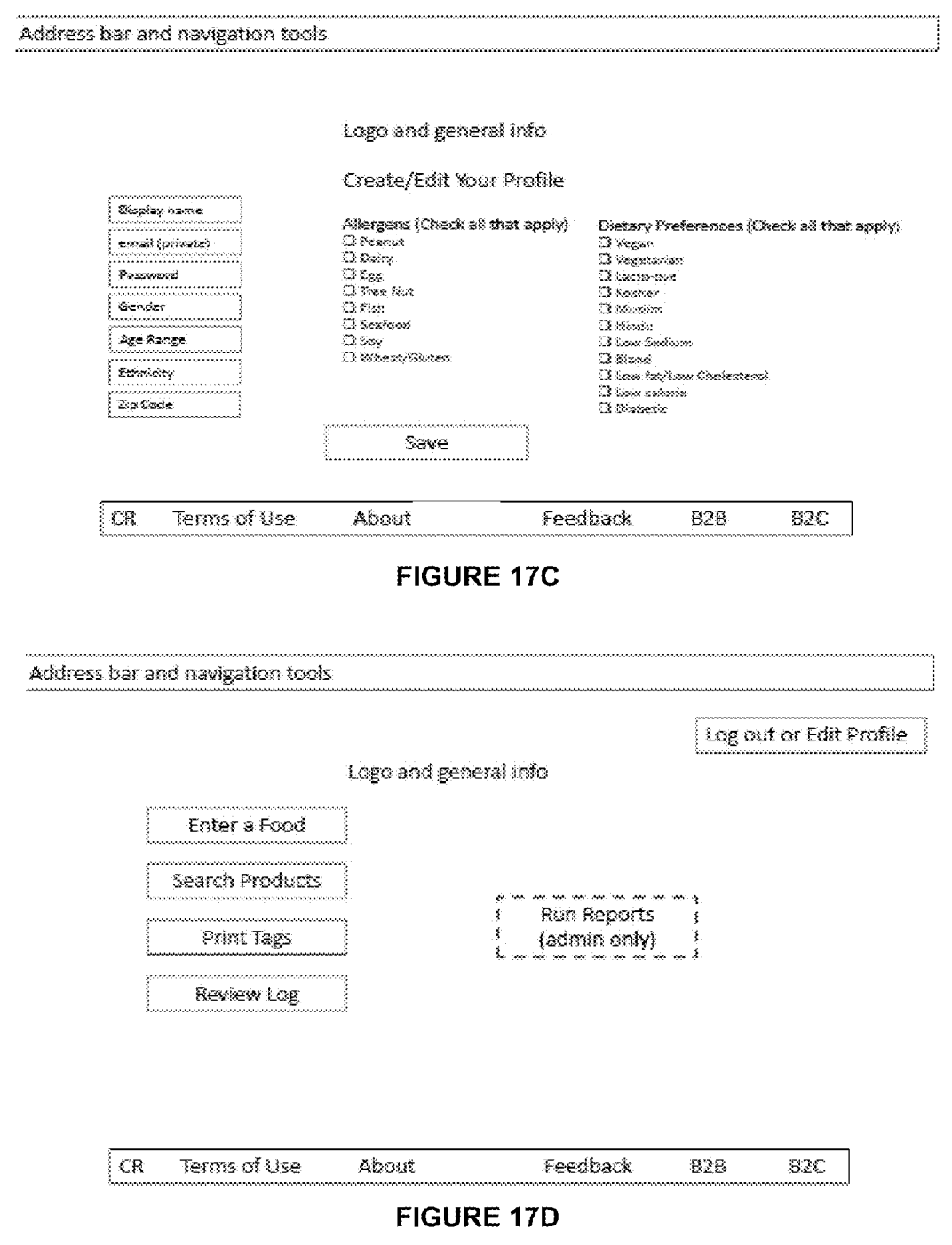
Figure 17E:
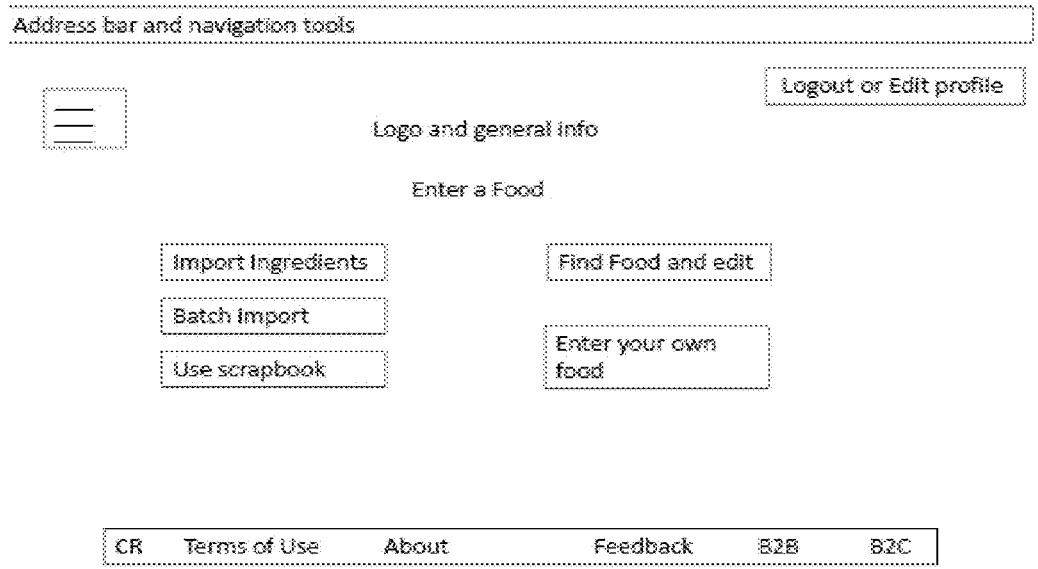
Figure 17F:
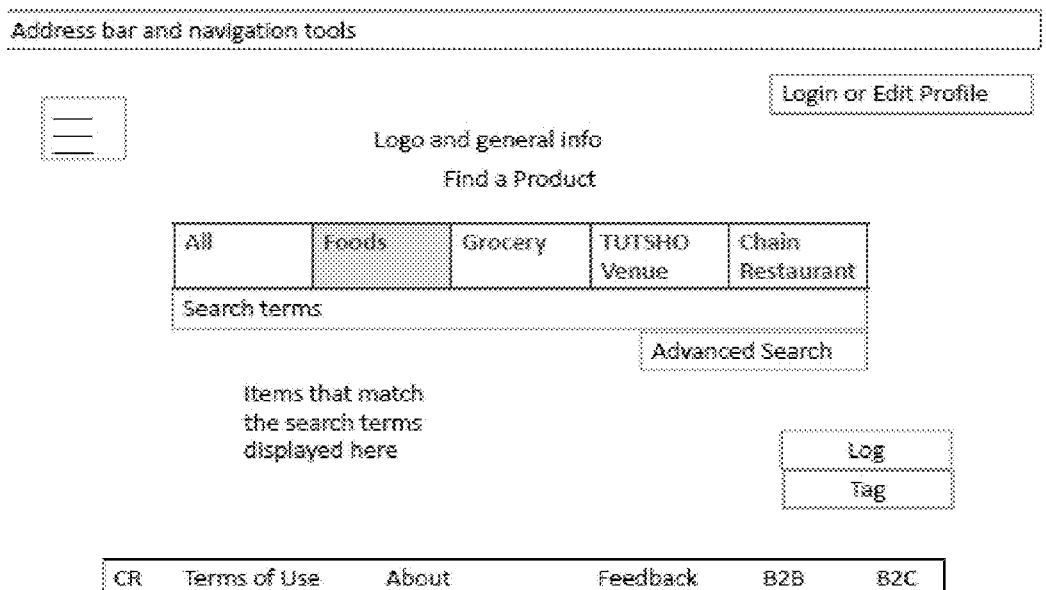
Figures 17G, 17H:
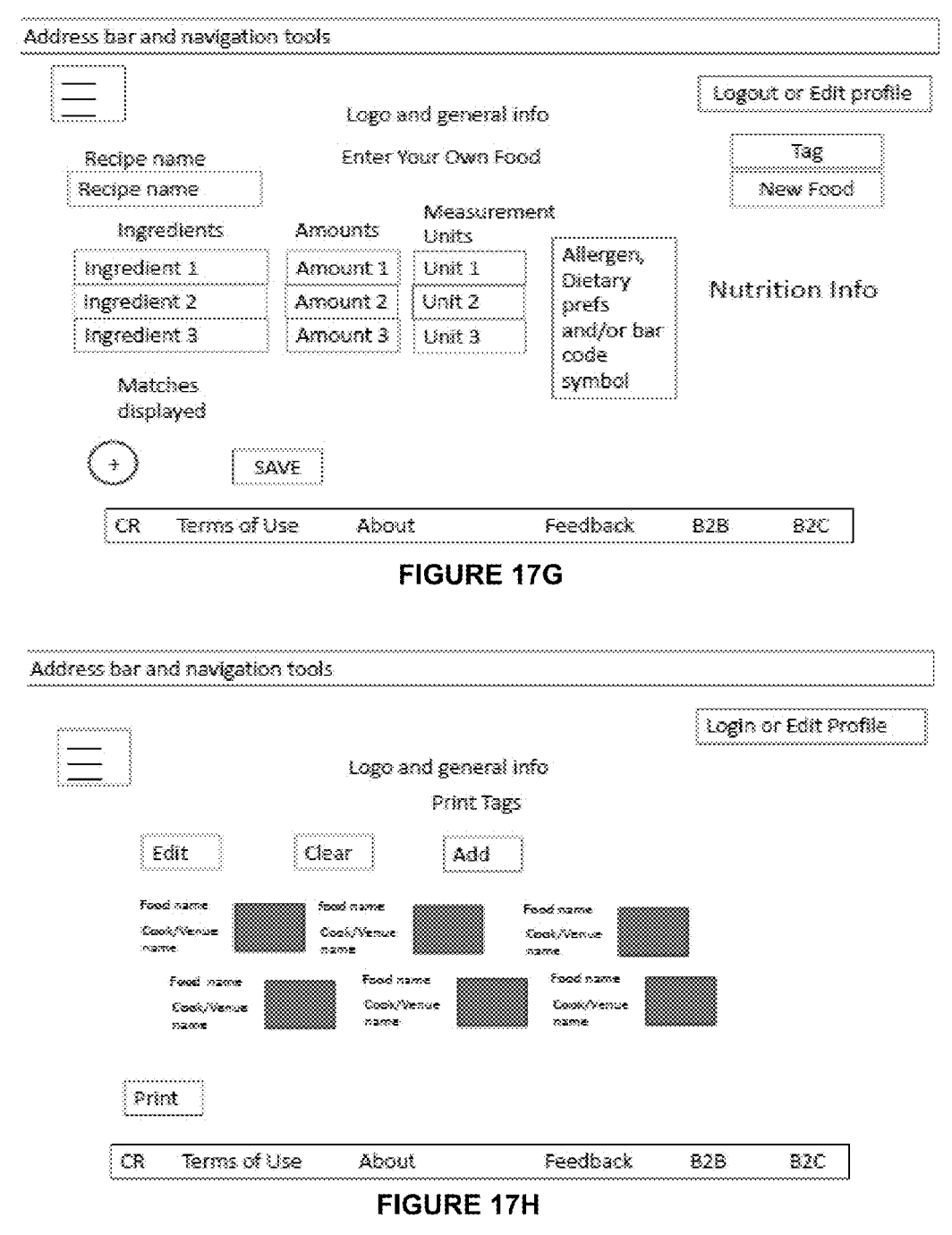
Figure 17I:
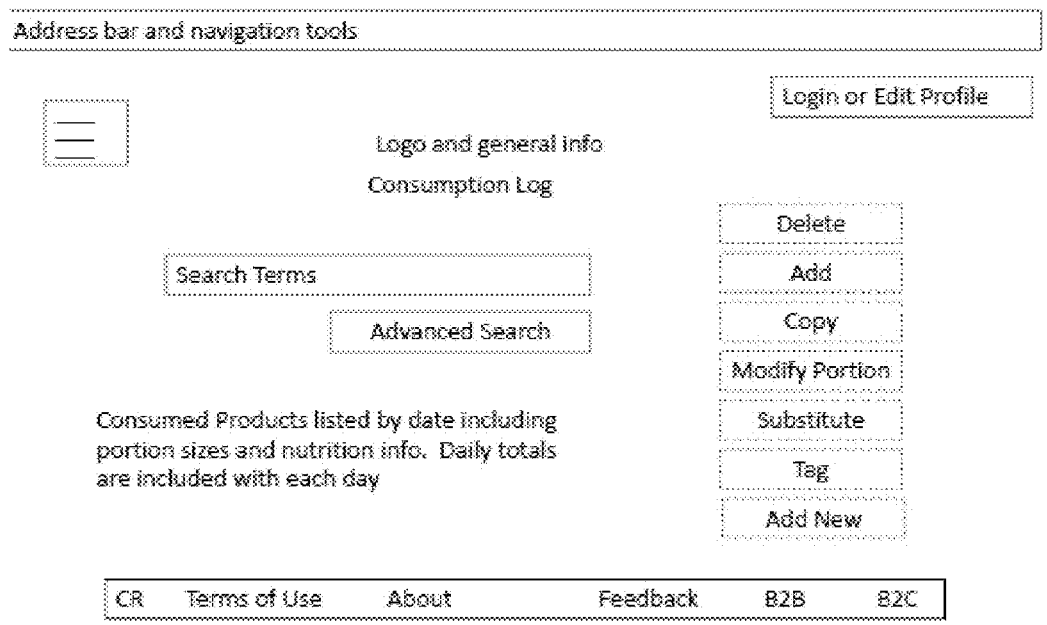
Figure 17J:
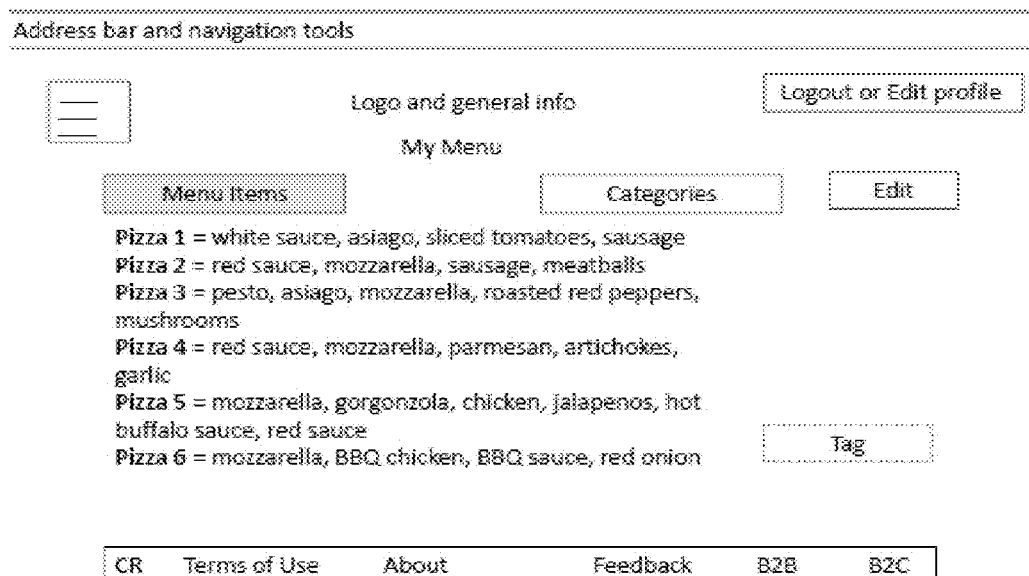
Figure 17K:
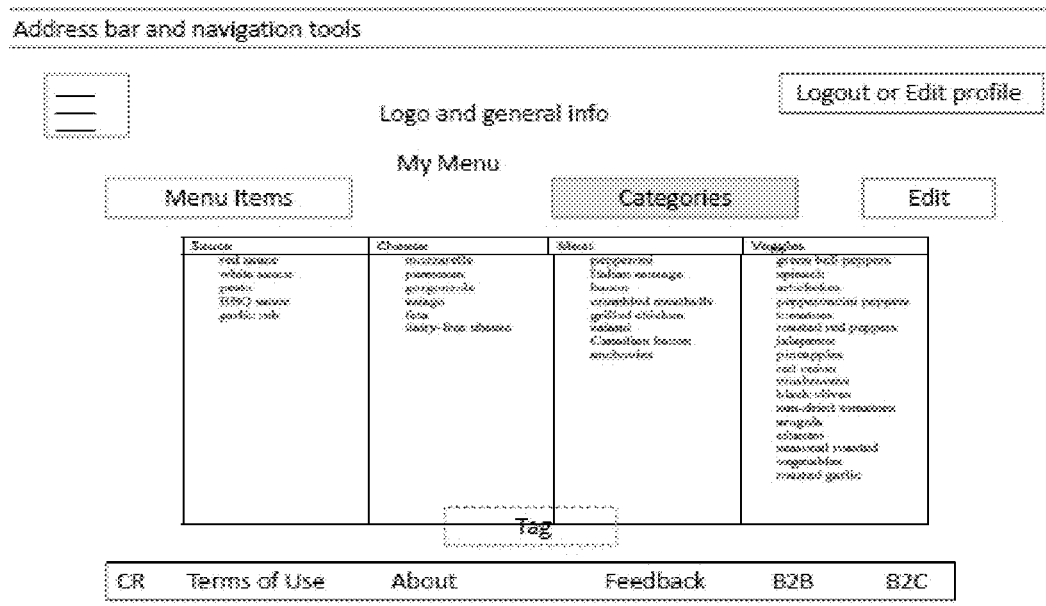
Figure 17L:
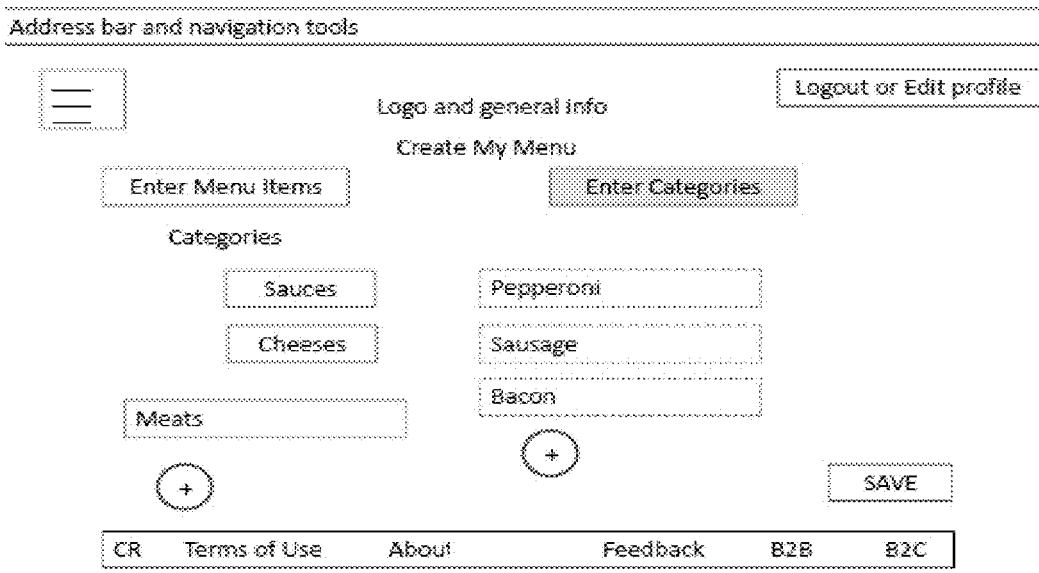
Figures 17M, 17N:
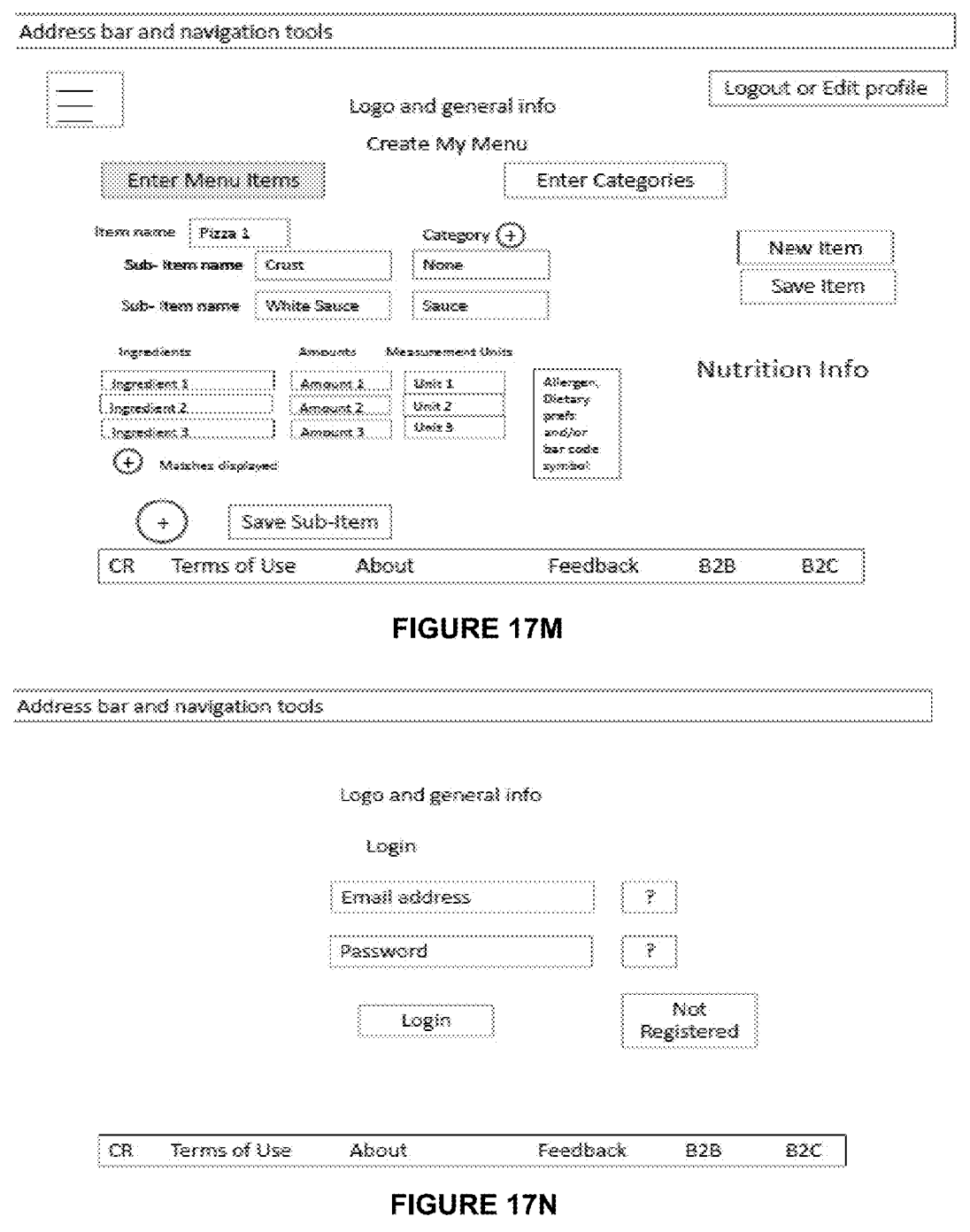
Figures 17Q, 17R:
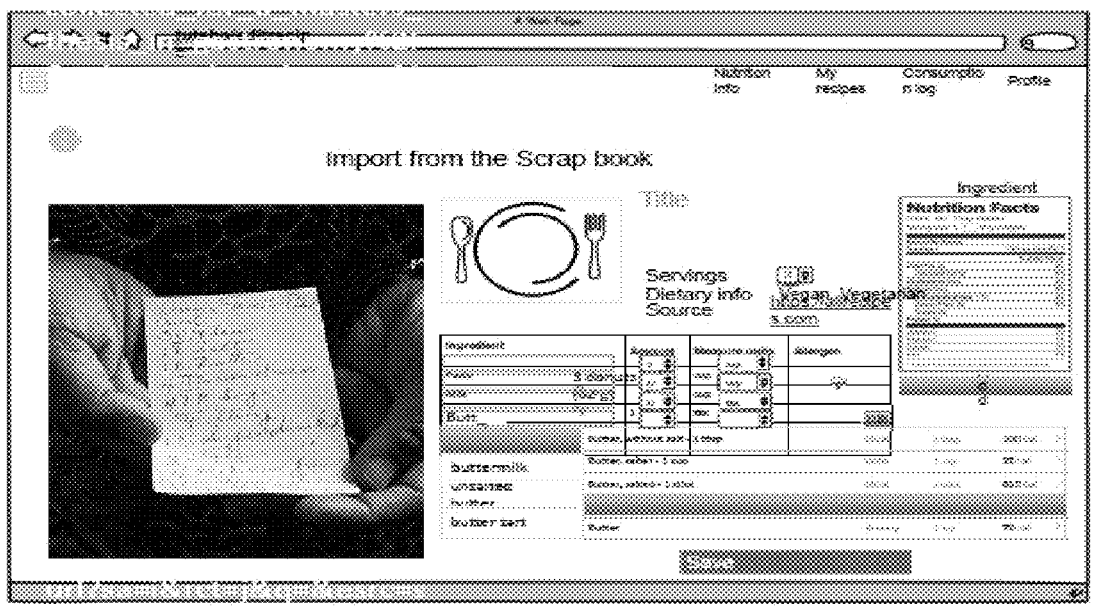

Web application wireframes, depicted in FIGS. 17A-17R. The Web wireframes show an example of the UI where the user would add a name for the new Food, each ingredient, the amount for each ingredient and the measurement units associated with the amount.

Architecture Document

It should be noted, however, that unless specifically so limited, the scope of protection of the claims of the present application is by no means intended to be limited to the specific features depicted in the wireframe diagrams.

A. User Scenarios

Some user scenarios supported in the exemplary base product include:

1. Scan and log user dietary information—Using the mobile app, the user scans a tag associated with a food or beverage the user has consumed or plans to consume. The scanned tag is decoded to display the nutritional and other related information on the user's mobile device. The user may modify the portion size or make substitutions (e.g., side salad instead of potatoes) where applicable to reflect what the user has/will actually consume. The user may save the decoded data, in modified or unmodified form, to the user's consumption log. If the food is not tagged, the user may scan a barcode if available or search for the food from the database (including food served at large chain venues) to identify the relevant nutritional and allergen information.

2. Personal profile matching—When the user registers with the system, the user will identify any dietary preferences (e.g., vegan, vegetarian, diabetic, etc.) or allergies (e.g., dairy, peanuts, etc.). When the user scans a tag with his/her mobile device, the user will be notified if the scanned item is believed to contain any allergens that are identified in his/her profile and whether the item is believed to match a dietary preference.

3. Food Item Creation—Both individual users and venues may enter food items. There are several options for entry. Each ingredient in a prepared food may be individually entered to create a "Food" to be served. The ingredients may be looked-up by searching the database or by the barcode UPC associated with the ingredient. Ingredients may also be imported from certain recipe websites. Users will be provided with electronic scrapbooks that will enable them to copy recipes from notes, pictures, emails, etc. that can later be transcribed into the ingredient entry feature. As ingredients are added, their corresponding nutritional information is acquired through public sources or entered by the user. Allergen information is identified corresponding to the ingredient. The user may identify any dietary preferences associated with the food item. Venues will additionally be able to group sub-items (e.g., meat, potatoes, and vegetables) together in a manner in which they are served at the venue and identify appropriate substitutions (e.g., rice or side salad) or options (e.g. with your turkey sandwich you can have lettuce, tomato, onion, mustard, mayo, pickles, etc.). Users may also search for existing database foods, modify some or all of the ingredients, portion sizes, etc. to create a new food. Venues' ingredient entries may be private and venues optionally can omit ingredient entries and only enter the recipe name and corresponding nutritional and allergen info.

4. Creating and printing tags—Using the web application, users may search for or otherwise identify Foods/Items they wish to tag. Once identified, the user can initiate the encoding process to create a tag for the identified food(s). The user may compile a number of tags along with the Food or Item name in a single print file so that venues may include inserts with their menus or provide signage with the tags within the venue, or other users can make them available to guests at a dinner party or pot luck, for example. The tags may also be stored and viewed in electronic form from both web and mobile apps and emailed electronically to others (web app) or shared with others (mobile app).

5. Consumption log review—Using the web or mobile app, users may view their own consumption logs, filtering the log by date, date range, or other criteria. Users may also search for certain logged foods and modify the portion size, make a substitution, delete the entry, or enter it again for a new date/time. Venues will also be able to review the venue's food items that have been logged by the venue's own customers although the customers' identities/personal info may not be revealed.

6. Administrative—A system administrator may enter recipes/ingredient information on behalf of registered venues and generate usage reports relating to, among other things, tags generated and scanned, recipes created and scanned, and feedback received from users.

B. Food/Item Creation

There are several options for users to create foods for recipes they prepare and for Venues to create Item and Sub-Items that reflect their menus.

1. Users Preparing their Own Foods

The user may enter new Foods in a number of ways in the web application.

Import ingredients from recipes posted on supported websites. The user can either enter the URL for the online recipe from the web app or when the user is viewing the recipe for the ingredients the user wants to import, the user can just click on a designated button from the user's navigation or favorites bar. In either case, as long as the recipe site is supported (i.e., it has a public API or uses a standard metadata scheme), the ingredients will be automatically imported along with the name of the recipe (and corresponding amounts) into the database. If the imported ingredients are found in the database, the nutritional information will automatically be populated as well for relevant amounts and measurement units. If an imported ingredient is not found in the database, the user will be required to enter the nutritional information (described in subpart iii below). Allergens are identified and are not input by a user. The list of ingredients, amounts, measurement units, and nutritional and allergen info will be displayed following the import and any entry required and the user will save or clear the entry. The user will be prompted to enter a dietary preference associated with the new Food but the user is not required to enter the dietary preference and may save the new Food without doing so. After saving, all of the information is logged into the database as a new Food for that user.

Batch import ingredients from recipes posted on supported websites. Users can list up to 10 URLs for recipes and the ingredients from each of those recipes along with the ingredient amounts and recipe names will be imported to the database. The same process described above will be implemented for each of the imported recipes. The database will log these new Foods in association with the user that imported them.

Manual entry of ingredients. The user may enter ingredients from his/her own recipe. The Web wireframes show an example of the UI where the user would add a name for the new Food, each ingredient, the amount for each ingredient and the measurement units associated with the amount (See Enter a Food Page). As the user types in the ingredient, the web app will search the database and begin to list relevant matches. If the user finds a match for the intended ingredient, that match will be selected by the user and will populate the ingredient field. The amount and measurement units will be populated as well. The nutritional info for that ingredient will be displayed for the ingredient as well as any allergens or applicable dietary preferences. The user may change the amounts and measurement units. It should be understood that a variety of methods may be implemented to convert units such as a conversion table or lookups for ingredients having the desired unit match. Those changes will automatically adjust the nutrition information displayed to correspond to the new amounts and units. If the ingredient is not found in the database, the user will enter all applicable information: ingredient name, amount, measurement units, nutrition information, relevant serving size and number of servings for the nutritional values entered, and optionally any dietary preferences. If an ingredient has a barcode, the user may optionally enter in the UPC code and the ingredient name, amount, nutritional info, etc. will be displayed in the UI. Allergens are identified and are not input by a user. As each ingredient is entered the nutritional information is updated to reflect the cumulative nutritional information for all ingredients. The user can continue to add ingredients in this fashion until all of the ingredients for the recipe have been entered. If the user does not complete the input, s/he can save it to his/her Scrapbook and can come back to the same point at a later time. If the user completes the entry, the user saves the Food as a new Food and the ingredients, amounts, measurement units, nutritional info, serving size, number of servings, allergens and dietary references are saved to the database in association with the user that entered the Food. The user will be prompted to enter a dietary preference associated with the new Food but the user is not required to enter the dietary preference and may save the new Food without doing so. Other users should be permitted a way to add dietary preferences in association with any Product in the database.

Edit and Enter an existing food. The user may search for a Food that has already been entered into the database. The user may use the "Find a Product Page" to search for a specific Food or may search his/her Consumption Log to find a Food that he or she already logged. When the Food is found, the user may select "edit" which will bring up the "Enter a Food Page" already populated with the existing Food information. The user may add, delete, or modify ingredients and resave the Food as a new Food associated with the user that made the edits. The same process as described in subpart iii is applicable here.

Enter using the User's Scrapbook. Each user will have a Scrapbook. Using the web app, the user may open his or her scrapbook when entering ingredients for a new Food so that information saved to the user's Scrapbook can be easily transcribed into the relevant fields on the Enter a Food Page as described in subpart iii. If a URL or multiple URLs are in the Scrapbook, they can be copied and imported as described in subparts i or ii above. As described with each of the entry methods above, the user may save the new Food once all of the information has been populated along with optional dietary preferences.

The user may save recipe info to his or her scrapbook from his or her mobile device but the user will not be able to enter new Foods via the mobile app. If the user is using a laptop or tablet, the user may use the web app as described above to enter a new Food. The user could also use the web app on his or her mobile phone but the user interface should not be optimized for these smaller form factors in the base product.

2. Entering Items and Sub-Items Served at a Venue

The venue entry is a superset of the user entry. In order for users to be able to make substitutions, delete sub-items, add extras etc. after scanning a tag, the venue must have its menu items along with all applicable sub-items stored in the database and all applicable substitutable sub-items or add-ons and any extras that may be available from that venue stored in the database. (In this context, "add-on" refers to a category of sub-items that are not substitutes but are things that customers can add to their order; "category" refers to the name of a group of sub-items that can be substituted for one another when ordering an item; "extras" refer to products that are available from a venue but are not listed on the menu; and "substitutes" are sub-items that can be substituted within an item for the default sub-item that is specified on the venue's menu.) The Sample My Menu Pages, Sample Create My Menu Page, and Sample Create My Menu Page included in the Web wireframes should be reviewed along with this description.

Entering Categories. Each venue may have different categories that make sense for the items it serves. The samples shown in the web wireframes are for a pizza restaurant. The customer can order a specific pizza that comes with a sauce, a cheese, a veggie and a meat or some combination of those. In that case, it might make sense to have 4 categories as shown in the samples. Alternatively there could be a single category of add-ons that include some or all the sauces, cheeses, veggies and meats. For example, there could be categories "sauces" and "cheeses" but add-ons that include all possible veggies and meats. It is up to the venue as to what categories to create and what sub-items or add-ons to include. In either case, it would be expected that the customer would order one of the specific pizza combinations and then might want to make a substitution and/or add-on a particular topping. By associating each menu item with appropriate substitutions and add-ons the customer will easily be able to log what he or she actually orders. There may also be a mechanism to input extras that the venue provides such that the user can easily search for and add these if consumed to the user's Consumption Log.

Entering Menu Items. Since a menu item is simply the name that the venue includes on its menu to define something to order, the nutrition information, allergens and dietary preferences are determined by the specific sub-items associated or grouped together to form an Item. In the pizza example, in addition to the sauces, cheese, etc., there would also be the pizza crust. Some venues might have multiple types of crust in which case a Category would need to be created but if there is only one type of crust, crust would always be included as a default sub-item with any Item. As another example, consider a venue that prepares a daily quiche. The quiche (the "Item") has 2 sub-items, the filling and the crust. Assuming the daily quiche is homemade both the filling and the crust would be associated with a specific recipe for which the ingredients, amounts, measurement units, etc. would be added as descripted in Part 1 subpart iii above.

3. My Menu or My Foods

A user should be able to access the Foods he or she has entered and saved by clicking on My Foods from both the mobile and the web app. Similarly a venue should be able to click on My Menu from the web and mobile app and bring up its Menu Items, sub-items, Categories, add-ons and Extras.

C. Scanning and Logging

Scanning takes place solely from the mobile app but there are several other options for logging products into a user's consumption log. The database stores ingredients from the USDA database and other available nutrition databases including groceries (bar-coded products) and foods available from certain large-chain restaurants. In addition, the database stores the user entered foods as well as the venue entered information. A product is anything in the database that has nutritional information associated with it. In other words, a product includes every food, menu Item, sub-item, add-on, extra, grocery, and chain restaurant food. In addition to scanning, a user can search for a product in the database and log the product or the user can search his or her foods or consumption log to find a food or previously consumed meal to log. The user may also scan a bar code on a grocery to include the grocery in the user's consumption log.

Scanning a Tag and Logging a Venue Item

The mobile app Home page includes the "Scan a Tag" function which launches the QR code scanner. The user uses the scanner to scan a Tag generated for a Venue Item. The mobile app decodes a Tag. The decoded nutrition information is displayed as shown in the mobile wireframes for the entire Item. Each sub-item is shown for the Item Tag scanned along with options to modify the portion size, substitute another Sub-Item, or delete the Sub-Item. There should also be options to include an Add-On if there are Add-Ons and Extras (not shown). If the user chooses to modify the portion size, the Sub-Item alone will be shown with a portion size UI feature. The user adjusts the portion size to reflect what s/he has or will consume. The nutritional information for that Item will then update to reflect that the Sub-Item portion size was adjusted. The user can also choose the substitute option which will bring up the default Sub-Item and a list of sub-items that can replace the default sub-item. The user may select one of the listed sub-items which will then replace the default sub-item in the menu Item and the mobile app with update the nutrition app after the substitution is made. If there are Add-Ons or Extras, the user can click on those options in connection with an Item (not Sub-Item) and again a list would be presented to which the user can select the ones he or she has or will consume with the Item. Once the user has made all appropriate changes and additions, he or she may save the Item to his or her Consumption Log. In doing so, the time, date, Venue, Menu Item, Sub-Items with portion sizes, add-ons, if any, with portion sizes, Extras, if any, with portion sizes, along with the cumulative nutrition information will be save in the database in association with the user's Consumption Log.

Figure 18A:
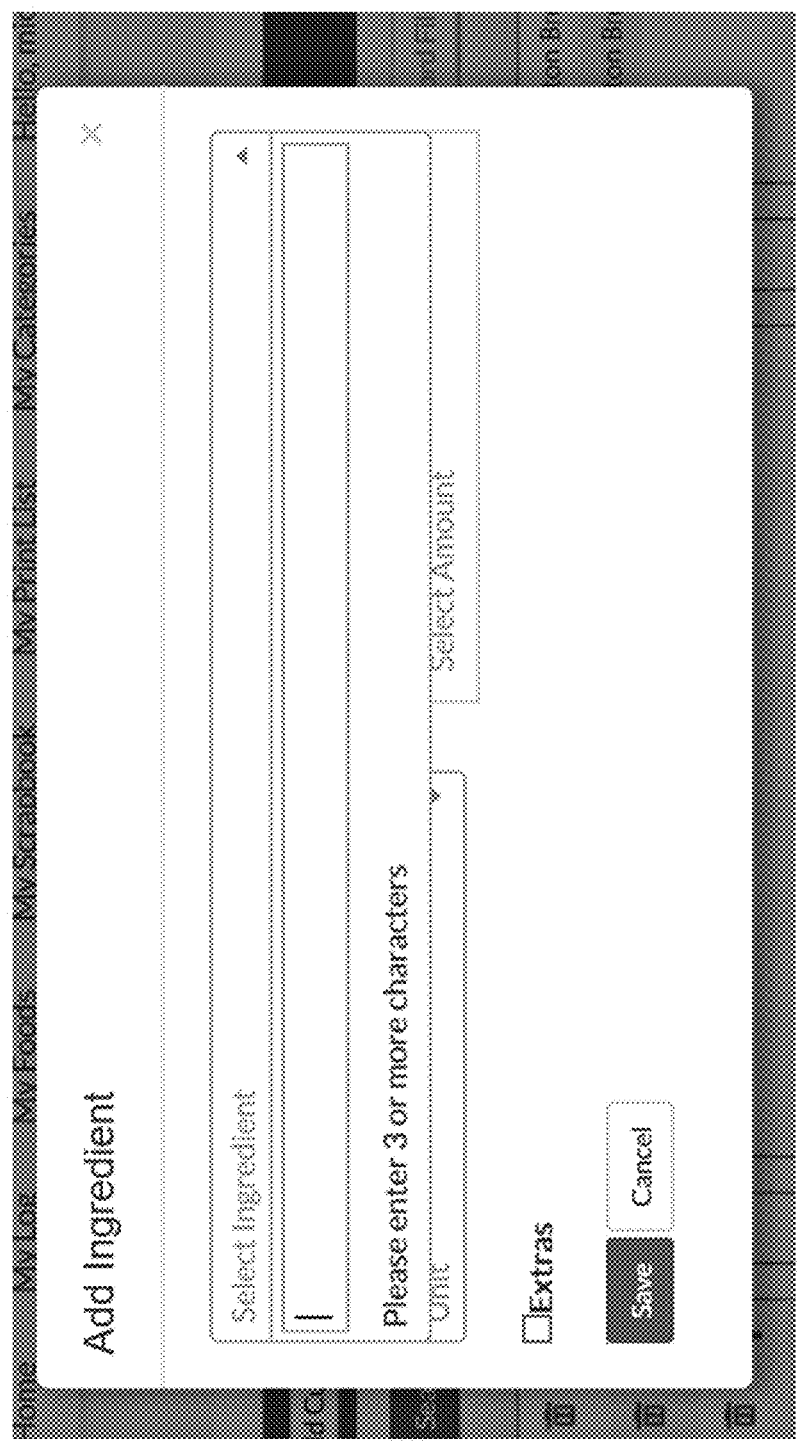
FIGS. 18A, 18B, and 18C depict exemplary user interface elements designed for the efficient input of a new ingredient as an extra and the creation of a meal by grouping together ingredients and recipes.
Figure 18B:
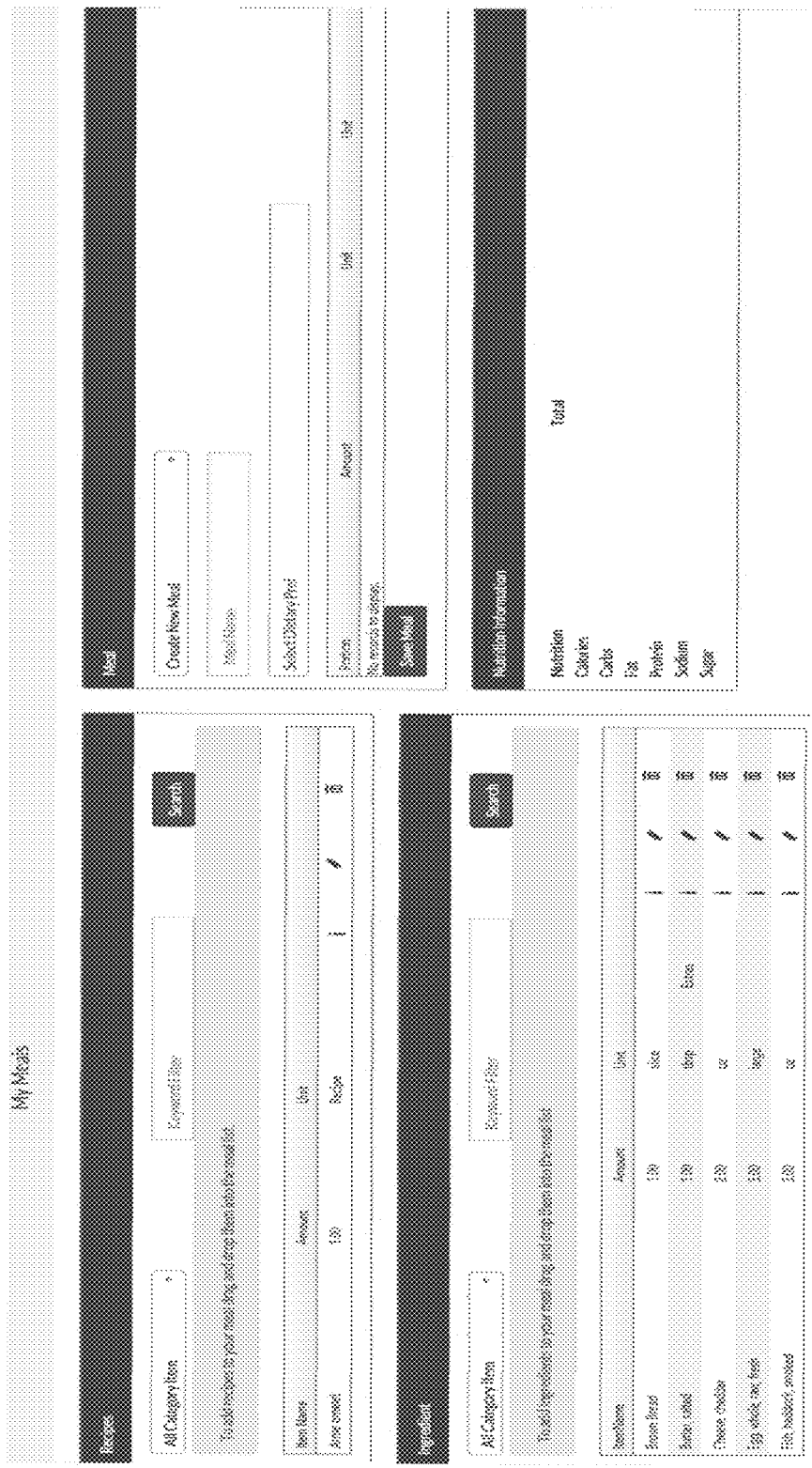
Figure 18C:
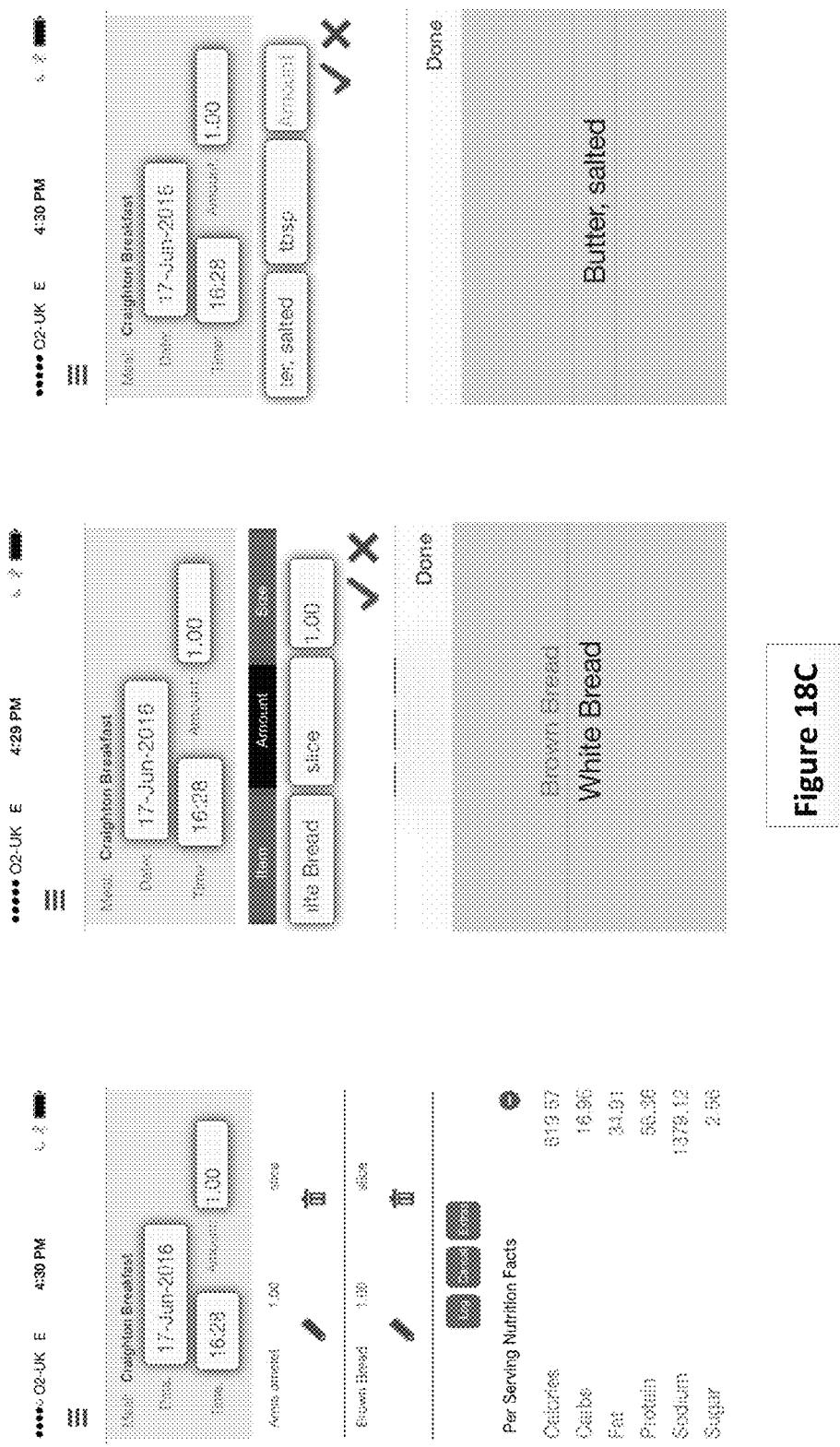

It should be understood that categories and extras may be used by individual cooks as well as venues for creating meals according to the present invention. FIGS. 18A-C show additional user interface examples for inputting a new ingredient as an extra and creating a meal by grouping together ingredients and recipes. In the user interface shown, ingredients such as brown bread and the Arnie Omelet are grouped together by dragging and dropping them into a new meal. When the a tag for that meal is scanned, the user can select brown bread and substitute white bread or select extras and select butter as shown in FIG. 18C.

Scanning a Barcode and Logging a Grocery Product

The mobile app Home Page also includes the "Scan a Barcode" function which brings up the barcode scanner. The user uses the scanner to scan a barcode on a Grocery. The barcode is decoded to identify the UPC and the UPC is looked up in the database to bring up the nutritional information for the Grocery. The mobile app UI displays the name of the Grocery, the serving size and nutritional information along with an option to change the portion size. The portion size and nutrition update process is described above. If the user saves the Grocery to his or her Consumption Log, the time, date, Grocery name, UPC, amount, and nutritional info will be saved to the database for that user's Consumption Log.

Logging an Existing Product or Food

The user can search for products or foods in a number of ways. Upon identifying an ingredient, grocery, venue item or chain restaurant item in the database, the user can change the portion size and log the applicable product into the user's consumption log creating a new entry for that user along with the date, time, and name of the product. If the product is a venue item, the user will also be able to make substitutions, additions, and deletions. If the user searches for a food that has been entered by the user or any user, the user can elect to edit the food as described above. The food in modified or unmodified form may be logged by the user to his or her consumption log, creating a new entry with the date, time, and name of the unmodified food or new food, along with the applicable nutrition info.

Importing a Recipe

This section describes ways to implement the feature "Import recipe from existing website/API".

Several ways of importing imply creating a "list of supported websites". This means, that only recipes from sites in this list get imported directly to the app. It is possible to import recipes from unsupported websites to the app's Scrapbook. This can be done using a browser extension, an embedded browser view, a website API, a mobile device "share" feature, or email.

Architecture

FIG. 13 depicts an illustrative, basic architecture including a database server, app server, and user level including a mobile app user and a web app user.

| Module | Description |
| --- | --- |
| Database Server | A computer or virtual machine (VM) dedicated to host MS SQL database. |
| App Server | A computer or VM that hosts web resources and REST API. |
| Web App User | Users that access app from web browser. |
| Mobile App User | Users that run mobile app. |

Each module is described in detail below.

Database Structure

The database contains the following information:
User profiles. Table contains information about each user in system, such as first and last name, unique user ID, email, password, allergies, dietary preferences etc.
Consumption log. Table contains detailed information about user dish consumption.
Nutrition values. Table contains nutrition values for each food in database, such as Calories, Total Fat, Sodium, Protein, etc.
Recipes. Table store food components grouped into recipes. For example—Burger: beef, red onions, extra-virgin olive oil, mayonnaise, salt, etc.
Allergy information—Table contain information about compatibility between foods and allergens, to produce allergy warnings.

App Server Components

Presentation layer:
ASP.NET MVC—responsible for providing HTML, CSS, JS resources for web clients.
ASP.NET Web API—REST API framework.
Data-access layer, ORM: Entity Framework 6—provides object mapping to database entities.
Business logic layer—classes that implement all application-specific logic.

Web Application Components

The web application uses an established web development framework as a base and follows the framework development guidelines and best practices. Example frameworks include Angular JS with additional plugins and directives, and Twitter Bootstrap 3. It should be understood that numerous other technical architectures may be used to implement the inventive system such as the architecture illustrated in FIG. 13.

Mobile Application Components

The mobile application can be based on PhoneGap (also called Apache Cordova) or Xamarin to simplify cross-platform development. The same development framework used in the web application is preferably used to simplify development and reuse components where possible. The main features of the mobile app are:

Uses QR scanner PhoneGap plugin

For best performance, different plugins can be used for iOS and Android

Split into components according to framework

Accesses REST API for data.

Additional Material

QR Code Structure

The QR Code stores basic recipe nutrition information, allergy and dietary compliance data and recipe ID. To form a QR Code, these numbers are encoded as bytes and concatenated to a fixed-length number. It incorporates both Venue and Users.

The basic tag encoding may be implemented substantially in accordance with the following format and conversion to a QR code. A 2-byte value provides a maximum of 65535 different entries.

| Field | Size |
| --- | --- |
| Cook or venue no | 2 bytes |
| Recipe no | 2 bytes |
| Recipe Name | X bytes |
| Portion Size | Y Bytes |
| Calories | 2 bytes |
| Total Fat | 2 bytes |
| Cholesterol | 2 bytes |
| Sodium | 2 bytes |
| Total Carbohydrate | 2 bytes |
| Protein | 2 bytes |
| Allergens (encoded as yes/no bit fields): Milk, Eggs, Fish, crustacean shellfish, tree nuts, peanuts, wheat, soybean | 1 byte |
| Dietary Preferences (encoded as yes/no bit fields): Vegan, Vegetarian, Kosher | 2 bytes to cover 11 |
| ... | |
| Total | 19 + X Y bytes |

A QR-code with 32 binary encoded bytes:
cook:~$ xxd 8 bytes
0000000: 0123 4567 89ab cdef 0123 4567 89ab cdef .
Eg . . . #Eg . . . .
cook:~$ cat 8 bytes|qrencode -1 L -8 -o 8 bytes.png The QR Code according to this format should not need to exceed about 0.5 inches when printed based on capability of user devices scanning/imaging technology. It should be understood that further compression may be achieved by predefining other features of the fields or by eliminating certain fields. It should be further understood that different encoding schemes will have better compression characteristics and may be used instead of QR encoding.

Service-Oriented Architecture

Figure 14:
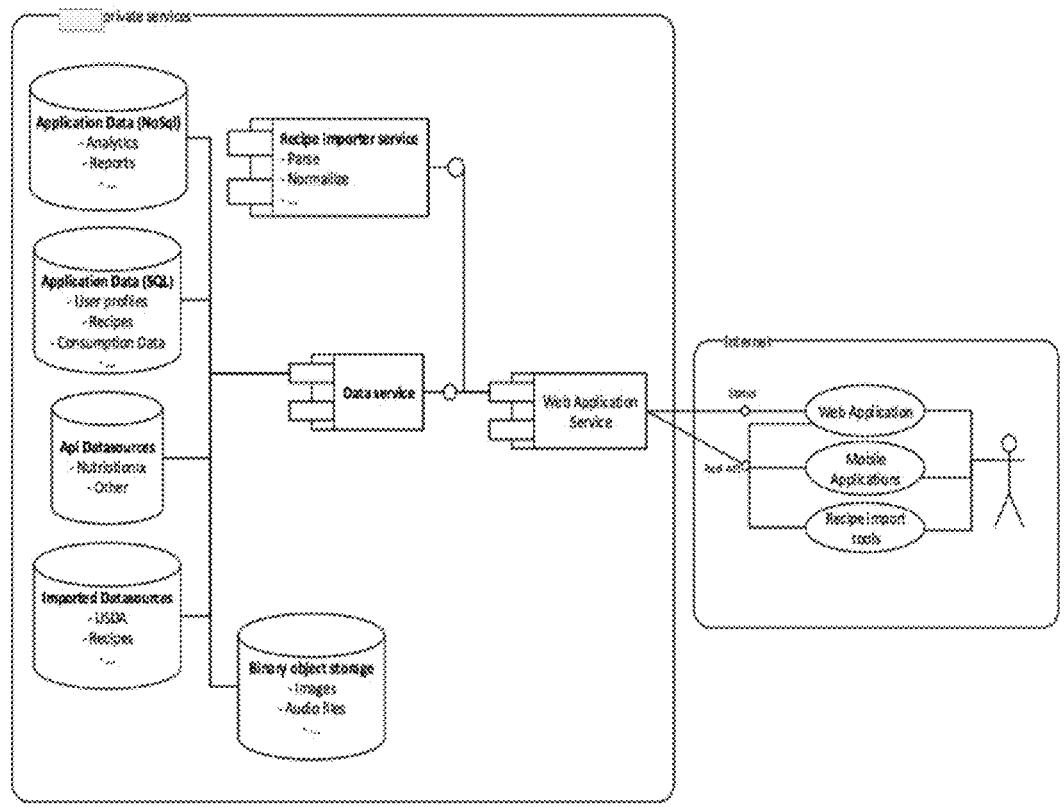
FIG. 14 depicts an overview of a service-oriented architecture (SOA) for enhanced scalability and extensibility.
Figure 15:
FIG. 15 depicts an example theme for an Admin Area.

For enhanced scalability and extensibility, the service-oriented architecture (SOA) may be used. The high level overview of main services is depicted in FIG. 14.

As described above and shown in FIGS. 13 and 14, the inventive system includes at least one nutrition database that is interfaced to the application server. For illustrative purposes only such nutrition databases may be third party databases such as one made available by Nutritionix or the USDA database. The Nutritionix API information can be found at http://www.nutritionix.com/business/apt. The following lists the relevant links for the USDA data, API, and allergen lists.

Raw Ingredients

USDA National Nutrient Database for Standard Reference http://www.ars.usda.gov/main/site_main.htm?modecode=80-40-05-25

Documentation and User Guide http://www.ars.usda.gov/SP2UserFiles/Place/80400525/Data/SR27/sr27_doc.pdf info on the API http://ndb.nal.usda.gov/ndb/doc/index Allergens Eggs: http://www.kidswithfoodallergies.org/page/egg-allergy.aspx Fish: http://www.foodallergy.org/allergens/fish-allergy Seafood: http://www.foodallergy.org/allergens/shellfish-allergy Diary: http://www.kidswithfoodallergies.org/page/milk-allergy.aspx Peanuts: http://www.kidswithfoodallergies.org/page/peanut-allergy.aspx Tree nuts: http://www.kidsswithfoodallergies.org/page/tree-nut-allergy.aspx, Soy: http://www.kidswithfoodallergies.org/page/soy-allergy.aspx Wheat/Gluten: http://www.kidswithfoodallergies.org/page/wheat-allergy.aspx The service-oriented architecture provides an ability to address application scalability and reliability needs. As each application feature is backed by a simple service, it can be easily scaled, without affecting other components. Moreover, as the services are loosely coupled (access only over HTTP Rest API), each service can be included/excluded from the system according to specific needs. Moreover, the SOA-based approach naturally blends with cloud-based solution deployment, which ensures even faster and simpler responses to increased load and hardware malfunctioning.

User Interface Designs for Mobile and Web Applications

As mentioned above, FIGS. 16A-Q depict illustrative mobile app wireframe diagrams and FIGS. 17A-R depict illustrative web application wireframe diagrams. These are generally referenced above in the sections describing example objectives for a base product. Unless the claims are specifically so limited, the claims of the present application are by no means intended to be limited to the specific features depicted in the wireframe diagrams.

III. PDA/Smartphone-Based Tag Reading System, FIG. 18

Figure 19:
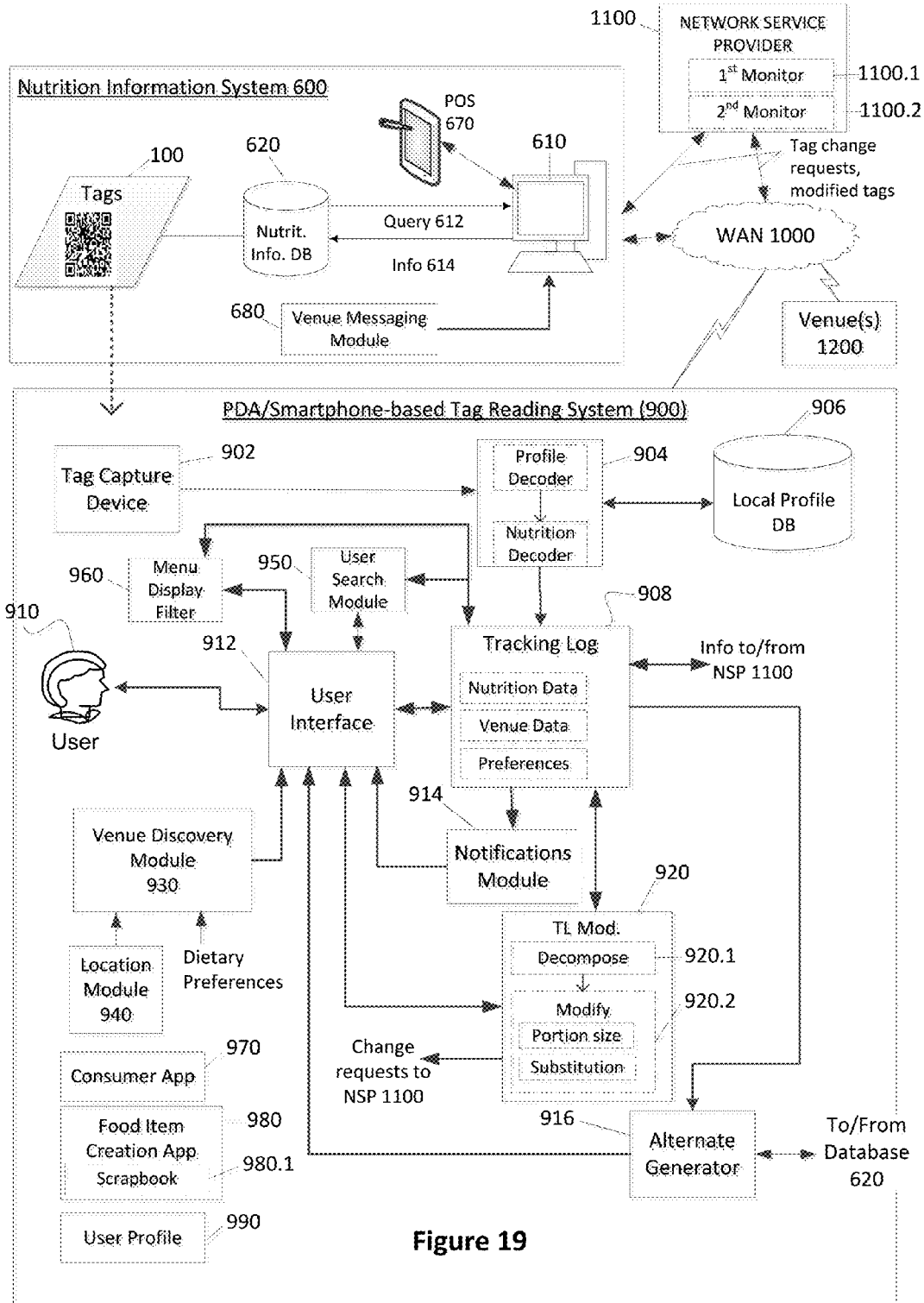
FIG. 19 schematically depicts a presently preferred embodiment of an overall system in accordance with the present invention.

FIG. 19 depicts a presently preferred embodiment of a system in accordance with the present invention. As shown, the inventive system includes a nutrition information system 600 and a PDA or smartphone-based tag reading system 900. The two systems 600 and 900 are configured to communication via a wide area network 1000. A network service provider 1100 and one or more venue(s) 1200 may also communicate with the system via the wide area network 1000.

In addition, in the illustrative embodiment, a first network service provider monitor 1100.1 is configured to enable a network service provider 1100 to monitor user logs and provide alerts and suggestions regarding general dietary trends. In addition, a second network service provider monitor 1100.2 is configured to enable a network service provider to evaluate a venue's customer purchases and provide suggestions about when the venue should buy new supplies or to have specials to encourage sales of perishable foods. It be noted that the network service provider(s) is (are) not limited to people, as they could be completely automated.

In the illustrative embodiment of FIG. 19, the nutrition information system 600 includes a database 620 storing dietary product descriptions and associated nutritional information, and a computer 610 coupled to the database and configured to generate a nutritional tag 100. The tag 100 is configured to represent a subset of the dietary product descriptions and associated nutritional information based upon a predetermined profile. The nutritional tag preferably includes at least a header or visual effects indicative of the predetermined profile.

In the illustrative embodiment of FIG. 19, the nutrition information system 600 also includes a venue messaging module 680 to enable a venue to access a user's log of tracked items and to send a message to the user when tracked items are on special and when a new item added to the venue's menu is determined, based on user's log, to be of possible interest to user.

The mobile tag reading system 900 of FIG. 19 includes a tag capture device 902 for reading the nutritional tag, and a decoder 904 for decoding the header or visual effects included in the nutritional tag to identify the predetermined profile. The tag capture device may be an optical device but it is not limited to optical devices. The decoder 904 is also configured to decode the nutritional tag to generate the subset of the dietary product descriptions and associated nutritional values based upon the predetermined profile. In addition, a tracking log modification module 920 is included in the tag reading system to enable a user to modify the dietary product descriptions and the associated nutritional values. A tracking log 908 is also included for storing the associated nutritional values or the modified associated nutritional values based upon input from the user.

The tag reading system 900 may also include a food item creation module 980 to enable the creation of nutritional tags for newly created foot items. A discovery module 930 is also included for providing the user with a list of network-registered venues based on the user's current location and the user's dietary preferences. This feature enables the user to select a nearby venue offering items compatible with the user's dietary preferences.

The tag reading system may also include a user search module 950 to enable the user to search the user's log, and to display information in the venue fields. This is especially useful in cases where the user is a customer of a specific venue. A menu display filter 960 is advantageously included to enable the user to scan a unique venue tag and view a personalized menu of only those items that meet the user's dietary requirements. Also included is a consumer application 970 configured to use downloaded items to enable the user to substitute one item or sub-item with another item or sub-item. Finally, a local profile database 906 may also be included in the tag reading system. (It should be noted that querying of venue tags could go through the tracking log or the query could go right to the database 620 or 906 with the venue information with a request to match against certain user profile information contained in the user's profile.)

In the description above, sub-items may be formed from one or more ingredients. If more than one ingredient is included, the ingredients are grouped together to form the sub-item. Items or menu items can include one or more sub-items. If more than one, the sub-items are grouped together to form the item. A user can make changes to the sub-items based on actual consumption. In some cases those changes could be to ingredients if the sub-item contains only a single ingredient, e.g. butter. Changes to the ingredient lists denote changes to a recipe, not necessarily the user's consumption.

CONCLUSION

The true scope the present invention is not limited to the illustrative embodiments disclosed herein. For example, the foregoing disclosure of presently preferred embodiment of a tag reading system uses explanatory terms, such as tag capture device, decoder, and tracking log, which should not be construed so as to limit the scope of protection of the following claims, or to otherwise imply that the inventive aspects of the system are limited to the particular methods and apparatus disclosed. Moreover, as will be understood by those skilled in the art, many of the inventive aspects disclosed herein are based on software applications running on known and ubiquitous hardware processing platforms. These functional entities are, in essence, programmable data collection and processing devices that could take a variety of forms without departing from the inventive concepts disclosed herein. In some cases, the structural details of a given element, as well as the place of implementation, of an element described herein will be a designer's preference based on presently available technologies and cost constraints, and not a hard requirement. Accordingly, except as they may be expressly so limited, the scope of protection of the following claims is not intended to be limited to the specific embodiments described above.

We claim:

1. A tag reading system configured for use with a nutrition information system, said nutrition information system including a database storing dietary product descriptions and associated nutritional information, and a computer coupled to the database and configured to generate a nutritional tag representing a subset of the dietary product descriptions and associated nutritional information based upon one of a plurality of predetermined profiles, wherein the nutritional tag comprises at least one of a header and visual effects indicative of the predetermined profile, the tag reading system comprising:
   a tag capture device for reading the nutritional tag;
   a decoder for first decoding the header or visual effects included in the nutritional tag to identify the predetermined profile, and then decoding the nutritional tag to generate the subset of the dietary product descriptions and associated nutritional values based upon the predetermined profile;
   a tracking log for accumulating nutritional values extracted from previously read nutritional tags;
   a tracking log modification means for creating modified nutritional values in the tracking log based on food substitutions selected by a user; and
   wherein the nutrition information system is further configured to enable (i) a network service provider to monitor user logs and provide alerts and suggestions regarding general dietary trends and (ii) a user to provide subjective input concerning how the user feels; the tag reading system is configured to log the times of food consumption and the times at which the user provides the subjective input; and the nutrition information system is further configured to identify correlations between certain dietary or nutrition trends and the user's subjective input, and to provide observations about such correlations to the user or third party identified by the user.

2. The tag reading system of claim 1, wherein the tracking log modification means is configured to decompose the nutritional information into constituent ingredients and amounts, and to modify the constituent ingredients or amounts in accordance with user input to reflect the user's actual consumption.

3. The tag reading system of claim 1, wherein the tracking log modification means is further configured to change portion size information for specific sub-items.

4. The tag reading system of claim 1, wherein the tracking log modification means is further configured to make substitutions among sub-items and then modify corresponding nutritional information accordingly.

5. The tag reading system of claim 2, wherein the tracking log modification means is further configured to make a substitution for a sub-item and then modify portion size information for the substituted sub-item.

6. A tag reading system configured for use with a nutrition information system, said nutrition information system including a database storing dietary product descriptions and associated nutritional information, and a computer coupled to the database and configured to generate a nutritional tag representing a subset of the dietary product descriptions and associated nutritional information based upon one of a plurality of predetermined profiles, wherein the nutritional tag comprises at least one of a header and visual effects indicative of the predetermined profile, the tag reading system comprising:
a tag capture device for reading the nutritional tag;
a decoder for first decoding the header or visual effects included in the nutritional tag to identify the predetermined profile, and then decoding the nutritional tag to generate the subset of the dietary product descriptions and associated nutritional values based upon the predetermined profile;
a tracking log for accumulating nutritional values extracted from previously read nutritional tags;
tracking log modification means for creating modified nutritional values in the tracking log based on food substitutions selected by a user; and
wherein the nutritional tag further comprises venue fields populated by a registered venue and the venue fields include a venue network identifier, name of item to be tagged, price of item, and a flag indicating whether the item is subject to a promotion.

7. The tag reading system of claim 6, wherein the tracking log is configured to enable the user to record venue order information corresponding to a past order at a specific venue.

8. The tag reading system of claim 7, wherein the tag reading system further comprises a notifications module configured to remind the user of the past order when the user enters the specific venue.

9. The tag reading system of claim 8, wherein the notifications module is further configured to remind the user of the past order when the user enters a different venue with the same menu as the specific venue.

10. The tag reading system of claim 6, further comprising a venue discovery module for providing a user with a list of network-registered venues based on the user's dietary preferences and current location as determined by a location module, thereby enabling the user to select a nearby venue offering items compatible with the user's dietary preferences.

11. The tag reading system of claim 6, wherein the nutrition information system further includes a venue messaging module to enable a venue to send a message to the user based on information contained in the tracking log or a user profile associated with the tag reading system.

12. A tag reading system configured for use with a nutrition information system, said nutrition information system including a database storing dietary product descriptions and associated nutritional information, and a computer coupled to the database and configured to generate a nutritional tag representing a subset of the dietary product descriptions and associated nutritional information based upon one of a plurality of predetermined profiles, wherein the nutritional tag comprises at least one of a header and visual effects indicative of the predetermined profile, the tag reading system comprising:
a tag capture device for reading the nutritional tag;
a decoder for first decoding the header or visual effects included in the nutritional tag to identify the predetermined profile, and then decoding the nutritional tag to generate the subset of the dietary product descriptions and associated nutritional values based upon the predetermined profile;
a tracking log for accumulating nutritional values extracted from previously read nutritional tags;
tracking log modification means for creating modified nutritional values in the tracking log based on food substitutions selected by a user; and
wherein each predetermined profile permits nutritional data to be encoded in the form of numeric values without encoding units of measurement or a text description of the nutritional information.

13. The tag reading system of claim 12, wherein the tracking log modification means is configured to decompose the nutritional information into constituent ingredients and amounts, and to modify the constituent ingredients or amounts in accordance with user input to reflect the user's actual consumption.

14. The tag reading system of claim 12, wherein the tracking log modification means is further configured to change portion size information for specific sub-items.

15. The tag reading system of claim 12, wherein the tracking log modification means is further configured to make substitutions among sub-items and then modify corresponding nutritional information accordingly.

16. The tag reading system of claim 13, wherein the tracking log modification means is further configured to make a substitution for a sub-item and then modify portion size information for the substituted sub-item.

17. The tag reading system of claim 12, wherein the tracking log modification means is configured to send a change request to a network service provider, said change request instructing the network service provider to generate a modified nutritional tag.

18. The tag reading system of claim 17, wherein the change request further instructs the network service provider to provide the modified nutritional tag for decoding and logging.

19. The tag reading system of claim 18, wherein the tracking log is accessible to the network service provider, and wherein the change request further instructs the network service provider to make changes directly to the user's data log.

20. The tag reading system of claim 17, wherein the nutrition information system further includes a point of sale terminal configured to send a change request to the network service provider based on an order or preference of a customer.

21. The tag reading system of claim 13, wherein the tracking log is configured to enable the user to record venue order information corresponding to a past order at a specific venue.

22. The tag reading system of claim 21, wherein the tag reading system further comprises a notifications module configured to remind the user of the past order when the user enters the specific venue.

23. The tag reading system of claim 22, wherein the notifications module is further configured to remind the user of the past order when the user enters a different venue with the same menu as the specific venue.

24. The tag reading system of claim 12, further comprising a venue discovery module for providing a user with a list of network-registered venues based on the user's dietary preferences and current location as determined by a location module, thereby enabling the user to select a nearby venue offering items compatible with the user's dietary preferences.

25. The tag reading system of claim 12, wherein the nutrition information system further includes a venue messaging module to enable a venue to send a message to the user based on information contained in the tracking log or a user profile associated with the tag reading system.

26. The tag reading system of claim 12, wherein the nutrition information system is configured to enable a network service provider to monitor user logs and provide alerts and suggestions regarding general dietary trends.

27. The tag reading system of claim 26, wherein the nutrition information system is further configured to enable a user to provide subjective input concerning how the user feels.

28. The tag reading system of claim 27, wherein the tag reading system is configured to log the times of food consumption and the times at which the user provides the subjective input.

29. The tag reading system of claim 28, wherein the nutrition information system is further configured to identify correlations between certain dietary or nutrition trends and the user's subjective input, and to provide observations about such correlations to the user or third party identified by the user.

30. The tag reading system of claim 12, wherein the nutrition information system is further configured to enable a network service provider to evaluate a venue's customer purchases and provide suggestions to improve inventory and recipe costing.

31. The tag reading system of claim 12, wherein the nutritional tag further comprises a loyalty field configured to initiate a counter in the tracking log when an item is purchased by a user with a network identifier.

32. The tag reading system of claim 31, wherein the tracking log is configured to provide an alert to indicate availability of a free or discounted purchase when a specified number of purchases are made.

33. The tag reading system of claim 12, wherein the nutritional tag further comprises venue fields populated by a registered venue.

34. The tag reading system of claim 33, wherein the venue fields include a venue network identifier, name of item to be tagged, price of item, and a flag indicating whether the item is subject to a promotion.

35. The tag reading system of claim 33 further comprising a user search module to enable a user to search and view information in the venue fields.

36. The tag reading system of claim 12, further comprising a menu display filter configured to scan a unique venue tag and display a personalized menu of only those items that meet a user's dietary requirements.

37. The tag reading system of claim 12, further comprising a consumer application configured to use downloaded items to enable a user to substitute one item or sub-item with another item or sub-item.

38. The tag reading system of claim 12, further comprising a food item creation means for enabling the creation of nutritional tags for newly created foot items.

39. The tag reading system of claim 38, wherein the food item creation means comprises a scrapbook application configured to display objects having ingredient information side by side with the food item creation display.

40. The tag reading system of claim 39, wherein the scrapbook application contains any combination of images, text, audio, and video objects.

* * * * *